United States Patent
Belli et al.

(10) Patent No.: US 7,423,137 B2
(45) Date of Patent: Sep. 9, 2008

(54) NUCLEIC ACIDS ENCODING RECOMBINANT 56 AND 82 KDA ANTIGENS FROM GAMETOCYTES OF EIMERIA MAXIMA AND THEIR USES

(75) Inventors: Sabina I. Belli, Lane Cove (AU); Nicholas C. Smith, Roseville (AU); Michael Wallach, St. Ives (AU)

(73) Assignee: Abic Biological Laboratories Teva, Ltd., Beit Shemesh (IL)

( * ) Notice: Subject to any disclaimer, the term of this patent is extended or adjusted under 35 U.S.C. 154(b) by 498 days.

(21) Appl. No.: 10/483,159

(22) PCT Filed: Jul. 3, 2002

(86) PCT No.: PCT/US02/21233

§ 371 (c)(1),
(2), (4) Date: Sep. 13, 2004

(87) PCT Pub. No.: WO03/004683

PCT Pub. Date: Jan. 16, 2003

(65) Prior Publication Data

US 2005/0033042 A1 Feb. 10, 2005

Related U.S. Application Data

(60) Provisional application No. 60/303,699, filed on Jul. 6, 2001.

(51) Int. Cl.
C07H 21/04 (2006.01)
C07K 14/00 (2006.01)
C12P 21/04 (2006.01)
C12N 1/10 (2006.01)
A61K 39/012 (2006.01)
A61K 39/00 (2006.01)

(52) U.S. Cl. .............. 536/23.7; 435/69.3; 435/69.7; 435/258.4; 435/320.1; 530/300; 530/350; 424/265.1; 424/271.1

(58) Field of Classification Search ............ 536/23.7; 435/69.3, 69.7, 258.4, 320.1; 530/300, 350; 424/265.1, 271.1
See application file for complete search history.

(56) References Cited

U.S. PATENT DOCUMENTS 5,496,550 A 3/1996 Wallach et al.
5,932,225 A 8/1999 Wallach et al.

FOREIGN PATENT DOCUMENTS

| EP | 0135712 | 3/1985 |
|---|---|---|
| EP | 0164176 | 11/1985 |
| EP | 0167443 | 1/1986 |
| EP | 0256536 | 1/1996 |
| WO | WO 9000403 | 1/1990 |
| WO | WO 03004683 | 1/2003 |

OTHER PUBLICATIONS

Rudinger et al, in "Peptide Hormones", edited by Parsons, J.A., University Park Press, Jun. 1976, p. 6).*
Jobling et al. (Mol. Microbiol. 1991, 5(7): 1755-67.*
Bumstead et al Clinical and Diagnostic Laboratory Immunology, Sep. 1995, p. 524-530.*
Danforth, H.D., et al., A Review of Progress in Coccidial Vaccine Development, In Vith Intnl.Coccidiosis Conf., Guelph, Ontario, Canada, Barta, J.R. and Fernando, M.A.,(ed.), pp. 49-60 (1993).
Eschenbacher, K. H., et al., Characterization of a 14kDa oocytst wall protein of Eimeria tenella and E. acervulina, Parasitol., vol. 112:169-176 (1995)(Abstract).
Fried, M., et al., Developmental gene expression of a 230-kilodalton macrogamete-specific protein of the avian coccidial parasite, Eimeria maxima, Mol. & Biochem. Parasitol., vol. 51:251-262 (1992).
Gilbert, et al., An Enzyme-Linked Immunosorbent Assay for Coccidiosis in chickens: Correlation of Antibody Levels with Prior Exposure to Coccidia in the Laboratory and in the Field, Avian Disease, vol. 32:688-694 (1988).
Hein, H., Eimeria Brunette: Cross Infections in Chickens Immunized to E. maxima, Experimental Parasitology, vol. 29:367-374 (1971).
Karkhanis, Y.D., et al., Purification and characterization of a protective antigen for Eimeria tenella, Infect. & Immun., vol. 59:983-989 (1991).
Kowlaczyk et al., Quantitation of Maternal-Fetal Egg Transport in the Chicken, Immunology, vol. 54:755-762 (1985).
Larsen, N.C., et al., Production and Partial Characterization of Monoclonal Antibodies Specific for the Gamonts of Eimeria tenella, The J. Parasitology, vol. 77(6):1012-1015 (1991).
Laxer, M.A., et al., Production of Monoclonal Antibodies Specific For Eimeria tenella Microgametocytes, The J. Parasitology, vol. 73(3):611-616 (1987).

(Continued)

Primary Examiner—Shanon A. Foley
Assistant Examiner—Padma v Baskar
(74) Attorney, Agent, or Firm—John P. White; Cooper & Dunham LLP

(57) ABSTRACT

The present invention provides the recombinant cloning and sequencing of two of the major Eimeria maxima gametocyte antigens having molecular weights of 56 and 82 kDa and the expression of these recombinant antigens in an E. coli expression system using the plasmid pTrcHis. The subject invention also provides a vaccine against coccidiosis comprising the recombinant 56 kDa or 82 kDa antigen. The subject invention also provides two 30 kDa proteins and three 14 kDa proteins from Eimeria maxima gametocytes having at the N-terminal end the amino acid sequence described herein. The subject invention also provides a vaccine against coccidiosis comprising the recombinant 56 kDa or 82 kDa antigen and any of the aforementioned proteins. Additionally, the subject invention also provides a method of immunizing a subject against infection by Eimeria tenella, Eimeria maxima, Eimeria acervulina, Eimeria necatrix, Eimeria praecox, Eimeria mitis or Eimeria brunetti, or a microorganism expressing an immunologically cross-reactive antigen, comprising the step of administering to the subject any of the aforementioned vaccines.

20 Claims, 36 Drawing Sheets

OTHER PUBLICATIONS

Long, P.L., et al., Effects of Fowl Sera on Some Stages in the Life Cycle of *Eimeria tenella*, *Experimental Parasitology*, vol. 14:210-217 (1963).

Long, P.L., et al., Immunity to coccidiosis: effect of serum antibodies on cell invasion by sporozoites of Eimeria in vitro, *Parasitology*, vol. 65:437-445 (1972).

Losch et al., The Chicken Egg, an Antibody Source, *J. Vet Med B*. vol. 33:609-619 (1986).

Mencher, D. et al., Antigenic proteins of *Eimeria maxima* gametocytes: cell-free translation and detection with recovered chicken serum, *Exp. Parasitol.*, vol. 68:40-48 (1989)(Abstract).

Pugatsch, T., et al., *Eimeria maxima*: Isolation of Gametocytes and Their Immunogenicity in Mice, Rabbits, and Chickens, *Experimental Parasitology*, vol. 68:127-134 (1989).

Rose, M.E., Immunity to *Eimeria brunetti* and *Eimeria maxima* infections in the fowl, *Parasitology*, vol. 57:363-370 (1967).

Rose et al., Immunity to coccidiosis: protective effects of transferred serum and cells investigated in chick embryos infected with *Eimeria tenella*, *Parasitology*, vol. 63:299-313 (1971).

Rose, M.E., Immunity to Coccidiosis: maternal transfer in *Eimeria maxima* Infections, *Parasitology*, vol. 65:273-282 (1972).

Rose, M.E., Protective antibodies in infections with *Eimeria maxima*: the reduction of pathogenic effects in vivo and a comparison between oral and subcutaneous administration of antiserum, *Parasitology*, vol. 68:285-292 (1974).

Rose, M.E., Immunity to *Eimeria maxima*: Reactions of Antisera in vitro and Protection in vivo, *The Journal of Parasitology*, vol. 60(3):528-530 (1974).

Rose, M.E., Immunity to coccidiosis: stages of the life- cycle of *Eimeria maxima* which induce, and are affected by, the response of the host, *Parasitology*, vol. 73:25-37 (1976).

Rose, M.E., Eimeria, *Current Topics in Microbiology and Immunology*, (A. Clarke, et al. eds.), vol. 120:7-17 (1985).

Shirley, M.W., et al., Eimeria spp. from the Chicken: from Merozoites to Oocysts in Embryonated Eggs, *Parasitology*, vol. 83:259-267 (1981).

Smith, N.C., et al., Maternal transmission of immunity to *Eimeria maxima*: western blot analysis of protective antibodies induced by infection, *Infection & Immunity*, 62(11): 4811-4817 (1994).

Song et al., Antibodies to the α-Subunit of Insulin Receptor from Eggs of Immunized Hens, *The Journal of Immunology*, vol. 135:3354-3359 (1986).

Stotish, R.L., et al., Preparation and Purification of Merozoites of *Eimeria tenella*, *The Journal of Parasitology*, vol. 61(4):700-703 (1975).

Wallach, M., et al., *Eimeria maxima*: Identification of Gametocyte Protein Antigens, *Experimental Parasitology*, vol. 68 (1):49-56 (1989).

Wallach, M., et al., Passive Immunization of chickens against *Eimeria maxima* Infection with a Monoclonal Antibody Developed against a Gametocyte Antigen, *Infection and Immunity*, vol. 58:557-562 (1990).

Wallach, M., et al., *Eimeria maxima* gametocyte antigens: potential use in a subunit maternal vaccine against coccidiosis in chickens, *Vaccine*, vol. 13:347-354 (1995); and.

Wallach, M., et al., Progress Towards a Subunit Vaccine Against Coccidiosis, *Misset's World Poultry, Supplement Coccidiosis*, No. 2:22-24(1996).

Supplementary European Search Report issued Jun. 16, 2005 in connection with European Application No. 02 746 870.1.

Belli, S.I., et al., Cloning And Characterization Of The 82 kDa Tyrosine-Rich Sexual Stage Glycoprotein, GAM82, and Its Role In Oocyst Wall Formation In The Apicomplexan Parasite, *Eimeria maxima*, Gene, vol. 307:201-212, (2003).

Belli, S. I., et al., Roles Of Tyrosine-Rich Precursor Gycoproteins And Dityrosine- and 3,4-Dihydroxyphenylalanine-Mediated Protein Cross-Linking In Development Of The Oocyst Wall In The Coccidian Parasite *Eimeria maxima*, *Eukaryotic Cell*, vol. 2:456-464 (2003).

Belli, S.I. et al. (2002) Functional Genomics of *gam*56: Characterisation of the role of 56 Kilodalton Sexual Stage Antigen in Oocysi Wall Formation in *Eimeria maxima*, *Int. J. of Parasitology* 32:1727-1737.

Tomley, F.M. et al. (2001) EtMIC4: a Microneme Protein from *Eimeria tenella* that Contains Tandem Arrays of Epidermal Growth Faactor-like Repeats and Thrombospondin Type-I Repeats, *Int. J. of Parasitology* 31:1303-1310.

Wallach, M. et al. (1992) Maternal Immunization with Gametocyte Antigens as a Means of Providing Protective Immunity Against *Eimeria maxima* in Chickens, *Infection and Immunity* 60(5):2036-2039.

Witcombe, D.M. et al. (2003) Molecular Characterisation of EmTFP250: A Novel Member of the TRAP Protein Family in *Eimeria maxima*, *Int. J. of Parasitology* 33:691-702; and.

Database EMBL mic4 Gene, (2001) XP002313642, Abstract.

* cited by examiner

FIGURE 2
kDa  pH 4⟶ 7
160 —
75 —
50 —
35 —
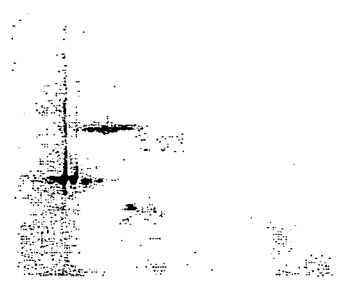
Immunoblot
(anti-APGA)
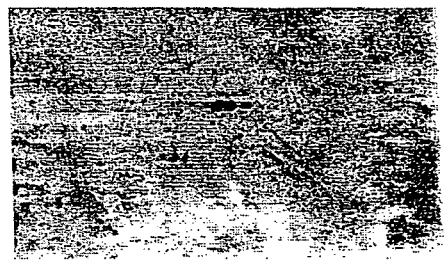
Silver stain

FIGURE 4A

Sequence Range: 1 to 1754

```
          10        20        30        40        50        60        70
AGCAGAACATAGGGAGTTCATCTGTTCCTTCTTTTCATCATTTATTCCTCGTTTCTCACCGTTTTATTTT
TCGTCTTGTATCCCTCAAGTAGACAAGGAAGAAAAGTAGTAAATAAGGAGCAAAGAGTGGCAAAATAAAA 80        90       100       110       120       130       140
TTTTGTGTAACCCTCTCCGCTGTTGAGTCCCAATGACCCGCCTCGGCCTCGCTGCTGTCGCGCTGGCTCT
AAAACACATTGGGAGAGGCGACAACTCAGGGTTACTGGGCGGAGCCGGAGCGACGACAGCGCGACCGAGA
                                M    T    R    L    G    L    A    A    V    A    L    A    L>
                                      predicted initiator methionine 150       160       170       180       190       200       210
CGCCGTGGGCCCTTCCATGGCAGTGCCCAGCACCACTCCTGTGGAGAATCAGGTTCACCCTTACAGCGAG
GCGGCACCCGGGAAGGTACCGTCACGGGTCGTGGTGAGGACACCTCTTAGTCCAAGTGGGAATGTCGCTC
 A    V    G    P    S    M    A    V    P    S    T    T    P    V    E    N    Q    V    H    P    Y    S    E>
                predicted signal peptide cleavage site                                    amino terminus 220       230       240       250       260       270       280
ATGAGTACCTACCAGGAGGGGAGTGCCCCGGGGGCTCCGGAGGACACCACCACCACCACTACGTCGTCCC
TACTCATGGATGGTCCTCCCCTCACGGGGCCCCCGAGGCCTCCTGTGGTGGTGGTGGTGATGCAGCAGGG
 M    S    T    Y    Q    E    G    S    A    P    G    A    P    E    D    T    T    T    T    T    T    S    S>

290       300       310       320       330       340       350
CTGTTTCCGATGGAGCCGAGCAGTGGCTTGAGAGCTTTGTTCGTGCTGTGCAGCGCCAGCTGCAGCTTCA
GACAAAGGCTACCTCGGCTCGTCACCGAACTCTCGAAACAAGCACGACACGTCGCGGTCGACGTCGAAGT
 P    V    S    D    G    A    E    Q    W    L    E    S    F    V    R    A    V    Q    R    Q    L    Q    L    Q>
                                                                                             tryptic peptide sb56c 360       370       380       390       400       410       420
GGACCAAATGATGCGTCAGCTCATGAGGGACATTCAGGAGTACCTGAGCACTGCGTTCAACTGGGCAGAG
CCTGGTTTACTACGCAGTCGAGTACTCCCTGTAAGTCCTCATGGACTCGTGACGCAAGTTGACCCGTCTC
      D    Q    M    M    R    Q    L    M    R    D    I    Q    E    Y    L    S    T    A    F    N    W    A    E>
                                                                                       tryptic peptide sb56fc 430       440       450       460       470       480       490
AACCAGTCTACTGCCTACACCCGTGTTACCGAGATGATGGACATGATCTCCAACAGAATGAATGCAGCAA
TTGGTCAGATGACGGATGTGGGCACAATGGCTCTACTACCTGTACTAGAGGTTGTCTTACTTACGTCGTT
      N    Q    S    T    A    Y    T    R    V    T    E    M    M    D    M    I    S    N    R    M    N    A    A>
                                                                               tryptic peptide sb56h
```

FIGURE 4B

```
         500        510        520        530        540        550        560
TGGACAGCTCAAACGAACTCATGACCACTAGCGACACCACAGACCCCGAGACCCTCCGCCGTGCAACTCG
ACCTGTCGAGTTTGCTTGAGTACTGGTGATCGCTGTGGTGTCTGGGGCTCTGGGAGGCGGCACGTTGAGC
 M  D  S  S  N  E  L  M  T  T  S  D  T  T  D  P  E  T  L  R  R  A  T  R>

570        580        590        600        610        620        630
CAAGTACATGAAGGAGGTTCGCGTTCAGGACGTCCTGGTAGATGCTCTCTGGGCCTCTCTCCGCGGTGTA
GTTCATGTACTTCCTCCAAGCGCAAGTCCTGCAGGACCATCTACGAGAGACCCGGAGAGAGGCGCCACAT
  K  Y  M  K  E  V  R  V  Q  D  V  L  V  D  A  L  W  A  S  L  R  G  V>
                         tryptic peptide sb56a 640        650        660        670        680        690        700
CAGACAGCTGCCTGGATGAATGGAGTGACCGCTATTGAGAAGGAGGAGACGACTCCCATGGCTAGCCGCG
GTCTGTCGACGGACCTACTTACCTCACTGGCGATAACTCTTCCTCCTCTGCTGAGGGTACCGATCGGCGC
  Q  T  A  A  W  M  N  G  V  T  A  I  E  K  E  E  T  T  P  M  A  S  R>
               tryptic peptide sb56g 710        720        730        740        750        760        770
CTGCTGAGGAGTTCCTCCACCGCATGTACCATAACCTGAGGGCAGCAGGTATGTCTGAAGAAGATGTTGC
GACGACTCCTCAAGGAGGTGGCGTACATGGTATTGGACTCCCGTCGTCCATACAGACTTCTTCTACAACG
  A  A  E  E  F  L  H  R  M  Y  H  N  L  R  A  A  G  M  S  E  E  D  V  A>
tryptic peptide sb56d 780        790        800        810        820        830        840
CAAGTTCATCCCTAGAGCCGAGTACAACCCCTCCGAGCAGTCAAGAAATATGGGCAGAAAGGGCAGGAGC
GTTCAAGTAGGGATCTCGGCTCATGTTGGGGAGGCTCGTCAGTTCTTTATACCCGTCTTTCCCGTCCTCG
   K  F  I  P  R  A  E  Y  N  P  S  E  Q  S  R  N  M  G  R  K  G  R  S>

850        860        870        880        890        900        910
TTCTACTACGGCGGCTATCCCAGCTACTACAACTCCCCCTACTACAGCTACAGCAGCTACCCCAGCTACT
AAGATGATGCCGCCGATAGGGTCGATGATGTTGAGGGGGATGATGTCGATGTCGTCGATGGGGTCGATGA
   F  Y  Y  G  G  Y  P  S  Y  Y  N  S  P  Y  Y  S  S  Y  P  S  Y>

920        930        940        950        960        970        980
ACAACTACAGCTACCCGTCATACAGCTACAGCAGCTACCCCAGCTACTACCGCTACAGCAGCTACCCCTA
TGTTGATGTCGATGGGCAGTATGTCGATGTCGTCGATGGGGTCGATGATGGCGATGTCGTCGATGGGGAT
   Y  N  Y  S  Y  P  S  Y  S  Y  S  S  Y  P  S  Y  Y  R  Y  S  S  Y  P  Y>

990       1000       1010       1020       1030       1040       1050
CTACAACTACAGCTATCCCAGCTACTACAACTACGGCAGCTACCCCTACTACAGTTATAGCAGCTACCCC
GATGTTGATGTCGATAGGGTCGATGATGTTGATGCCGTCGATGGGGATGATGTCAATATCGTCGATGGGG
   Y  N  Y  S  Y  P  S  Y  Y  N  Y  G  S  Y  P  Y  Y  S  Y  S  S  Y  P>

1060       1070       1080       1090       1100       1110       1120
AGCTGGTACTGGCGCCGTCTCCGCTCTTTGGCAACAGCAACTTGCCCAGACTGCCCTCCTCTCACCACTC
TCGACCATGACCGCGGCAGAGGCGAGAAACCGTTGTCGTTGAACGGGTCTGACGGGAGGAGAGTGGTGAG
   S  W  Y  W  R  R  L  R  S  L  A  T  A  T  C  P  D  C  P  P  L  T  T>
```

FIGURE 4C

```
       1130      1140      1150      1160      1170      1180      1190
CCAGCATGATCCCAACTCCCCCCCCAATGATGAACATGATGAACACCCCACCCCCCATGGCAAACATGAT
GGTCGTACTAGGGTTGAGGGGGGGGTTACTACTTGTACTACTTGTGGGGTGGGGGGTACCGTTTGTACTA
 P  S  M  I  P  T  P  P  P  M  M  N  M  M  N  T  P  P  P  M  A  N  M  M>

1200      1210      1220      1230      1240      1250      1260
GACCAGCATGATGATGAACACTCCCATGGTTCCTCCTCCCCGCACCCTCGGAACTGAAGCCATGAGCCTC
CTGGTCGTACTACTACTTGTGAGGGTACCAAGGAGGAGGGGCGTGGGAGCCTTGACTTCGGTACTCGGAG
    T  S  M  M  M  N  T  P  M  V  P  P  P  R  T  L  G  T  E  A  M  S  L>

1270      1280      1290      1300      1310      1320      1330
GGCTTGGCCCCCATCGGTATCACCGGCGCCCCCATGACAGGTTTCGGTGTTCCTCCTGAGTTCGGTCCCT
CCGAACCGGGGGTAGCCATAGTGGCCGCGGGGGTACTGTCCAAAGCCACAAGGAGGACTCAAGCCAGGGA
 G  L  A  P  I  G  I  T  G  A  P  M  T  G  F  G  V  P  P  E  F  G  P>

1340      1350      1360      1370      1380      1390      1400
TTGGAGCCGAAGGTATCGGCCTCCCCACCGATGCCCTCGGCAGCACCCCCGAAATGACACCATTCGACCC
AACCTCGGCTTCCATAGCCGGAGGGGTGGCTACGGGAGCCGTCGTGGGGCTTTACTGTGGTAAGCTGGG
 F  G  A  E  G  I  G  L  P  T  D  A  L  G  S  T  P  E  M  T  P  F  D  P>
                                  Biotech Aus. tryptic peptide 1410      1420      1430      1440      1450      1460      1470
AACTACCCCCTACAGAACTCTCGCCCCCATGGACCTCCCCCCCATCCCCCCTCCTGTCTTCCCTGAAACC
TTGATGGGGATGTCTTGAGAGCGGGGGTACCTGGAGGGGGGGTAGGGGGGAGGACAGAAGGGACTTTGG
    T  T  P  Y  R  T  L  A  P  M  D  L  P  P  I  P  P  P  V  F  P  E  T>

1480      1490      1500      1510      1520      1530      1540
CCTATGAGGCCACCTACTCCCTTCGGCTTCGGACCTGCACCTGTTCCTCCCATGCCCTTCTAAACGACCT
GGATACTCCGGTGGATGAGGGAAGCCGAAGCCTGGACGTGGACAAGGAGGGTACGGGAAGATTTGCTGGA
 P  M  R  P  P  T  P  F  G  F  G  P  A  P  V  P  P  M  P  F  *
                                                           stop 1550      1560      1570      1580      1590      1600      1610
ACCATCCCTCAATCCATAGCTCACATTTCGTAGCCTCAAAACAGTTTTTTGTTCATTTCACTTCCAGGAC
TGGTAGGGAGTTAGGTATCGAGTGTAAAGCATCGGAGTTTTGTCAAAAAACAAGTAAAGTGAAGGTCCTG 1620      1630      1640      1650      1660      1670      1680
TCATGCTGCGACATTTGCATTCGTACCTCGAAACCGTCAACCTCAAACCCCAAACCATTCTGTGACCTCC
AGTACGACGCTGTAAACGTAAGCATGGAGCTTTGGCAGTTGGAGTTTGGGGTTTGGTAAGACACTGGAGG 1690      1700      1710      1720      1730      1740      1750
CCTCGCAAACGCGGAAGGCGGAACATTTTTTCTGAAGTATATTACTACGTTAAAAAAAAAAAAAAAAAAA
GGAGCGTTTGCGCCTTCCGCCTTGTAAAAAAGACTTCATATAATGATGCAATTTTTTTTTTTTTTTTTTT

AAAA
TTTT
```

FIGURE 5A

Sequence Range: 1 to 2145

```
         10        20        30        40        50        60        70
ATACAAATCCTTTTTATCTGGTTCCAACACGCTCACTCAACCACCACCTGGACACACCCTCCCCATACAT
TATGTTTAGGAAAAATAGACCAAGGTTGTGCGAGTGAGTTGGTGGTGGACCTGTGTGGGAGGGGTATGTA 80        90       100       110       120       130       140
ACAGGAGCAGCAGCAACACCAGCATCAAGATGACGCGTGCGGCAGCGCTTGCCGGGGTTTTGGCCCTGGC
TGTCCTCGTCGTCGTTGTGGTCGTAGTTCTACTGCGCACGCCGTCGCGAACGGCCCCAAAACCGGGACCG
                                  M  T  R  A  A  A  L  A  G  V  L  A  A>
                            predicted initiator methionine 150       160       170       180       190       200       210
TGCAGCAGGCAGCAGCCTTGCTCTACCTACTGTATTGGACACAACGACTGGCACCCAAGTGGAGTGGACT
ACGTCGTCCGTCGTCGGAACGAGATGGATGACATAACCTGTGTTGCTGACCGTGGGTTCACCTCACCTGA
 A  A  G  S  S  L  A  L  P  T  V  L  D  T  T  T  G  T  Q  V  E  W  T>
      predicted signal peptide cleavage site                amino terminus 220       230       240       250       260       270       280
GAGACCCCCTTAGACACAACAGAGGTAACTATGGGGGAGATGGGCAGCACCACCAGCGGCACGACTCCAA
CTCTGGGGGAATCTGTGTTGTCTCCATTGATACCCCCTCTACCCGTCGTGGTGGTCGCCGTGCTGAGGTT
 E  T  P  L  D  T  T  E  V  T  M  G  E  M  G  S  T  T  S  G  T  T  P>

290       300       310       320       330       340       350
CCAGCACTGGTGTGCGAATGATGGAGGCTGAAACTACAACCCCATCAACCCCTGAGGCTCCCCAGCAGCA
GGTCGTGACCACACGCTTACTACCTCCGACTTTGATGTTGGGGTAGTTGGGGACTCCGAGGGGTCGTCGT
 T  S  T  G  V  R  M  M  E  A  E  T  T  T  P  S  T  P  E  A  P  Q  Q>

360       370       380       390       400       410       420
GCAGCAGATGCCTCAGCCTCAACCTCAGCCACAGCAAACAACTCCCGTTCCTGAGGCCGTATTAGAGGCA
CGTCGTCTACGGAGTCGGAGTTGGAGTCGGTGTCGTTTGTTGAGGGCAAGGACTCCGGCATAATCTCCGT
 Q  Q  M  P  Q  P  Q  P  Q  P  Q  Q  T  T  P  V  P  E  A  V  L  E  A>

430       440       450       460       470       480       490
ATTATGCAAGAAATGCAAAATATTTTCCGTTCTTCTCTTGTACCAGGTTGGGATACTGTCGGTACAGCAG
TAATACGTTCTTTACGTTTTATAAAAGGCAAGAAGAGAACATGGTCCAACCCTATGACAGCCATGTCGTC
  I  M  Q  E  M  Q  N  I  F  R  S  S  L  V  P  G  W  D  T  V  G  T  A>
```

FIGURE 5B

```
         500        510        520        530        540        550        560
CAGATGCTGTACGTCAGATTGTAACCCGTGTAAGAGAACGTCTTACAGGACCATTAATGATGACAGAGAT
GTCTACGACATGCAGTCTAACATTGGGCACATTCTCTTGCAGAATGTCCTGGTAATTACTACTGTCTCTA
  A  D  A  V  R  Q  I  V  T  R  V  R  E  R  L  T  G  P  L  M  M  T  E  M>

570        580        590        600        610        620        630
GGATACTGGTCTTGGTAGAACAGGACCTTTATCAACCACAGGTGCAACAGGAGCAACAACAGGTCCTGTT
CCTATGACCAGAACCATCTTGTCCTGGAAATAGTTGGTGTCCACGTTGTCCTCGTTGTTGTCCAGGACAA
     D  T  G  L  G  R  T  G  P  L  S  T  T  G  A  T  G  A  T  T  G  P  V>
                                               tryptic peptide 82c 640        650        660        670        680        690        700
GCTGCATTACGCGGTGTAACAAATGATTTCCTTAGGGAAATAATGATTCAAGAAGCAGTACTTGAGACAT
CGACGTAATGCGCCACATTGTTTACTAAAGGAATCCCTTTATTACTAAGTTCTTCGTCATGAACTCTGTA
     A  A  L  R  G  V  T  N  D  F  L  R  E  I  M  I  Q  E  A  V  L  E  T>

710        720        730        740        750        760        770
TATGGGCAGTTGTACGTGATGCACAAGAAAGACCATGGCTAGTTAATGAACAGGAAGTATTGCATGCAGT
ATACCCGTCAACATGCACTACGTGTTCTTTCTGGTACCGATCAATTACTTGTCCTTCATAACGTACGTCA
  L  W  A  V  V  R  D  A  Q  E  R  P  W  L  V  N  E  Q  E  V  L  H  A  V>

780        790        800        810        820        830        840
AACAGCAGATGCTGTACAAGGTTTCCTTGGTCGCATGCATGATCGTCTTCGTGCAACAGGTTTCTCTGAG
TTGTCGTCTACGACATGTTCCAAAGGAACCAGCGTACGTACTAGCAGAAGCACGTTGTCCAAAGAGACTC
     T  A  D  A  V  Q  G  F  L  G  R  M  H  D  R  L  R  A  T  G  F  S  E>
                                                        tryptic peptide 82a 850        860        870        880        890        900        910
GAAGAAGTCATGAGACTTCTACCTAGGTCACGTAATGGTGGTTGTACCCGTACAGGGGGGCCTCTTTGATC
CTTCTTCAGTACTCTGAAGATGGATCCAGTGCATTACCACCAACATGGGCATGTCCCCCGGAGAAACTAG
  E  E  V  M  R  L  L  P  R  S  R  N  G  G  C  T  R  T  G  G  L  F  D>
                                                        tryptic peptide 82b 920        930        940        950        960        970        980
AATGTAACGATGCCCCTCCCTCTCGTCTTCTTGGTAAGAGGATGTATAGTACTGGATATTATGGTTATGG
TTACATTGCTACGGGGAGGGAGAGCAGAAGAACCATTCTCCTACATATCATGACCTATAATACCAATACC
  Q  C  N  D  A  P  P  S  R  L  L  G  K  R  M  Y  S  T  G  Y  Y  G  Y  G>

990       1000       1010       1020       1030       1040       1050
ATATCCTTCTTATTATAGCTATGGATATAGTTATCCAGCTTATTCACATTATCCTGTTTCTTATCCTTAC
TATAGGAAGAATAATATCGATACCTATATCAATAGGTCGAATAAGTGTAATAGGACAAAGAATAGGAATG
  Y  P  S  Y  Y  S  Y  G  Y  S  Y  P  A  Y  S  H  Y  P  V  S  Y  P  Y>

1060       1070       1080       1090       1100       1110       1120
TATGGGTATAGCTGGGGCCCCTCATACTACTATGGCAGCGGATACTATGGTAAACATGGATATAAGTACG
ATACCCATATCGACCCCGGGGAGTATGATGATACCGTCGCCTATGATACCATTTGTACCTATATTCATGC
  Y  G  Y  S  W  G  P  S  Y  Y  Y  G  S  G  Y  Y  G  K  H  G  Y  K  Y>
```

FIGURE 5C

```
        1130       1140       1150       1160       1170       1180       1190
GACATTATTACAGGAGACTTGCTGAGCAGGAACCAAGACCTGTTATGCCTCCTGCAGCAGCAACTGCCGC
CTGTAATAATGTCCTCTGAACGACTCGTCCTTGGTTCTGGACAATACGGAGGACGTCGTCGTTGACGGCG
 G  H  Y  Y  R  R  L  A  E  Q  E  P  R  P  V  M  P  P  A  A  A  T  A  A>
                              tryptic peptide 82f 1200       1210       1220       1230       1240       1250       1260
AGCAAACCTAAGAGCAGCAGCAGCAGCAGCAGCAGAAGTACCACCACCACCACCACCAGCAGCAGTACCA
TCGTTTGGATTCTCGTCGTCGTCGTCGTCGTCGTCTTCATGGTGGTGGTGGTGGTGGTCGTCGTCATGGT
 A  N  L  R  A  A  A  A  A  A  A  E  V  P  P  P  P  P  P  A  A  V  P>

1270       1280       1290       1300       1310       1320       1330
CCACCACCACCAGCAGCAGCAGCAGGTACCCCAGCTATGATGCCTCCTCCTATGATGGGTGTTGAAGAAC
GGTGGTGGTGGTCGTCGTCGTCGTCCATGGGGTCGATACTACGGAGGAGGATACTACCCACAACTTCTTG
 P  P  P  P  A  A  A  A  G  T  P  A  M  M  P  P  P  M  M  G  V  E  E>

1340       1350       1360       1370       1380       1390       1400
CTGTTCCTTTCCGCTCCCTCTATCCTAGCTATAGCTGGAGTTATCCAGCATATACTCGCGTGTCTCCCTC
GACAAGGAAAGGCGAGGGAGATAGGATCGATATCGACCTCAATAGGTCGTATATGAGCGCACAGAGGGAG
 P  V  P  F  R  S  L  Y  P  S  Y  S  W  S  Y  P  A  Y  T  R  V  S  P  S>

1410       1420       1430       1440       1450       1460       1470
TTATTCTTATTATACACCCTCTTATAGTTCTTCTTACTATTATCCCCGTTATAATTATGCCTATAACTAT
AATAAGAATAATATGTGGGAGAATATCAAGAAGAATGATAATAGGGGCAATATTAATACGGATATTGATA
 Y  S  Y  Y  T  P  S  Y  S  S  S  Y  Y  Y  P  R  Y  N  Y  A  Y  N  Y>

1480       1490       1500       1510       1520       1530       1540
CCCTTATATTCAGACTATAGCTGGTATGATTATAGCTACCCCCTTGCCTACAGCAGCTATAGTAGCTACC
GGGAATATAAGTCTGATATCGACCATACTAATATCGATGGGGGAACGGATGTCGTCGATATCATCGATGG
 P  L  Y  S  D  Y  S  W  Y  D  Y  S  Y  P  L  A  Y  S  S  Y  S  S  Y>

1550       1560       1570       1580       1590       1600       1610
CCCTTTCCTATAGTAGCTATAGCTACCCCCTTAGCTATACCTACCCTAGTGCCTTTTATAGAAGACTAGA
GGGAAAGGATATCATCGATATCGATGGGGGAATCGATATGGATGGGATCACGGAAAATATCTTCTGATCT
 P  L  S  Y  S  S  Y  S  Y  P  L  S  Y  T  Y  P  S  A  F  Y  R  R  L  E>

1620       1630       1640       1650       1660       1670       1680
GGTCCCTGATCTAACAACAACTACTACTACTCATCATGAGCAGCAGCAGCAGCAGCAGCAAGAAAGTACA
CCAGGGACTAGATTGTTGTTGATGATGATGAGTAGTACTCGTCGTCGTCGTCGTCGTTCTTTCATGT
 V  P  D  L  T  T  T  T  T  T  H  H  E  Q  Q  Q  Q  Q  Q  E  S  T>

1690       1700       1710       1720       1730       1740       1750
ACTACTGCTGTACCTACAGAAACCATTACTACTCCCTCTACTCGTAATACACACAGCAGCAGCCTAAGAA
TGATGACGACATGGATGTCTTTGGTAATGATGAGGGAGATGAGCATTATGTGTGTCGTCGTCGGATTCTT
 T  T  A  V  P  T  E  T  I  T  T  P  S  T  R  N  T  H  S  S  S  L  R>
```

FIGURE 5D

```
           1760       1770       1780       1790       1800       1810       1820
     GAGTAGGAGAAAGATATGAGCCTATTACCCCTACACAAAGAACTTTTTATAATAATACAGAAGGTACTAA
     CTCATCCTCTTTCTATACTCGGATAATGGGGATGTGTTTCTTGAAAAATATTATTATGTCTTCCATGATT
      R  V  G  E  R  Y  E  P  I  T  P  T  Q  R  T  F  Y  N  N  T  E  G  T  N>
                                                       Biotech Aus. tryptic peptide 1830       1840       1850       1860       1870       1880       1890
     CAACCCTGTCTATACACCCGAAAATCTTACAGAAGATGAACCACAAACTGTATGGGAAACATACAACTAA
     GTTGGGACAGATATGTGGGCTTTTAGAATGTCTTCTACTTGGTGTTTGACATACCCTTTGTATGTTGATT
      N  P  V  Y  T  P  E  N  L  T  E  D  E  P  Q  T  V  W  E  T  Y  N  *>
                                                                             stop 1900       1910       1920       1930       1940       1950       1960
     ACCCTAAACCCTAAACCCTAAACCCTCAACCCTAACATTTCTCATTTTTTTATAGAGAAATTTTAGGGAA
     TGGGATTTGGGATTTGGGATTTGGGAGTTGGGATTGTAAAGAGTAAAAAAATATCTCTTTAAAATCCCTT 1970       1980       1990       2000       2010       2020       2030
     CACTAACCTGCCTGCCTTGCCATCGTTTATATATATCCATTTGTTTATTAATAAACAATTTTTATTTACC
     GTGATTGGACGGACGGAACGGTAGCAAATATATATAGGTAAACAAATAATTATTTGTTAAAAATAAATGG 2040       2050       2060       2070       2080       2090       2100
     TCTAGTCGTCTTTTTATTAACAGCGCTTATTCGCGTTGTTTATACAAACTACTACTATTTTTACCCAATA
     AGATCAGCAGAAAAATAATTGTCGCGAATAAGCGCAACAAATATGTTTGATGATGATAAAAATGGGTTAT 2110       2120       2130       2140
     ATACTTGTACAGGCATTTTTTAAAAAAAAAAAAAAAAAAAAAAAA
     TATGAACATGTCCGTAAAAAAATTTTTTTTTTTTTTTTTTTTTTTT
```

FIGURE 9
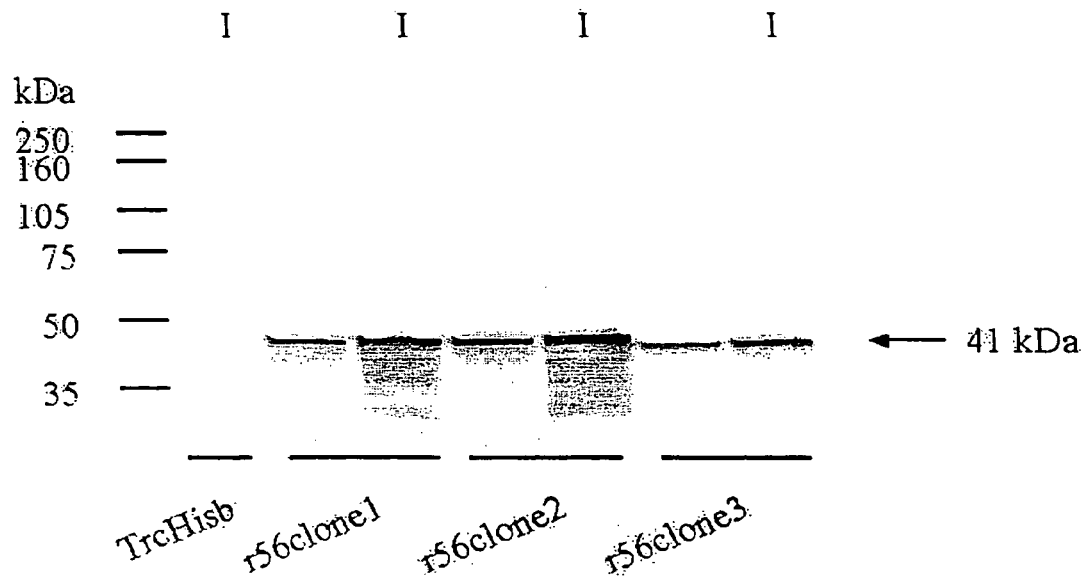
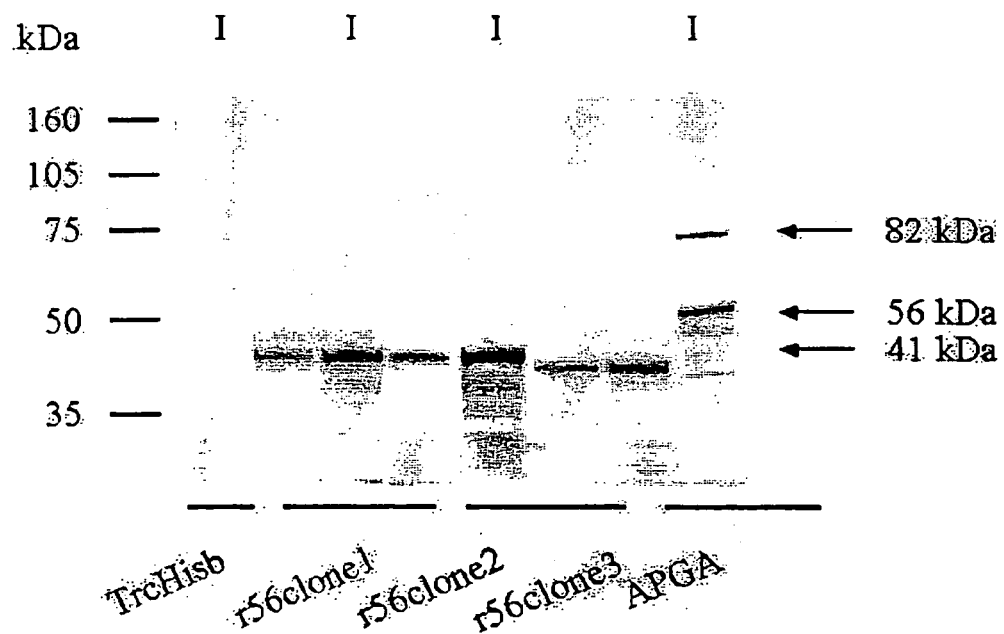

FIGURE 12A

```
230    1 ATGCTGCATCGCAACCCGCGGTGGGCGCTTTGTGCAGCCCTCGCTGCACT    50
WO 9   1                                                         0

230   51 CTATGGCGGAACAGGAATCGCCAGCGCCGAAGTTAACAATGAATTGAGCA   100
WO 9   1                                                         0

230  101 AGTGCGAATCTGGGTGGACACCCTGGACTACCTGCAACCCGCAAACTGGT   150
WO 9   1                                                         0

230  151 CTGCGGGAGAGGCACAATGCACAGTGCGAGACATGGGTGGAGGTTGAGGA   200
WO 9   1                                                         0

230  201 ATGCCAGAAGCTGACAGGATGTGGCAACTGGACTCCTTGGTCTCCCGGCG   250
WO 9   1                                                         0

230  251 ATATGTCGTGTGTGGTGGGACAGTTTCAAACCCGCAACAGGGAGGGCTGC   300
WO 9   1                                                         0

230  301 CCAGAGGTGCAGGAAGTGAGGGCATGCAGGCCTGTACTTCTAGAATCCAA   350
WO 9   1                                                         0

230  351 CGATCAATGGACCCCCTGGACAATGTGCGACACCAACCGCGTCCAGGAAA   400
WO 9   1                                                         0

230  401 GATACAACTCAAAGTGCGGACCCGTCGAAGTCCGCGAGTGCAACATGGAC   450
WO 9   1                                                 ATG     3
```

FIGURE 12B

```
230    451  GACGCAGAGATCGAGAAATGCGGCGAGTTCGTGGAATGGGATGCCCCTAT   500
WO 9     4  GGTTTTTTCGTCTTCACAGGCGGTGATTTGGCGACTGGAGCCCCCCTCT    53
              *     **   * * ****  **  ****  **  ***    ****** *

230    501  GAATGGAGACTGCGTACGGGGGGGTACCCACACGCGTTACCGTCAAAACT   550
WO 9    54  CCCTGGTGACTGCGTGCCTGGCACTACTCACACAGGCCAGAGGGCAAATT  103
              ***  ********  *   **   ***  *****  **  *   *   *** *

230    551  GCCCAGACCGCAAAGAGGTGCGGGTCTGCGGAGCCTTTGATTGCAGTAGC   600
WO 9   104  GCCCAAACCACAAGGAGGTGCGGGTTTCGGCGCCTTCGATTGTAGCCAG   153
              *****  ***  ***  ******;******  *****  *****  ****  **

230    601  TGCTCTGTAAACGCCACTTGCGATCCCATTGGTGCATCCTGCGAATGCAA   650
WO 9   154  TGCTCAGTCAACGCTACCTGCGACCCCTCGGAGCCACTTGTCAGTGCAA   203
              *****  **  *****  **  *****  ***  *  ** **    * **   *****

230    651  GCCTGGTTTCCGCGGCAATGGGAAGAACCTGCGAGGCCTTCAACCCCTGCG   700
WO 9   204  ACCGGGTTTCCGAGGCGATGGGACTCAGTGCGAGGCATTCAACCCTTGCG   253
              **  ********  ***   *******            **********  ****

230    701  AAGATACCCCTGCACCTTGCGACAGCAACGCCATCTGCACCCCAGACGCA   750
WO 9   254  AAGGCGAGACGGCTCCTTGTGATGCGAACGCGACCTGCACGGCTGATGGA   303
              ***    *  **  *****  **  *****   * ****** *    ** * *

230    751  A-TGACGCCAAATGCCAGTGCAAGGCAGGCTGGGACGCAGATTCCGGAGC   799
WO 9   304  AATGACGCCAAATGCCACTGCAACAAGGGCTGGAACGCAGACAGCAAGGC   353
              * ****************  ****  ****      *****    **    **

230    800  AGGCAGCAGCAAGAAGCCTTGCGTTGAGGTCGACGAGTGCGCATCCAACA   849
WO 9   354  AGGTGCCAGCGGTCACGCATGCGTGGAGGAGGACGAATGCGCCAACAACA   403
              ***  ****  *  *  *****  ****  *****  *****    *****

230    850  CCCACCAGTGCCCGGCACACTCCACATGCATCAACACCAAGGGCTCTTAT   899
WO 9   404  CGCACGAATGTCCGCAGCACTCAACTTGCGTCAACACTGAGGGCTCCTAT   453
              *  *** *  **  ***   *****  **  ***  *******   *******   ***

230    900  AAGTGCGACTGCAACCAGGGATACCGTCAAGGGAGAGGACGGACAGTGTC   949
WO 9   454  GAATGCAACTGCTTACCGGGTTATCAG-AAGGATCAGGATGGGAAATGCC   502
              * ***  *****   *  **  ** *   ****    ****  ** *  **  *

230    950  ATGACGTCGATGAATGCACCAACGGAGAGCACACCTGCCCCGCTCACTCC   999
WO 9   503  AGGACATAGACGAGTGCGCT---GGGGAACATGGTTGTCCCGCACACTCG   549
              * ***  *  **  **   ***  *        **  **  **  *****  *****

230   1000  ACTTGTTTGAATACAGCTGGCAGCTACGAGTGCCGCTGCGACACTGGGTA  1049
WO 9   550  ACTTGCGTGAACACGGCAGGCAGCTTCGAGTGCAAGTGCGACGCCGGTTT   599
              *****  ****  **  **  *******  ********   ******  *  **  *

230   1050  CAGCGGAAATGCAACTGCAGACAGCCCTTGCAAGAACATTGACGAATGCG  1099
WO 9   600  CAGTGGCAGTGCTACTTCTGAGAGTCCTTGCTCGAATATAGACGAGTGCC   649
              ***  **  *  ***  ***  **  **  ** ******   ***  **  *****   ***

230   1100  CCAACCCCAACGGCTGCCTGGCCAACGCTATCTGCACAGACACCGACGC  1149
WO 9   650  AAGACCCGGATGCCTGCTCAGCCAACGCAATCTGCGCAGACACTGAGGGC   699
              ****  *  *******  *******    *****   *****  *****   ***

230   1150  TCCTTCACCTGCAGCTGCCCCGAAGGGTACAGCGGCCAGGGAACCCATGA  1199
```

FIGURE 12C

```
WO 9    700  TCTTTCACTTGCAGCTGCCCTGAGGGGTTACAGCGGTGGGGGATCACACGA  749
             ** *****  ***********  ** **  ********    ****  *  ** **

230    1200  CTCTCCCTGCTCCAAGATCGACTTCTGCGCATACCCCTCACTCAATACAT  1249
WO 9    750  CTCTCCTTGCTCGAAGATAGATTACTGCGCGACCCCACACTGAACACCT   799
             ******  ***** **** **  **  ******  ***** ****  ** ** *

230    1250  GCGGAGCCCACTCCACTTGC---AACACCCTCACATCTTTCAAGTGCATC  1296
WO 9    800  GCGGGGCCCACTCGACTTGTGTGAACACACTAACGACGTTCAAGTGCGTT  849
             **** ********  *****       *****  ** **  * ********* *

230    1297  TGCGATGCGGGATATGAAGGCGCCGGCACTGGCGAGAGCCCGTGCGTGGA  1346
WO 9    850  TGCGATGCCGGTTATGACGGCGCGGGAACGCACGAGAGCCCTTGTGTGGA   899
             ********  **  *****  **** ** **  * ********  **  *****

230    1347  CGTGAACGAGTGCTCGAACGAGAAGCCCACAAACAACTGCAACAGAAACG  1396
WO 9    900  TATCGACGAGTGCTCCAAGGAGAAACCATCCAATGACTGCAACCGAAACG   949
              * ********** ** ***** ** * **  ********  ******

230    1397  CAAACTGCACCAACACCGAGGGATCCTACACTTGCGAATGCAAGCCCGGT  1446
WO 9    950  CCGTTTGCACAAATACTGAGGGATCGTACACCTGCGCATGCAAGGAAGGC   999
              *   ***** ** **  ********  ***** ****  ******* **

230    1447  TTCTCTGGCGACGGCATGGGTCCCAACGGGTGTACCGACATCGACGAGTG  1496
WO 9   1000  TTCTCTGGCGAGGGTTTCGGAGCTGCAGGGTGTGCAGATGTCGATGAGTG  1049
             **********  ** *  **  *     ******  *  ****  *****

230    1497  CGCGGCGGAGCAGTCCCCCTGCGACCCTCACGCCTCCTGCAGCAACACTG  1546
WO 9   1050  CGCGA------ATTCGCCCTGCGACGCCCACGCCTCTTGTGCCAACACCG  1093
             ****        *  ** ********  **********  ** ****** *

230    1547  AGGGCTCGTATGTATGCACCTGCAACACCGGCTACGAGCCAGCTTCAACC  1596
WO 9   1094  AGGGTTCCTACGTTTGCACTTGCAACCCTGGCTATGAACCAGCCTCAAGC  1143
             ****  **  **  ** ***** ******  *  ***** ** ***** **** *

230    1597  GACGGGCATGCATGCAAAGATATCGACGAGTGCGCCACCGGTGCAGCTGG  1646
WO 9   1144  GACGGACATGCATGCAAGGACGTTGACGAGTGTGCAGCGGGCACGGCGGA  1193
             *****  ***********  *  * ********  **  *  *  ** *

230    1647  GTGCCACGTGTCAGCACAGTGTCTGAACACGGACGGCAGCTACGAGTGCA  1696
WO 9   1194  ATGCCACGTCTCCGCACAGTGTGTGAACGTGGATGGCAGCTATGAATGCC  1243
              ********  **  ********  ****  ***  ********  ** ***

230    1697  AGTGTCTTGAGGGCTTCGTCGGCGACGGAAAGACCTGCAACGACGTCGAT  1746
WO 9   1244  ACTGCTTGGAAGGTTTCATTGGCGACGGAAAGGTGTGCAGTGACGTTGAC  1293
              * **  * ** **  ** *** * ***************  ****  ***** **

230    1747  GAGTGCGCTGCGGCGACATCTCCTTGCGGTGACAACACTCACTGCCAGAA  1796
WO 9   1294  GAGTGTGCGGCTGAGGCTTCGCCCTGTGGCGCAAACACGCATTGCCTGAA  1343
             *****  ** **  *  *  *  ** **  **  *****  ** ****  ***

230    1797  CACAATTGGCAGCTACGAGTGCGAGTGCAAGGCTGGCTATGGCAACATGC  1846
WO 9   1344  CACCATCGGCAGCTACGAGTGCGAGTGCAAGGACGGATATGGCCACATGG  1393
             ***  ** ****************************  ** ****** *****

230    1847  AAGACAACGCATGCAGCGACATTGACGAGTGCAAGGATGCGAACACCAAG  1896
WO 9   1394  AGGGCAACGCGTGCAGCGACATCGATGAGTGCTCAGAGGCGTCTACAGAG  1443
```

FIGURE 12D

```
                  *  *  ******  *********  **  ******    **  ***   **  **
230   1897  ATCCCTGACAACTGTCTTTGCGTGAACAATGATGGCAGCTACTCCCTTGA  1946
WO 9  1444  ATCCCAGAGAACTGCAACTGTGTCAACACCCAGGGGAGCTTCTCCCTTGA  1493
            *****  **  *****        **  **  ****    **  **  ****  *********

230   1947  GGCGAAGCCTGGATACGAATTGGTGAACGGCGAGTGCATCAAGATCGACT  1996
WO 9  1494  GGCAAAGCCTGGGTACGAGCTCCTCGACGGCAAGTCCGTCAAGATCGACT  1543
            ***  ***  ****  *****  *  **    *****  *****  *************

230   1997  TCTGCGCCCGCGGCGCATGCAACTCGCTGGCCTCCTGCAAGGAGAATCAA  2046
WO 9  1544  TCTGCGCCCGTGGTGCATGCAACTCGCTGGCGCACTGCAAGGAGAATCCC  1593
            *********  **  ***************  ****  ************  ****

230   2047  GAAGGCACAGCGGCGATCTGCACCTGCCTGCCAGGCTACAGCGGCGACGG  2096
WO 9  1594  GAGGGCACCGCGGCGATCTGCACTTGCATAGCTGGCTATTCAGGTGACGG  1643
            **  *****  ************  ***  *  *  *****    **  *****

230   2097  CACTGCTGAAGGCCACTGCAACGACATTGACGAGTGTGCAGGTCAGAATG  2146
WO 9  1644  CACAGCTCAGGGCCACTGCGATGACATCGATGAGTGCTTGCGGAGAAATG  1693
            ***  ***  *  *********  *  *****  **  *****       *  ******

230   2147  ACTGTGCTCCTGCCGAGCAGGGAGGCATCTGCGAGAACACTGTCGGCTCG  2196
WO 9  1694  ACTGCACCCCTGCCGATCAAGGAGGGATTTGCGAGAACACTCGCGGCTCT  1743
            ****    *  ********  **  *****  **  ************  ********

230   2197  TACACCTGCAAGTGCAAAGAGGGGTACAGGCAAGATGGAAACTCATGCAC  2246
WO 9  1744  TACACCTGCAAATGCGCAGCTGGGTACCAGCAAGACGGCAACTCATGCAC  1793
            ***********  ***    **  ******  ******  **  **************

230   2247  TGAGATCGACGAGTGCGCTGAGGGAACCCACAACTGCCACCCTTCCGCCA  2296
WO 9  1794  TGACATTGACGAGTGCGCCAACGGCACTCACAACTGCCATGCCTCCGCGG  1843
            ***  **  **********  *  **  **  *************  *  *****  *

230   2297  CCTGCAGCAACACCCCCGGAAGCTTCACCTGCCAATGCAACAGTGGATTC  2346
WO 9  1844  CATGCACGAACACGCAAGGCTCCTTTGAGTGCGCCTGCAACGCAGGCTTC  1893
            *  ****  *****  *  **  ***    ***  *****    **  ***

230   2347  ACTGGCAGCGGTGTGGAGTGCCAAGACATTGACGAGTGCTCAACTGACGC  2396
WO 9  1894  AGCGGCAACGGGGTTGAATGCAACGACGTCGACGAGTGCTCGACTGACGC  1943
            *  ****  ***  **  **  **  *  ***  *  **************  *****  **

230   2397  AGATGATTGTGGTGCAAACACCATCTGCAGCAACACCATTGGTGCTTTCG  2446
WO 9  1944  TGACGATTGCGGAGAGAACACACTGTGCAACAACACAGTTGGCAGCTTCG  1993
            **  ******  **  *  *****    ****  *****  ****    ****

230   2447  AGTGCAACTGCCGTGAAGGCTATGAACGCGCAGACGCAAAGACCTGCGTC  2496
WO 9  1994  AGTGCACATGCATGGCTGGCTTCGAGGCCGGGGACGCGAAGACCTGCAAA  2043
            ******  ***  *  ****    **  ***  *****  *****  ***

230   2497  GACATCGACGAATGCGCGACAGGCACACACACTTGCTCGAACCACGCCAC  2546
WO 9  2044  GACATCGACGAATGTGCAAGCGGGACCACACTTGCTCCACCCACGGGAC  2093
            ************  **  *    **  **  *********  *  ******  **

230   2547  CTGCACCAATACCGATGGGTCATTCACATGCCAGTGCAACCCCGGCTTCG  2596
WO 9  2094  ATGCACCAACACTGCTGGGTCGTTCACATGTGAGTCCAACCCAGGCTTTG  2143
            *******  **  *  ******  ********    *********  *****  *
```

FIGURE 12E

```
230   2597 AAGGTGACGGCCACAAGTGCGAGGACATCGACTTCTGCGGTGCTGGACAG 2646
WO 9  2144 ACGGTGACGGCCACAAGTGCGAGGACGTGGACTTCTGCGGCCAGGGGCTG 2193
           *  *********************  *  **********    **  *  *

230   2647 CACGACTGCAATGTGCATGCCGAGTGCTCTGAGAGCGAGGACAACACCAC 2696
WO 9  2194 CACGACTGCAACGTGCATGCAGAGTGCTCGGAAAGCGACGACAACACCAC 2243
           ***********  ******** ******* ** ***** ***********

230   2697 TTTCAAGTGCACCTGTATAACAGGGTACGCTGGAGACGGCCATGGCGAGG 2746
WO 9  2244 CTTCAAGTGCACCTGCGGCATTGGGTACAGCGGGGAAGGCCACGGGGAGA 2293
            **************    ***  ****** * ***  ****  ** * *

230   2747 CAGGCTGCCAAGACATTGATGAGTGCGCAGAAGAAAACATCTGCGGAAGC 2796
WO 9  2294 ATGGTTGCCAAGACATTGATGAGTGCGCCAAGATGCCATCTGTGGGGAG  2343
            *  ***********************    *****  ***  ** *

230   2797 AACGCTGTCTGCACAAACACCGCAGGAAGCTACCAATGCGCATGCCGTGA 2846
WO 9  2344 AACACAGTGTGTACCAACACACCAGGTAGCTTTGAATGTGCGTGTGTGGA 2393
           ***  * ** ** ** *****  ****  ****   *****  **    **

230   2847 GGGCTTCGTTGCATCAGCTGAACAGCAGCAGCAGGGAACCCAGCACTGG  2896
WO 9  2394 AGGGTTCGTGG---CTGTGGGAGCGAAGCTCAAGGGAGCAACTTCATTGA 2440
            * *****  *      *  *     *   ***  **** *  **  **

230   2897 TTTGCGTGGACGTCGACGAGTGCAGCGACGCTTCGAAGAACACATGTGCC 2946
WO 9  2441 CCTGCATAGACATCGATGAATGCAACGACGCCTCGAAAAACACTTGCGCC 2490
            ** *  ****    * **  ****  *****  ****  ****  ***

230   2947 AAGCCAGCCGACGGAGGCATTTGCACAAACACTGAAGGCAGCTACGAATG 2996
WO 9  2491 ACGTCAGCTGACGGAGGCTCTTGCAAGAACACCGCAGGCAGCTATGAGTG 2540
           *  * **** ********   ****   ****   * ******** ** **

230   2997 CGCTTGCAAGCCAGGCTACCAAGGTGACGGCCACAGCTGCGCAGACATCA 3046
WO 9  2541 CTGTGTTTGCCTGGGTTCCAGGGGCGACGCCCACAGCTGCACAGATATTG 2590
           *  *   **  *    ** **  * ****  ********* **** **

230   3047 ACGAATGCACTGCACAGGGCACCTGCGGCGAACACACAACTTGCAAGAAC 3096
WO 9  2591 ATGAGTGCGCCACCCAAGGCGTATGCGGGAACATGCGACCTGCGAAAAC  2640
           * ** ***  *  *  * **      ***** *****  * **  * ***

230   3097 ACACCCGGATCCTTCCAGTGCGACTGCCGTTGAGGGATTCG---AGCGCGC 3143
WO 9  2641 ACTGCGGGTTCGTACAATTGCACCTGCGAGGCGGGTTACACTCAGCAAGA 2690
           **  * ** **  *  * *** *****   *   ** *   *       *

230   3144 TGATGAACGCACCTGCCCGTGACATCAACGAGTGCGAGACAGGAGCAGTGG 3193
WO 9  2691 TGGGCCCGTCGGCTGCATTGATATTGATGAGTGTGCAGCCTCCACAGCAG 2740
           **  *  *  *  ***   **  **   **  **  *  *    *    *

230   3194 TGCTGCCACCGAACTCCACCTGCGTCAACACTGAAGGCAGCTACGACTTC 3243
WO 9  2741 TGTTACCCGCCAACGCCACTTGCGTGAACACTGAAGGCAGCTATGACATTC 2790
           **  *  **  *** ****  ****  **************** ***

230   3244 GACTGCGTTGCTGGGTACCGCCGCACTGATGGAGCTTGTGTGAAGATCGA 3293
WO 9  2791 GAATGCGTGCCCGGCTACCGCCATACGGAGAATGGCTGTACCAAGATTGA 2840
           **  *****  *  *  ******* *** *  *   **   ***** **
```

FIGURE 12F

```
230  3294 CTTCTGCAAGGAGAAGGGATGCAACGCAAACGCCACATGCCGGGAAAACG 3343
WO 9 2841 TTTCTGCAGCGAAAAGGGATGCAATGCGAATGCCAGCTGCAAGGAGAACG 2890
          ****** ** ********** ** ** **** *** ** ****

230  3344 ATGCCGGCACCGAGGCCATCTGCACTTGCAAGGAAGGCTATGAAGGCAGC 3393
WO 9 2891 ATGCCGGCACCGAAGCCATCTGCACCTGCCACAGCGGGTACGAGGGCAAT 2940
          **** ******* ************ *** *  ** ** ** ****

230  3394 GGAGAAGGCGAAGATGGTTGCCAGAACATCAATGAGTGCGAGAGAGGCGA 3443
WO 9 2941 GGCGAAGGAGAAGAAGGGTGCAAAAACATTGAGGAGTGCTCCGTGGGAGA 2990
          ** ***** ***** ** *** * ***** * ****** ** **

230  3444 ACCCTGCAAGGACTTCGGCGAAGGCGGTGTTTGCGTCGACACACCAGGAT 3493
WO 9 2991 GCCATGCAAAGACTTCGGCGACGCGGGCGTCTGTGTCGATTCTCCGGGAT 3040
          ** ****** ********** *  ** **    ** ***   * ** ****

230  3494 CATTCACTTGCGAGTGCGCTGCTGGATTCATTCAACGCCGCTCCGTTTGC 3543
WO 9 3041 CCTTCAGCTGCTCTTGCGCCACCGGTTTTATCAAGAGCCGATCTACTTGC 3090
          * ****  *** **** * ** ** ** * * *  ** ** ** ****

230  3544 CAAGATGTTGACGAATGTCTCGACGGAAAGCTGAACACCTGCGCTGCCAC 3593
WO 9 3091 CAGGACATAGATGAGTGCCTCGACGGAAAGATGAACACTTGCGCCCCCGT 3140
          ** ** * ** ** ** ** ************ ****** ***** **

230  3594 CGGAGGCGTCTGCTCCAACACCGTCGGTTCCTTCACCTGCTGGTGCGCCA 3643
WO 9 3141 CGGGGGTATCTGCACGAACACCGTCGGCTCCTTCACCTGCTCTTGCGCTG 3190
          *** **  ***** * ***********  ****************** ****

230  3644 GCGGCTTCGAAGGCGATGGCCACACCTGCAATGATGTCGACGAATGCGCA 3693
WO 9 3191 CTGGCTTCACGGGTGACGGCCTTACTTGCGAGGACATCGACGAATGTGCT 3240
          ****** ** ** **** ** *** * ** ************ **

230  3694 ACAGCACAGCACACCTGTGACCCGAATGCCACTTGCGTCAACACCGAAGG 3743
WO 9 3241 ACGGCGGCACACACGTGCCGACCCAACGCCACCTGTGTCAACACTGTCGG 3290
          ** **  ***** ** ***** ** ***** ** ********  * **

230  3744 CAGCTTCGAGTGCGCGCTGCAATGCCGGATTCGAGGGCGAGGAGACACCT 3793
WO 9 3291 CAGCTTCGAATGCGGATGCAAGGAGGGATTCTCTGGTGACGGCACACAT 3340
          ********* *** * ****  * ******  ** ***** ***** *

230  3794 GCGCAGACATCGACGAATGCGCAGACCCAGCCAAAAACACATGCGATACA 3843
WO 9 3341 GCACCGATATCGACGAATGCGCTGACCCTAACCTTAACAAATGCGACACA 3390
          ** * ** ************** ***** *    ****  ****** ***

230  3844 CACAAGGGTGTATGCCAAAACACCACAGGGTCCTACACCTGCGGCTGCAA 3893
WO 9 3391 CACAAGGGCATCTGCCAGAACGGCACTGGATCCTACACTTGCGGATGCAG 3440
          ******** * ***** *** * *** ** ******* ***** *****

230  3894 GACCGGATTCAGTCTTGCAGCTGACGGAAGCACATGCGAAACGTCGACG 3943
WO 9 3441 GCCTGGATACAGTCTCTGCGGCGCACGGCTTCACTTGCGACAATGTCGATG 3490
          *  ****  *****  ** ** ** *****  *****  ** ***** *

230  3944 AGTGCGCGGCGGGAACTGCAAACTGCAACGAGCGAAGCTTCTGTAAGGAC 3993
WO 9 3491 AGTGCGCTGCCGGGACGGCCACTTGCGGAGAGCGCAGCTTCTGCCGTGGAC 3540
          ******* ** ** ** ** **  **** **** ********   ****

230  3994 ACAGAGGGTTCCTACCAATGCGAGTGCAAGAACGGCTACAAGGCTGCAGC 4043
```

FIGURE 12G

```
WO 9  3541  ACGCAAGGGTCATACAAGTGCGAGTGCAAGAACGGCTACCGCCAGTCTGG  3590
            ** * ** ** *** * ***************        * **

230   4044  AGAGGACTGTGTGGACGTTGACGAGTCCGAGCCTGGCGTGCATGGATGCA  4093
WO 9  3591  GGAGGACTGCGTGGACGTTGACGAGTGCGAGCCTGATGTGCACACATGCA  3640
            ******  *************************  ****    *****

230   4094  GCGAGCACGCAATCTGCCACAAATACAGACCGCAGCTACTCCTGCGAATGC  4143
WO 9  3641  GCGAGCACGCTACGTGCACGAACACTGAGGGGAGCCACACCTGCACCTGC  3690
            **********  *  *****  **  **  ***  **  *****   ***

230   4144  ATGGAGGGATACCAGGGAGACGGCAAGGCTTGCGAGAAGACAGTCGGCGT  4193
WO 9  3691  AATGAAGGGTACCAGGGAGACGGAAAGAAGTGCGAGAAGACAGTGGGCCC  3740
            *  ** **  ************  *** *** ************ ***

230   4194  CTGCGACTCCGCTCCCTGCGGTGCCCACGCCACCTGCGAGCCTGCAGGGG  4243
WO 9  3741  TTGCGACAACTCGCCATGCGGCAACAACGCCATGTGTGAAGCTACTGCCG  3790
            ******  * * **  *****  *  *****  *  **  ** * * *

230   4244  ACAACTACACTTGCACATGCCACCCAGGCTACGAGATGCGCGAAGGAGCC  4293
WO 9  3791  ATAGCTACAACTGCCACTTGCAAAGCTGGCTACGAGATGAAGGACGGGCC  3840
            *  ***** *****  *** ***  *  ************  ***  **

230   4294  TGCGTTGACATCGATGAGTGCACAGCCAGGCAGCCTCAACTGCGACCCTCA  4343
WO 9  3841  TCTGTCGACATCGATGAGTGCCAGTCGGGCACCCACAACTGCGACCCGCA  3890
            *  **  ************  *  ** **  *  ** ************  **

230   4344  TGCCATTTGCACAAACACCGACGGCTCCTTCACTTGCGTCTGTGGCAGCG  4393
WO 9  3891  TGCTGACTGCAGCAACACCGATGGATCCTTCACGTGCACGTGCGGTTCTG  3940
            ***   ****  ********  ** ********  *  **  ** **

230   4394  GCTATACCGGCCTTGGCACATCCTGCGAAGACATCGACGAGTGCGCGGGT  4443
WO 9  3941  GCTACACTGGTGTGGGTACCCTTTGCGAGGATGTGGACGAGTGCGCGGGC  3990
            ****  ** ** **  *  **  *****  *  *  *************

230   4444  AACGCAGCAGGCTGCGACATCCACGCCGTCTGCACGAACACTCCCGGATC  4493
WO 9  3991  AACCATGCGGGCTGTGACATCAACGCTGTTTGCACTAACGTCCCTGGCTC  4040
            ***   **  *****  *****  ****  ** *****  ** ** ** **

230   4494  GTTCAAGTGCGACGTGCAAGAGCGGCTTCGAAGGCGATGGCACGCAATGCA  4543
WO 9  4041  GTTCACTTGCGAGTGCAAGAGTGGCTTCGAAGGCGATGGCACGAGTGTA  4090
            *****  ***********  **************        * ** *

230   4544  CGGAGAAGGTGTTGCTCCCCGGACAGATTCACTGCGAAGCCTGGACTGCA  4593
WO 9  4091  CGGAGAAAGTGCTGCTCCCTGGCCAGATTCACTGCGATTCGTGGACTGCA  4140
            ******* *** *******  ** ************* *  *  *******

230   4594  TGGACAGAGTGTACCGACGGCGCCAAAACCAGCACACGCAGCTGCCTTGC  4643
WO 9  4141  TGCACCGAATGTACAGCTGAAACTAAGCAGAGCACCCGCAAGTGCGTGGC  4190
            **  ** ** *****  *   *   *  *****  ***  ***  **

230   4644  ACTGCCGCTTAAGAAGGAGATCCGCGCCTGCCCTGCAGCTGACTTCTCCC  4693
WO 9  4191  TCTTCCTCTCAAGGTCGAGGTGAAGCTTTGCCCCGATGCTGACATTTCAG  4240
            ** ** ** ***  *** **   *****  *  ***** * **

230   4694  AGTGCGGAGAGTTCACTGAATGGACTGCCTGCCCTGGAACCAACAATAAC  4743
WO 9  4241  CCTGCGGTGAACTCGGCGAGTGGTCATCATGCCCAGGAGTTGACAACAAC  4290
```

FIGURE 12H

```
              ++++* ++   ++   ++ +++ +   +  +++++ +++     ++++ +++
230   4744  CTGTCTCATAGGCGCCACTGAAAGATTCGGAGAACCGGATGCGAAGATGC  4793
WO 9  4291  CTGTCGCACCGCAGAGCAGAGAAGTTCGGGAGCCGGGCTGTGAGCACGC   4340
              +++++ ++    +    + ++ +   +++++ ++ ++ ++ ++ ++    + ++

230   4794  AGAGGAAGTCCGCGAATGCCCAGATGAAGAGACCGAGCAGAAATGCGGCG  4843
WO 9  4341  TGAGGAGGTCAGGGAGTGCCCAGATGAAGAAGTTGAGGAGCGCTGTGGTG  4390
              +++++ +++ +  ++  ++++++++++++++    +++ ++   ++ ++ +

230   4844  CCTGGGGTGAGTGGACCGCCTGCGGCGACCCATCCCTGGCCTGAGAACT   4893
WO 9  4391  CCTTTGGCGAGTGCACTCCATGCGGCGATCCTTCTGAGGGCTTGAGGACC   4440
              +++  ++ +++++++++ ++ ++++++++ ++ ++      +++ ++++ ++.

230   4894  CGCGCACGCGAGAACTGCCCCGATGTGGTAGAGTTCGAGCGTTGCACTAT  4943
WO 9  4441  AGGACGCGCCAGAACTGCCCAGAAGAGGCAGAATTCGAGCACTGCACAAT  4490
                +  + +++ ++++++++++ ++  +  ++ +++ +++++++   +++++ ++

230   4944  GCCCAGTGAGCCTCAGGCTGGCGAAGTGACTGAGCCTCACACAGAAGGAG  4993
WO 9  4491  GCCCTCTGCACCATCCGTTCCCGAGGGCGGCAGCAGCTGCACAGAGTTCG  4540
              ++++ ++  ++     + +  +++ +                 ++++++    +

230   4994  GAGCCGGAGTTGCTGGCGAAGTGACTGAGCCTGACACGGAAGAAGGAGCC  5043
WO 9  4541  GGGCCTGGAGTCAATGCG---TGGCTGACGCT--CATGGGATCAAGATGC  4585
              + +++ +    ++   +++    ++ ++++ ++  ++ ++ +  +  ++ +

230   5044  GGAGTTGGTGGTGAAGTGCAGCCCGGGTACAGAAGAAGGAGCAGGAGTTGG  5093
WO 9  4586  AGCACAGAACGTGC-GTACACAATGAAGCTGTGCAGGAACACAGAATCTG  4634
               +      +    +++ ++ ++       +   + +    + +  ++ +  +

230   5094  TGGTGAAGTGCAGCCCCGGTACAGAAGAAGGAGCCGGAGTTGGTGGTGAAG  5143
WO 9  4635  CACCGTGGAAGA-TCCACAACAGTGCGGGGAGTGGTCGCAGTGGTCAGAG  4683
               +    +  +  +   ++   ++++   ++++ +    +  +           ++

230   5144  TGCA-GCCCCGGTACAGAAGAAGGAGCCGGAGTTGGTGGTGAAGTGCAGCC  5192
WO 9  4684  TGCAAGAATGGCAAGCAGTACAGAGGCGCCGGCCGG-----ATGCGCGTCT  4728
              ++++ +    ++ +    +   +++ ++ + +   ++        + ++ +

230   5193  CGGTACGGAAGAAGGAGCCGGCATTCGTGGCGAAGTGACTGAGCCTGACA  5242
WO 9  4729  GTGTACG-AAGTCAGAGCCTGCAGCGCCG------------------CTAGCG  4762
              +++++ +++   +++++ +++ ++  ++ +                       ++ +

230   5243  CCGAAGGAGGAGCCGGCAGTTAGTG-GCGAACCGACCGAAGAAGAGGGCAC 5291
WO 9  4763  ATGCGAAAGAAATGCTCTTTTGGTGCGTGGAGCGGCTGCGTGGTGGAGTTT  4812
                +   ++ +    +   ++ +++ + + + +  ++ + +             ++ ++

230   5292  CGAAAGCACCGGTCCATGCAAAGAGTTCGGACCCTGGACGGCCTGCAAGG  5341
WO 9  4813  GGCGGTCAC------ACTTACAAAGTGCGAAACTCAATCGAC-TGCGAGC  4855
               +        +++     +   +  +++ ++ + +           ++ + +++ ++

230   5342  AGGACGAGAACGGAGTCGGCATCCAACGCCGTATGTGCGCCGGCAGAGAA  5391
WO 9  4856  TCAGTGAGCT-----GCAGGCTTGCAA-GCC----GAGCGCCGCACCGAG  4896
                +++     +     +   +  ++++ +++      + ++++++ ++    ++

230   5392  GACATCATCGAATCCAGAATTTGCACTCTCACGGATGACTGCGGAGAATG  5441
WO 9  4897  GGCGAGGGCAAGTGCGCTGCTTGGAGCCCCTGCACGATCTGCAGGGA--C  4944
                  +    + + +       +++  +         +    + +  ++++ + ++
```

FIGURE 12I

```
230  5442  GACCCCCTGGTCAACTTGCACTAACGGCAGCCAGGCCAGAAACAAACGCT  5491
WO 9 4945  GGCATGCAGACTCGCGACTGCAAAAGCCTCGGTGTTCAGGAGTCC-CGCC  4993
              *  *  *        *   *  **  ***   *   ***  *       ***

230  5492  TCTGCACCAACGTIAGGGAAGTCCGTCTCTGCGGAGCTGACATTCCAGTT  5541
WO 9 4994  CATGCTCAGCTGAAGGAGAGACCGATTCTTGCGGAGCCTTTGGACCC-TT  5042
              ***  *      *   *  **    *    ********        **  **

230  5542  ACAGACGGATGCACGTGGAGCGAGTGGACTTCTTGCAGTCTAGTCAATGA  5591
WO 9 5043  CGAGCCGGCAGCTTGCAAGGCTGCCGAGATGGTCACGA---GGACGCGGG  5089
              **  ***  **  *    **  ***  *              *  *    *

230  5592  GGAGGGCGGCTACTTCCGCACGCGCACATCCTCTGACTGCAACATGAATG  5641
WO 9 5090  AGTGCAACGGTGCT-CAGCAGAAGGAAACC---AGACTGTGCAATCC-TG  5134
              *  *     *  **  **  ***  *  *  *      *****      **  **

230  5642  AAGTGCAGGCCTGCTCTCCCAGCAGCAGCACAACTGCAGACAGCGAAACA  5691
WO 9 5135  AGGGCAATGACAACTGCAACAACTGGGGTGCTTGGACAGAGTGCTCGCTA  5184
              *  *    *   *  *     **    **  *  *   *  *       ****  **       *

230  5692  GAAGGCACCTGCTCTGCATGGAACCCCTGGACGGAGTGCTCGAACGGCCA  5741
WO 9 5185  ATTGTGGGCGGCTCTGCCCTGCGGTCTCGCGAGGAGTCCACTTGCGGCTA  5234
              *     *  ******   *      *    *     *****  *  *    ****  *

230  5742  CCAGACACGCAAGTGTGCCACAATGGAAGCAGAAGAATCGCGCACTTGCG  5791
WO 9 5235  TGTGGA--GTTAGAGGAGTGCAGTGGCAGCAGCAGCAGCGGCGACCAGAC  5282
              *   *   **  *      **  ***  *****  **  *  **       **   *

230  5792  GAGAGACTCCAGAGAACTGCGGAGAATTCGGCCCCTTCGAACCCGCAAAC  5841
WO 9 5283  CGTCCACTGCCGGC-AGCTGGTCGGAGT---GCTCCATGAGAAAAACGGAG  5328
              ***  *  *  *  *   *  ***      **   *     **  **   *      *   *

230  5842  TGCACGGCCGGCCAAATGGTCACCAGGACGCGCACCTGCGGAGAAACCGA  5891
WO 9 5329  CGCACCTGTGATGTCCTCTCTGACGGATCCCACACCAGCGTTACTGAAGT  5378
              ****          *  .       *    *  *  *  *  ****  ***           *

230  5892  CCAGAAGGAAACCAAACTGTGCGACGTCAGCTCCACCGAAGAAGGAAAAC  5941
WO 9 5379  GCTCACCTGCGACGACGTGCTGCCTGACTCTTCGGTGAATTTGGCGAGT  5428
              **  *       *  *  **      *  *    **     *  *    ***   **  *

230  5942  AATGCGGTCAGTGGGGCCCATGGAGCGAATGCAACATCCACCTGGGCTCA  5991
WO 9 5429  GGTCCGAAT-GTAGCGCTGACGGCTTGCACTCGAGGTCCTGTCAGGCTG  5477
              *  **    **  **  **    *  **   *  *   *  *    ***      *   *

230  5992  GAGGACAATGTGCGTGTTCGTGAGG-ACACCGCTTGCGGCGTGACGGAGT  6040
WO 9 5478  CCCAGACGTAACTGAAGTGATGACTTGCGGCAGCGAAAACTGCCGGCTT  5527
                     *      *    *.  ***      *    *            *        ***  *

230  6041  ACGAGGAGTGCAGCAAGC-CGGCGAACAACGCCTTTGTCTGCACACCTTG  6089
WO 9 5528  TCGGCGAGTGGAGCGAGTGCGGCAGCCCAGAGGACGGCCTACGGTCGCGT  5577
              **  *****  ***  **   ****    *  *            *  **  *    *

230  6090  GAGTGAATGCTCGGACAAGAAGGAGCGGAGAACGTGCACCATCCGCAAAA  6139
WO 9 5578  CAGCGAACGAACTGCGAAGAGGGATCCGGCTGCATTTGC--TCCGAGACA  5625
              **  ***  *    *  *   ****  ***  *  *        *   *    *****  *  *
```

FIGURE 12J

```
230    6140  ACGGTCT-TGTTCAGACACGTCAAGAATTCAGAACATGCAGTGTAGACAT  6188
WO 9   5626  GAAGCCTGTGTTAACACTGAGCTCCACCCCATCCCATTGCCAGTTCCTGG  5675
              *  **  ****  *  **         *  *   **    ***     **

230    6189  CGCCACAACTTGCGGCGATTTCGGCGCA--TGGTCTGAATGCAACGCTGA  6236
WO 9   5676  CGGCGGCGAGGGCAGCGAGAACGGCGAGGGTGGCCAAACCGGAGAGGAGG  5725
              **  *       **  ****  *****    ***  *  *  *  *  *

230    6237  GGGCTTGCATCAGCGCAGTCT-CGAGAAATGCCCCGACGTCATCGAGGTC  6285
WO 9   5726  GAACGGAGGGAGGCGCAGGCGGTGCTGGAGGATCCGGTGGTGCTGAGGA-  5774
              *    *        *****.*     *   *   ***   *     ****

230    6286  GCAACTTGCGGCAGTGAGGATTGCCCGCCATTCGGCGAGTGGACTGAATG  6335
WO 9   5775  GCTGCC--CGGAGAAGAGCGTGGCGCAGGTGCCGGCGGAGAAGGAGGCTC  5822
              **  *     ***       *711   *  **  *      *****       *  *

230    6336  CGGCGTTCCAGAGGAGGGCATGCGTTCTCGCCAACGCATTGACTGCGTTG  6385
WO 9   5823  TGGCGGTAATGCTGAGGAGCTGC---CCGGAGAAGGGGGTGCTGGCG---  5866
              ****  *     *   ****    **      *   *   **  *   ***

230    6386  AATCTGCAGCCTGCCAGTGCACAGAAGTGGAGAGCTGCTTCGACACCGAA  6435
WO 9   5867  AAGCTGGAGGCT-CTGGCG-GTAGTGCTGAGGAGCTGC-------CCGGA  5907
              **  ***  **  **   *  *  *       **    **   *******        *** *

230    6436  TTGCACCCCATTCCAGCCCCCGGTACGGAAACAGGCGAAGGAGAGGGAGA  6485
WO 9   5908  GAAGAGGGCGGCGCAGGTGCCGGCGGAGGAGGAGGCTCTGGCGGTAGTGC  5957
              *     *     ***   ****     *  *  ****    **  *     *  *

230    6486  GACCGAGACAGGCGAAGGCGAAACTGGTGAAGCAGGTGGCGAGGAAGGCG  6535
WO 9   5958  TGAGGAGCTGCCTGGAGAAGAGGGCCGCGCAGGTGCCGGCGGAGAAGGAG  6007
              ***       *  **   **       **  *  **   *   ****   *****  *

230    6536  AGCAAACAGGAGAAGGCGAAGTGCAGCCCCCAGAAGAAGAGCTTCCTGGG  6585
WO 9   6008  GCTCTGGCGGCAATGCTGAGGAGCTGCCCGGAGAAGAGGGCGGCGCAGGT  6057
              **   *   *    **  *  **  ****  ******  *        *  **

230    6586  GAGAGTGTAACTGAGCCTGAG---GAGAAGCCTGAGGAGGAGCTACCTGA  6632
WO 9   6058  GCTGGAGGAGCCGAAGGCGAGACAGGGAAACCTGGCGGCGAAGAGGGTGG  6107
              *    *    *    *   **    ***    *  ***  ****   *  **       **

230    6633  GGAGGAGGTTACTGAGCCTGAGGAGAAGCCTGAGGAGGGTGTGACTCAGC  6682
WO 9   6108  CGCAGGCGGCGCTGGTGAGGGTGCTGGCGGTGAAGGTGGTGAGGTCCAGC  6157
              *  *   *   ***         *    *       ***  *  **** *    ****

230    6683  CTGAGGAGACACCTGAGCAGCCTGTTGAGGGTACCGAAGAAGAGGGCAAG  6732
WO 9   6158  CTGGAGAGGGAGAACGGGCGAGTGAAGGAGGCGAGCAAGTGCCGGAAACC  6207
              ***  ***    *    *  *   **  *   **         ***    **  *

230    6733  CAGGAG---TCTGAGGCTG---CCCCCGAAACT------CCTGCCGTCCA  6770
WO 9   6208  CCTGAGACACCCGAACCGGAAACACCTGAAGCTGAGAGACCTGAAGAGCA  6257
              *  ***     *  **  *  *   -*  **  ***  **         ****  *  **

230    6771  GCCAAAACCAGAGGA---GGGTCACGAACGCCCAGAACCCGAAGAGGAGG  6817
WO 9   6258  ACCTCCACCGAAACTCCAGCAGACCAGCCCACCCAAGGCGGTGCAGAAG  6307
              **     *  **      *   *  **  *  *  ***  **   *   **  *

230    6818  AGGACAAGAAGCAAGAAGGCGGCGGCTTCCCAACAGCTGCAGTGGCAGGA  6867
```

FIGURE 12K

```
WO 9  6308  AAGAGGAGAAGGAGGAGGGCAGCGGCTTCCCCACGGCAGCTGTTGCCGGA  6357
            *  ***  *******  **  ***  **********  **  **  **  **  **  ***

230    6868  GGTGTTGGTGGTGTGTTGCTCATAGCTGCTGTAGGTGGTGGTGTTGCAGC  6917
WO 9  6358  GGTGTAGGTGGTGTACTACTGCTGGCAGCAGTGGGTGGTGGCGTTGCCGC  6407
            *****  *******  *  **  *  **  **  **  ********  *****  **

230    6918  CTTCACTAGCGGCGGAGGTGGCGCTGGCGCACAGGAGGCAGAACAGGTCG  6967
WO 9  6408  GTACTCCGGTGGTGGTGGAGGTGGCGGTGCCGAGGAGGCTGAGCAAGTTG  6457
            *  *  *  *  **  **  **  **  *  **  **  ******  **  **  **  *

230    6968  AGTTCGAAGGAGAAGATACCGGAGCAGCAACTGCCGAGACACCTGAAGCC  7017
WO 9  6458  AGTTTGAAGGTCAAGAGTCGGGTGGTGCGTCTGCCGAAACACCTGAGGCT  6507
            ****  *****  *****  *  **  *  **  *******  *******  **

230    7018  GATACAGTTATCGACATCACAGACGAAGACGACTACTGGGCCGACAGCGG  7067
WO 9  6508  GATACTGTGATTGACATCACTGACGAAGACGACTACTGGGCAGACAGTGG  6557
            *****  **  **  ********  ********************  *****  **

230    7068  CGACATTCAG  7077
WO 9  6558  TGACATCCAG  6567
            *****  ***
```

FIGURE 13A

```
              10                    30                              50
5' GTG GTG ATT GAA TCT GCT CCA GCC AAG ATG GCT CAC CCT CCT GTG GTG ATT GAG TCT GCT
   Val Val Ile Glu Ser Ala Pro Ala Lys Met Ala His Pro Pro Val Val Ile Glu Ser Ala 70                    90                             110
   CCG GTC GAG GTG GTC CAT CCT CCT ATG GTG ATT GAA TCT GCT CCA CCC AAG ATG GCT CAA
   Pro Val Glu Val Val His Pro Pro Met Val Ile Glu Ser Ala Pro Pro Lys Met Ala Gln 130                   150                             170
   CCT CCG ATG GTG ATT GAG TCT GCT CCA CCC AAG ATG GCT CAA CCA CCT ATG GTG ATT GAG
   Pro Pro Met Val Ile Glu Ser Ala Pro Pro Lys Met Ala Gln Pro Pro Met Val Ile Glu 190                   210                             230
   TCG GCT CCC GTC GTC GAG GTG GTC CAT CCT CCT ATG GTG ATG GAA GCC GCT CCC ACC GTG AAG
   Ser Ala Pro Val Val Glu Val Val His Pro Pro Met Val Met Glu Ala Ala Pro Thr Val Lys

GGA AGA TAC CTC GCT GCT GAG GAT GAG GTG GAA GAG CAG TTT GAA TCG AAC AG 3'
   Gly Arg Tyr Leu Ala Ala Glu Asp Glu Val Glu Glu Gln Phe Glu Ser Asn
```

Nucleic acid sequence of the first 293 nucleotides of clone pEM 250/14. Note the presence of a 14 amino acid repetitive sequence in the single translated open reading frame.

FIGURE 13B

```
                  10                      30                        50
5' C CTG CAG GTT GTA CTA AGA GCG CTT TAT GAC TAT CGG GAG CTC AAA TGC GGC TCA GCA TGC
    Leu Gln Val Val Leu Arg Ala Leu Tyr Asp Tyr Arg Glu Leu Lys Cys Gly Ser Ala Cys 70                      90                       110
CGG AAC GTG GGC ATT TTG GTA CAC GGA GGT ATC ACC TCG AGC GAA TGG GCG GGG GTC TTT
Arg Asn Val Gly Ile Leu Val Hys Gly Gly Ile Thr Ser Ser Glu Trp Ala Gly Val Phe 130                     150                       170
CCG CAA ACA AGC GTT CCA CCA AAA CCT AAG GTG GAA AAC TGT TCA GTT GCA TTT AAT TAC
Pro Gln Thr Ser Val Pro Pro Lys Pro Lys Val Glu Asn Cys Ser Val Ala Phe Asn Tyr

190
GCT TTT GTA AAT ACC 3'
Ala Phe Val Asn Thr
```

Nucleic Acid sequence of the last 196 nucleotides of clone pEM 250/14. The single open reading frame is translated into the amino acid sequence shown below the nucleotide sequence. A potential N-linked glycosylation site (Asn-Cys-Ser) is underlined.

FIGURE 15

```
CGAATTGCACCCCATTCCAGCCCCCGGTACGGAAACAGGCGAAGGAGAGGGAGAGACCGAGACAGGCGAAGGCGAAACTGGTGAAG   6750
   E  L  H  P  I  P  A  P  G  T  E  T  G  E  G  E  G  E  T  E  T  G  E  G  E  T  G  E      2173

CAGGTGGCGAGGAAGGCGAGCAAACAGGAGAAGGCGAAGTGCAGCCCCCAGAAGAAGAGCTTCCTGGGGAGAGTGTAACTGAGCCTGAGG   6840
 A  G  G  E  E  G  E  Q  T  G  E  G  E  V  Q  P  P  E  E  E  L  P  G  E  S  V  T  E  P  E    2203

AGAAGCCTGAGGAGGAGCTACCTGAGGAGGAGGTTACTGAGCCTGAGGAGAAGCCTGAGGAGGGTGTGACTCAGCCTGAGGAGACACCTG   6930
 E  K  P  E  E  E  L  P  E  E  E  V  T  E  P  E  E  K  P  E  E  G  V  T  Q  P  E  E  T  P    2233

AGCAGCCTGTTGAGGGTACCGAAGAAGAGGGCAAGCAGGAGTCTGAGGCTGCCCCCGAAACTCCTGCCGTCCAGCCAAAACCAGAGGAGG   7020
 E  Q  P  V  E  G  T  E  E  E  G  K  Q  E  S  E  A  A  P  E  T  P  A  V  Q  P  K  P  E  E    2263

GTCACGAACGCCCAGAACCCGAAGAGGAGGAGGAGAAGAAGGAAGAAGGCGGCGGCTTCCCAACAGCTGCAGTGGCAGGAGGTGTTGGTG   7110
 G  H  E  R  P  E  P  E  E  E  E  K  K  E  E  G  G  G  F  P  T  A  A  V  A  G  G  V  G      2293

GTGTGTTGCTCATAGCTGCTGTAGGTGGTGGTGTTGCAGCCTTCACTAGCGGCGGAGGTGGCGCTGGCGCACAGGAGGCAGAACAGGTCG   7200
 G  V  L  L  I  A  A  V  G  G  G  V  A  A  F  T  S  G  G  G  G  A  G  A  Q  E  A  E  Q  V    2323

AGTTCGAAGGAGAAGATACCGGAGCAGCAACTGCCGAGACACCTGAAGCCGATACAGTTATCGACATCACAGACGAAGACGACTACTGGG   7290
 E  F  E  G  E  D  T  G  A  A  T  A  E  T  P  E  A  D  T  V  I  D  I  T  D  E  D  D  Y  W    2353

CCGACAGCGGCGACATTCAG
 A  D  S  G  D  I  Q
```

Figure 19
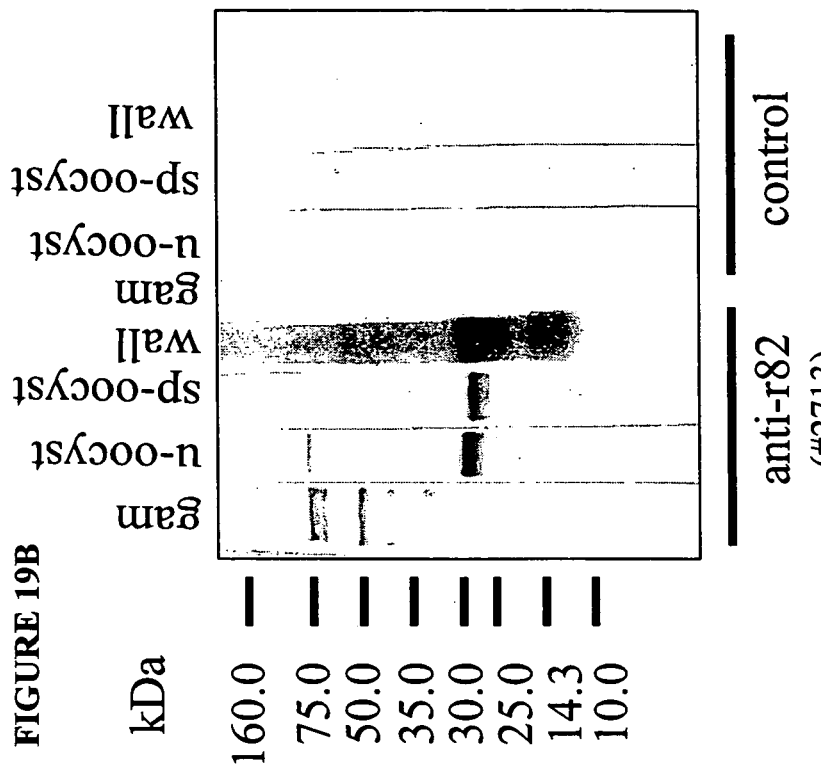
FIGURE 19B
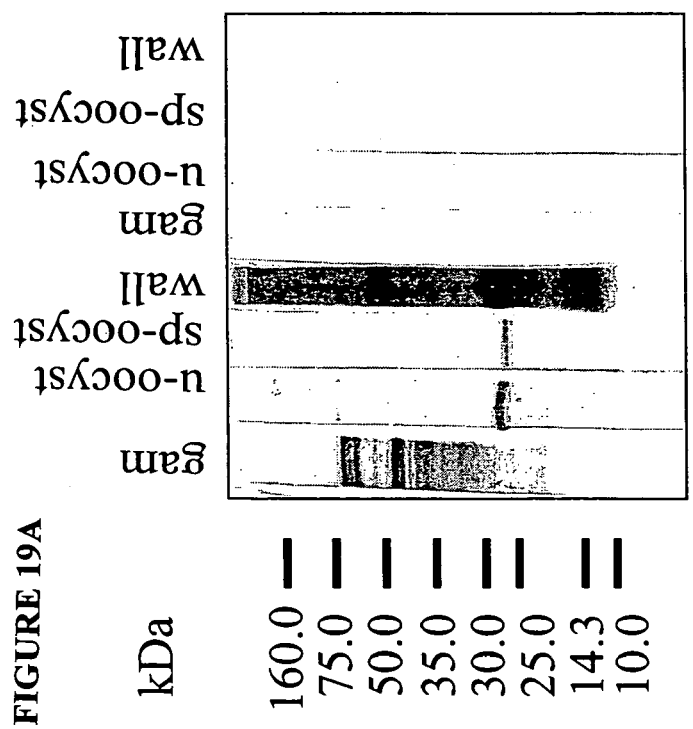
FIGURE 19A

FIGURE 20A

```
                                        21............35
56 kDa gametocyte protein (N-terminus)  VPSTTPVENQHVHPYS
~30 kDa oocyst wall protein             VPSTTPVENQH-HPYS
```
(this wall protein represents the low abundance protein recognized by anti-r56 kDa antibody)

```
                                   240..........254
56 kDa gametocyte protein (domain 1)  MGRKGRSFYYGGYPS
14.1 oocyst wall protein              YGRKGRSFYYGGYPS
                                                     G
```

FIGURE 20B

```
                                   418..........431
82 kDa gametocyte protein (domain 2)  YPSYSWSYPAYTRV
14.2 oocyst wall protein              YPSYS-SYPAYTRV 282...........296
82 kDa gametocyte protein (domain 1)  GKRMYSTGYYGYGYP
14.3 kDa oocyst wall protein          -KRMYSTGY-G---P
```

FIGURE 20C

```
30 kDa oocyst wall protein            -SFSPVAPQELF--(L)
```
(this protein represents the 30 kDa protein detected by coomassie blue staining of purified oocyst wall fragments)

NUCLEIC ACIDS ENCODING RECOMBINANT 56 AND 82 KDA ANTIGENS FROM GAMETOCYTES OF *EIMERIA MAXIMA* AND THEIR USES

This application is a §371 national stage of PCT International Application No. PCT/US02/21233, filed Jul. 3, 2002, designating the United States of America, which claims priority of U.S. provisional Application No. 60/303,699, filed Jul. 6, 2001, the contents of which are hereby incorporated by reference.

This application claims the benefit of U.S. Provisional Application No. 60/303,699, filed Jul. 6, 2001, the contents of which are hereby incorporated by reference into this application.

Throughout this application various publications are referenced in parenthesis. Full citations for these publications may be found listed in alphabetical order at the end of the specification immediately preceding the claims. The disclosures of these publications in their entireties are hereby incorporated by reference into this application in order to more fully describe the state of the art to which this invention pertains.

BACKGROUND OF THE INVENTION

The organisms which cause the disease known as "coccidiosis" in chickens belong to the phylum Apicomplexa, class Sporozoa, subclass Coccidia, order Eucoccidia, suborder Eimeriorina, family Eimeriidae, genus *Eimeria*. Within the *Eimerian* genus there are many species, several of which are pathogenic in chickens. The species of major concern to the chicken industry are *Eimeria tenella, Eimeria maxima, Eimeria acervulina, Eimeria necatrix* and *Eimeria brunetti*.

Coccidiosis has become a major economic problem in the chicken industry over the past several decades, mainly due to the overcrowding of chicken houses and the development of drug resistance by the parasite. The rearing of chickens under crowded conditions on a litter floor provides optimal conditions for the growth and spread of *Eimeria* parasites. Under such circumstances, sanitary control is impossible and the farmer must rely on the effectiveness of coccidiostat drugs. However, drugs must be kept in the feed at all times, shuttle programs must be used to avoid the appearance of drug resistance strains of *Eimeria*, and certain drugs have costly side effects. Furthermore, these coccidiostats also have antibacterial effects and therefore are considered to be in-feed antibiotics. Recently the European Union has decided to ban the use of all in-feed antibiotics in the chicken industry including anticoccidial drugs. Thus, the only viable approach to the control of coccidiosis in the future is by vaccine development.

The *Eimeria* parasite undergoes a complex life cycle in the mucosa of the intestinal tract. This life cycle is very similar to that of the other hemosporidian parasites (i.e. plasmodium, babesia, etc.) except for the lack of an arthropod vector. Oocysts sporulate on the litter floor producing four sporocysts, each containing two sporozoites (thus belonging to the class sporozoa). The oocysts are ingested by the chicken, and the sporocysts are released by the mechanical grinding of the gizzard. The sporozoites are then released from the sporocysts due to the digestion of the sporocyst wall by proteolytic enzymes in the intestine. Mobile sporozoites then invade lymphocytes and go on to invade epithelial cells where the asexual cycle begins. The parasite goes through 2-4 cycles of replication and division (each species having a defined number of divisions) leading to the production of large numbers of daughter merozoites. After the final cycle of merozoite production the sexual cycle begins with the production of the macrogametocyte (female) and microgametocyte (male). The macrogametocyte is characterized by the production of wall forming bodies, while microgametocytes contain the components involved in the formation of microgametes, which bud off from the surface of the intracellular parasite. Microgametes are flagellated and are responsible for the fertilization of the macrogamete. A zygote is formed which matures into the oocyst by fusion of the wall forming bodies and condensation of the nucleus. Oocysts are secreted in the feces, thus completing the cycle.

Over the past several years, native antigens from the sexual (gametocyte) stages of *Eimeria maxima* have been used to immunize laying hens. Offspring chicks were consequently vaccinated via maternal immunity (protective maternal antibody). Three major protective antigens have previously been identified in *E. maxima* gametocytes having molecular weights of 250, 82 and 56 kDa (EP Patent No. 0 256 536, U.S. Pat. Nos. 5,496,550, and 5,932,225). EP Patent No. 0 256 536, U.S. Pat. Nos. 5,496,550, and 5,932,225 are hereby incorporated by reference into this application in order to more fully describe the state of the art to which this invention pertains. It was shown that these antigens are well conserved amongst *Eimeria* species (Wallach 1995) and can cross protect against the 3 major species that cause coccidiosis in broiler chickens, *E. maxima, E. tenella* and *E. acervulina*. More recently, it was shown that in floor pen trials, chicks from hens vaccinated with these native gametocyte antigens were protected against *Eimeria* under field conditions (Wallach 1996). This protection acts to lower the peak in oocyst shedding to a level which does not cause any damaging effect on the performance of the broiler chicken. Based on the above results it was concluded that these antigens are effective against coccidiosis in chickens and also have the potential for use against coccidiosis in other domestic animals including turkeys, geese, sheep, cattle, pigs and fish.

These three antigens were also characterized at the molecular level. Cell free translation experiments were carried out to identify the RNA molecules that encode them (Mencher et al.). cDNA molecules that encode these antigens were cloned by immunoscreening of a cDNA library made in the expression vector lambda zap (4, U.S. Pat. No. 5,932,225). By this approach, the gene encoding the 250 kDa antigen was cloned and sequenced. The clone pEM 250/14 was partially sequenced in U.S. Pat. Nos. 5,932,225 and 5,496,550. FIG. 13*a* of the subject application reproduces FIG. 11 of U.S. Pat. Nos. 5,932,225 and 5,496,550, which portrays the DNA sequence of the first 293 nucleotides of clone pEM 250/14. FIG. 13*b* of the subject application reproduces FIG. 12 of U.S. Pat. Nos. 5,932,225 and 5,496,550, which shows the DNA sequence of the last 196 nucelotides of clone pEM 250/14. Also, in in U.S. Pat. Nos. 5,932,225 and 5,496,550, the putative genes encoding the 56 and 82 kDa antigens were cloned and sequenced.

Subsequently, Fried et al. sequenced the entire pEM 250/14 clone and found that the antigen had a molecular weight of 230 kDa rather than 250 kDa as had been previously thought. Fried et al. found that the 230 kDa gene contains highly repetitive motifs and that these repeats are contained throughout the entire gene (Fried et al.). This clone was expressed in bacteria using the pATH plasmid vector and it was shown that it is recognized by convalescent chicken sera taken 14 days post infection with *E. maxima*. Finally, it was shown that this gene is expressed only in the macrogametocyte stage and by immunofluorescence was found to be located in the wall forming bodies of the macrogamete (Fried et al.).

cDNA clones encoding the 56 and 82 kDa antigens were also obtained by screening the library with polyclonal antibodies as well as a monoclonal antibody against the 56 kDa antigen. This monoclonal antibody was previously shown to provide passive immunity to naive chicks (Wallach 1990). A few clones were obtained and analyzed. One of the clones was found to encode a small 10 kDa antigen and therefore was not the desired clone. Another clone was found to contain only a small part of the open reading frame (ORF) and by northern blotting was shown to hybridize with two mRNAs of about the expected size for the 56 and 82 kDa antigens. It was therefore concluded that this was the desired clone. Genomic libraries were then screened to obtain the full length clone. However, due to the highly repetitive GCA motifs in this clone, it was not possible to specifically isolate the full length clone. Attempts to clone the full length cDNA molecule were also not successful due to these repeats. Finally, attempts to express the partial cDNA clones in bacteria failed as well probably due to their unusual sequences and a reasonable level of gene expression was not obtained. It has previously been shown that the 56 and 82 kDa antigens are glycosylated (U.S. Pat. No. 5,932,225). This is based on their strong reactivity with Soybean lectin. Therefore, glycosylation may be required in order to obtain good expression of these genes and for proper conformation of the gene products.

In addition to the 56, 82 and 230 kDa antigens, a 14 kDa antigen obtained from highly purified fractions of oocyst walls has been proposed as a possible candidate for vaccines against coccidiosis (Eschenbacher et al.). However, this hypothesis has not been explored.

Several laboratories have been working on a subunit vaccine against coccidiosis. Most of these researchers have focused their efforts on the extracellular asexual stages of the life cycle, in particular the sporozoite and merozoite stages which are considered to be the most vulnerable to immune attack. In a previous study it was found that sporozoite extracts from *E. tenella* could induce in broilers protection against challenge infections against this parasite for up to 7 weeks of age (Karkhanis et al.). Work carried out using monoclonal antibodies against antigens from sporozoites of *E. tenella* led to the identification of a 25,000 molecular weight antigen which was cloned and sequenced (Eur. Patent publication No. 0 164 176, Dec. 11, 1985). Several other sporozoite genes were identified and their recombinant antigens or the transformed bacteria themselves were tested for protective immunity (Danforth et al.). The results indicated that these recombinants were only able to provide a relatively low level of protection against challenge infection with *Eimeria* and did not always prevent the appearance of significant lesions.

A vaccine using antigens from the merozoite stage has also been tested (European patent publication No. 0 135 073). Using these antigens to immunize young broiler chicks, it was once again found that the protection afforded was relatively low (Danforth et al.).

In 1993, it was found that there was a correlation between protective maternal immunity with the appearance of maternal antibodies against a 230 kDa merozoite (as opposed to gametocyte) antigen of *Eimeria maxima* (Smith et al.). This protection was often over 90% and was found to occur even when the maternal antibody level was relatively low (although reactivity with the 230 kDa protein remained strong). It was also found that a very small quantity of the native 230 kDa merozoite antigen cut out of an SDS-PAGE gel could induce a significant (60%) level of protective maternal immunity against infection with *E. maxima* in offspring chicks. Furthermore, Western blotting showed that this protein was expressed in both merozoites and sporozoites of *E. maxima* and is also well conserved between *Eimeria* species.

SUMMARY OF THE INVENTION

The present invention provides the nucleic acid encoding two of the major *Eimeria maxima* gametocyte antigens having molecular weights of 56 and 82 kDa.

The subject invention also provides a 30 kDa protein from *Eimeria maxima* gametocytes having at the N-terminal end the amino acid sequence shown by SEQ. ID NO. 35.

The subject invention also provides a 30 kDa protein from *Eimeria maxima* gametocytes having at the N-terminal end the amino acid sequence shown by SEQ. ID NO. 42.

The subject invention also provides a 14 kDa protein from *Eimeria maxima* gametocytes having at the N-terminal end the amino acid sequence shown by SEQ. ID NO. 37.

The subject invention also provides a 14 kDa protein from *Eimeria maxima* gametocytes having at the N-terminal end the amino acid sequence shown by SEQ. ID NO. 39.

The subject invention also provides a 14 kDa protein from *Eimeria maxima* gametocytes having at the N-terminal end the amino acid sequence shown by SEQ. ID NO. 41.

The subject invention also provides a vaccine against coccidiosis comprising the recombinant 56 kDa antigen alone or in combination with any of the aforementioned proteins.

The subject invention also provides a vaccine against coccidiosis comprising the recombinant 82 kDa antigen alone or in combination with any of the aforementioned proteins.

The subject invention also provides a method of immunizing an subject against infection by *Eimeria tenella, Eimeria maxima, Eimeria acervulina, Eimeria necatrix, Eimeria praecox, Eimeria mitis* or *Eimeria brunetti*, or a microorganism expressing an immunologically cross-reactive antigen, comprising the step of administering to the subject any of the aforementioned vaccines.

BRIEF DESCRIPTION OF THE FIGURES

FIG. 2 depicts a two-dimensional (2D) SDS-PAGE gel of affinity purified native gametocyte antigens after immunoblotting and silver staining. Molecular weight marker proteins are indicated.

FIGS. 4A-4C depicts the complete DNA sequence of the 56 kDa gametocyte antigen. The amino terminus as well as internal tryptic peptide fragments are designated. In addition, the predicted initiator methionine and signal peptide cleavage site are shown. The coding sequence, its complement and amino acid sequences are shown (SEQ. ID. NOs. 1-3).

FIGS. 5A-5D depicts the complete DNA sequence of the 82 kDa gametocyte antigen. The amino terminus as well as internal tryptic peptide fragments are designated. In addition, the predicted initiator methionine and signal peptide cleavage site are shown. The coding sequence, its complement and amino acid sequences are shown (SEQ. ID. NOs. 4-6).

FIG. 9 depicts an immunoblot showing reactivity of the anti polyhistidine antibody and chicken anti-APGA with proteins expressed by IPTG induced and non-induced (control) bacteria containing the 56 kDa cDNA clone in pTrcHisB. As a further negative control, bacteria that were transformed with the pTrcHisB plasmid containing no insert were tested. Finally, native APGA was used as a positive control for the blot with the anti APGA antiserum. The sizes of the protein marker bands are indicated. Arrows show the positions of the 41 kDa recombinant and 56 and 82 kDa native proteins.

FIGS. 12A-12K depicts DNA sequence alignment of the 230 kDa cDNA *E. maxima* clone with a homologous DNA sequence from patent WO 90/00403 showing 60% homology (SEQ. ID. NOs. 26-27).

FIG. 13a depicts the DNA sequence of the first 293 nucelotides of clone pEM 250/14. The coding sequence and its amino acid sequences are shown (SEQ. ID. NOs. 28-29). FIG. 13b depicts the DNA sequence of the last 196 nucelotides of clone pEM 250/14. The coding sequence and its amino acid sequences are shown (SEQ. ID. NOs. 30-31).

FIG. 15 DNA and encoded amino acid sequence of the expressed protein fragment from the 250 kDa asexual stage protein (SEQ. ID NOS. 32-33).

FIG. 19 Anti-r82 recognition of gametocyte and wall antigens in *Eimeria maxima*.

FIG. 20 Alignment of the N-terminus sequence of the oocyst wall proteins to the 56 kDa and 82 kDa gametocyte antigens (SEQ. ID NOS. 34-42).

DETAILED DESCRIPTION OF THE INVENTION

Figure 1:
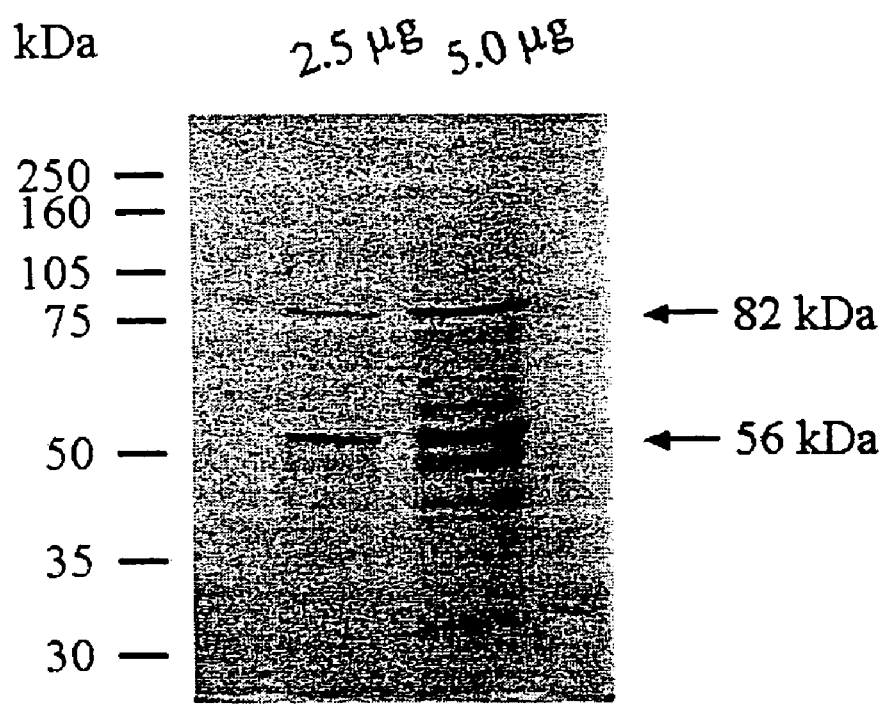
FIG. 1 depicts a Coomassie stained SDS PAGE gel of affinity purified native gametocyte antigens. Arrows point to the 56 and 82 kDa antigens. Molecular weight marker proteins are indicated.

The subject invention provides an isolated nucleic acid comprising a nucleotide sequence encoding a 56 kDa polypeptide from Gametocytes of *Eimeria maxima*, or encoding a homolog of the polypeptide, or a complement of the nucleic acid.

In one embodiment, the polypeptide has the amino acid sequence shown in FIG. 4 (SEQ. ID. NO. 3).

In another embodiment, the homolog of the polypeptide has at least 50% identity to the polypeptide having the sequence shown as SEQ. ID. NO. 3.

In an additional embodiment, the homolog of the polypeptide has at least 60% identity to the polypeptide having the sequence shown as SEQ. ID. NO. 3.

In a further embodiment, the homolog of the polypeptide has at least 70% identity to the polypeptide having the sequence shown as SEQ. ID. NO. 3.

In an added embodiment, the homolog of the polypeptide has at least 75% identity to the polypeptide having the sequence shown as SEQ. ID. NO. 3.

In yet another embodiment, the homolog of the polypeptide has at least 80% identity to the polypeptide having the sequence shown as SEQ. ID. NO. 3.

In a further embodiment, the homolog of the polypeptide has at least 85% identity to the polypeptide having the sequence shown as SEQ. ID. NO. 3.

In one embodiment, the homolog of the polypeptide has at least 90% identity to the polypeptide having the sequence shown as SEQ. ID. NO. 3.

In another embodiment, the homolog of the polypeptide has at least 93% identity to the polypeptide having the sequence shown as SEQ. ID. NO. 3.

In an additional embodiment, the homolog of the polypeptide has at least 95% identity to the polypeptide having the sequence shown as SEQ. ID. NO. 3.

In a further embodiment, the homolog of the polypeptide has at least 97% identity to the polypeptide having the sequence shown as SEQ. ID. NO. 3.

In yet another embodiment, the homolog of the polypeptide has at least 99% identity to the polypeptide having the sequence shown as SEQ. ID. NO. 3.

In an additional embodiment, the nucleotide sequence has at least 50% identity to the nucleotide sequence starting at nucleotide No. 103 and ending at nucleotide No. 1529 shown in FIG. 4 (SEQ. ID. NO. 1.)

In another embodiment, the nucleotide sequence has at least 60% identity to the nucleotide sequence starting at nucleotide No. 103 and ending at nucleotide No. 1529 shown as SEQ. ID. NO. 1.

In a further embodiment, the nucleotide sequence has at least 70% identity to the nucleotide sequence starting at nucleotide No. 103 and ending at nucleotide No. 1529 shown as SEQ. ID. NO. 1.

In one embodiment, the nucleotide sequence has at least 75% identity to the nucleotide sequence starting at nucleotide No. 103 and ending at nucleotide No. 1529 shown as SEQ. ID. NO. 1.

In another embodiment, the nucleotide sequence has at least 80% identity to the nucleotide sequence starting at nucleotide No. 103 and ending at nucleotide No. 1529 shown as SEQ. ID. NO. 1.

In an added embodiment, the nucleotide sequence has at least 85% identity to the nucleotide sequence starting at nucleotide No. 103 and ending at nucleotide No. 1529 shown as SEQ. ID. NO. 1.

In one embodiment, the nucleotide sequence has at least 90% identity to the nucleotide sequence starting at nucleotide No. 103 and ending at nucleotide No. 1529 shown as SEQ. ID. NO. 1.

In a further embodiment, the nucleotide sequence has at least 93% identity to the nucleotide sequence starting at nucleotide No. 103 and ending at nucleotide No. 1529 shown as SEQ. ID. NO. 1.

In another embodiment, the nucleotide sequence has at least 95% identity to the nucleotide sequence starting at nucleotide No. 103 and ending at nucleotide No. 1529 shown as SEQ. ID. NO. 1.

In an added embodiment, the nucleotide sequence has at least 97% identity to the nucleotide sequence starting at nucleotide No. 103 and ending at nucleotide No. 1529 shown as SEQ. ID. NO. 1.

In one embodiment, the nucleotide sequence has at least 99% identity to the nucleotide sequence starting at nucleotide No. 103 and ending at nucleotide No. 1529 shown as SEQ. ID. NO. 1.

In a further embodiment, the nucleic acid is a DNA molecule.

In yet another embodiment, the DNA molecule is a cDNA molecule.

In an added embodiment, the nucleic acid has the nucleotide sequence starting at nucleotide No. 103 and ending at nucleotide No. 1529 shown in FIG. 4(SEQ. ID. NO. 1).

In another embodiment, the nucleic acid is an RNA molecule.

In one embodiment, the isolated nucleic acid is operatively linked to a promoter of RNA transcription.

The subject invention also includes a vector comprising an isolated nucleic acid comprising a nucleotide sequence encoding a 56 kDa polypeptide from Gametocytes of *Eimeria maxima*, or encoding a homolog of the polypeptide, or a complement of the nucleic acid.

In one embodiment, the vector comprises the nucleic acid having the nucleotide sequence starting at nucleotide No. 103 and ending at nucleotide No. 1529 shown in FIG. 4 (SEQ. ID. NO. 1).

In another embodiment, the vector is a plasmid.

In a further embodiment, the plasmid comprises the nucleic acid having the nucleotide sequence starting at nucleotide No. 103 and ending at nucleotide No. 1529 shown in FIG. 4 (SEQ. ID. NO. 1).

In an additional embodiment, the plasmid comprises an isolated nucleic acid comprising a nucleotide sequence encoding a 56 kDa polypeptide from Gametocytes of *Eimeria maxima*, or encoding a homolog of the polypeptide, or a complement of the nucleic acid.

In yet another embodiment, the plasmid is the plasmid designated 56TRCHisb1 plasmid (Australian Government Analytical Laboratories Accession No. NM01/22400).

The subject invention also encompasses a host cell comprising a vector which comprises an isolated nucleic acid comprising a nucleotide sequence encoding a 56 kDa polypeptide from Gametocytes of *Eimeria maxima*, or encoding a homolog of the polypeptide, or a complement of the nucleic acid.

In one embodiment, the host cell comprises a vector comprising a nucleic acid having the nucleotide sequence starting at nucleotide No. 103 and ending at nucleotide No. 1529 shown in FIG. 4 (SEQ. ID. NO. 1).

In another embodiment, the host cell is selected from the group consisting of a bacterial cell; a plant cell; an insect cell; and a mammalian cell.

The subject invention additionally presents a transformed cell comprising an isolated nucleic acid comprising a nucleotide sequence encoding a 56 kDa polypeptide from Gametocytes of *Eimeria maxima*, or encoding a homolog of the polypeptide, or a complement of the nucleic acid.

In one embodiment, the transformed cell is the transformed cell designated clone 56TRCHisb1 in bacteria (Australian Government Analytical Laboratories Accession No. NM01/22401).

A plasmid encoding the 56 kDa antigen was deposited with the Australian Government Analytical Laboratories, Pymble, Australia, on Jun. 26, 2001, under Accession No. NM01/22400. The bacterial cell transformed with the 56 kDa antigen was deposited with the Australian Government Analytical Laboratories, Pymble, Australia, on Jun. 26, 2001, under Accession No. NM01/22401. Both deposits were made according to the Budapest Treaty on the International Recognition of the Deposit of Microorganisms for the Purposes of Patent Procedure.

In an added embodiment, the transformed cell further comprises a 56 kDa polypeptide from Gametocytes of *Eimeria maxima*, or a homolog of the polypeptide.

The subject invention further contains a method of producing a recombinant 56 kDa polypeptide from Gametocytes of *Eimeria maxima* comprising culturing a transformed cell comprising an isolated nucleic acid comprising a nucleotide sequence encoding a 56 kDa polypeptide from Gametocytes of *Eimeria maxima*, or encoding a homolog of the polypeptide, or a complement of the nucleic acid and isolating the recombinant 56 kDa polypeptide from Gametocytes of *Eimeria maxima*. The recombinant polypeptide produced by this method is also encompassed by the subject invention.

The subject invention also provides a vaccine against *Eimeria tenella, Eimeria maxima, Eimeria acervulina, Eimeria necatrix* or *Eimeria brunetti, Eimeria praecox, Eimeria mitis* or a microorganism expressing an immunologically cross-reactive antigen, comprising the isolated nucleic acid comprising a nucleotide sequence encoding a 56 kDa polypeptide from Gametocytes of *Eimeria maxima*, or encoding a homolog of the polypeptide, or a complement of the nucleic acid.

In one embodiment of the vaccine, the isolated nucleic acid is a plasmid.

In addition, the subject invention presents a vaccine against *Eimeria tenella, Eimeria maxima, Eimeria acervulina, Eimeria necatrix* or *Eimeria brunetti, Eimeria praecox, Eimeria mitis* or a microorganism expressing an immunologically cross-reactive antigen, comprising a recombinant 56 kDa polypeptide from Gametocytes of *Eimeria maxima* produced by culturing a transformed cell comprising an isolated nucleic acid comprising a nucleotide sequence encoding a 56 kDa polypeptide from Gametocytes of *Eimeria maxima*, or encoding a homolog of the polypeptide, or a complement of the nucleic acid and isolating the recombinant 56 kDa polypeptide from Gametocytes of *Eimeria maxima*.

In another embodiment, the vaccine is comprised of a mixture of the isolated nucleic acid of the subject invention and the recombinant polypeptide of the subject invention.

In another embodiment, the vaccine is comprised of a mixture of the isolated nucleic acid of the subject invention, the recombinant polypeptide of the subject invention and a plasmid comprising the isolated nucleic acid comprising a nucleotide sequence encoding a 56 kDa polypeptide from Gametocytes of *Eimeria maxima*.

In an added embodiment, the vaccine further comprises a second antigen.

In one embodiment, the second antigen is selected from the group consisting of a nucleic acid coding for an antigen from *Eimeria maxima*, a plasmid comprising such a nucleic acid, and a polypeptide coded by such a nucleic acid.

In another embodiment, the second antigen is selected from the group consisting of a 30 kDa protein from *Eimeria maxima* gametocytes having at the N-terminal end the amino acid sequence shown as SEQ. ID NO. 35, or SEQ. ID NO. 42 or a 14 kDa protein from *Eimeria maxima* gametocytes having at the N-terminal end the amino acid sequence shown as SEQ. ID NO. 37, SEQ. ID NO. 39 or SEQ. ID NO. 41.

In yet another embodiment, the second antigen is a nucleic acid having the nucleotide sequence shown in Seq. ID. No. 4, a plasmid comprising the nucleic acid or a polypeptide coded by the nucleic acid.

In a further embodiment, the vaccine further comprises a third antigen.

The subject invention also provides a vaccine wherein the third antigen is a 230 kDa sporozoite/merozoite antigen from *E. maxima*.

The 230 kDa antigen was isolated from purified *E. maxima* sporozoites which are present in sporulated oocysts (see life cycle above). The isolation procedure involved extraction of proteins from the sporulated oocysts and separation of the extracted proteins on a DEAE-sephacel anion-exchange column. This was followed by SDS-PAGE of the peak fractions and Western blotting to identify the 230 kDa antigen. Furthermore, protective maternal antisera both from vaccinated hens and offspring chicks were used to confirm the identity of the purified antigen. Finally, the 230 kDa protein was isolated from a PVDF membrane filter for carrying out protein sequencing and cloning.

The amino terminal and tryptic peptide digest products of the 230 kDa antigen were sequenced. The sequences from the tryptic digest were used to design degenerate PCR oligonucleotide primers. The primers were used in RACE (rapid amplification of cDNA ends) PCR to amplify partial gene products. From the sequences of these products, gene specific primers were designed and used in RACE PCR to define the 3' and 5' ends of the mRNA. A full length 7 kilobase cDNA clone encoding the antigen was then amplified by PCR using gene specific primers designed to the 5' and 3' ends. This clone was fully sequenced and shown to contain the correct DNA sequence at its 5' end when compared to the amino acid sequence of the N-terminus of the native protein. Thus, this nucleic acid sequence encoded the protective 230 kDa sporozoite/merozoite antigen and could now be used to produce recombinant antigen for vaccination of chickens against coccidiosis.

A plasmid encoding the 230 kDa antigen was deposited with the Australian Government Analytical Laboratories, Pymble, Australia, on Jun. 26, 2001, under Accession No. NM01/22396. The bacterial cell transformed with the 230 kDa antigen was deposited with the Australian Government Analytical Laboratories, Pymble, Australia, on Jun. 26, 2001, under Accession No. NM01/22397. Both deposits were made according to the Budapest Treaty on the International Recognition of the Deposit of Microorganisms for the Purposes of Patent Procedure.

It was previously thought that the antigen from the sporozoites/merozoites of *E. maxima* was a 230 kDa antigen. However, our subsequent studies have revealed that the antigen actually is a 250 kDa antigen of the sporozoites/merozoites of *E. maxima*.

In an additional embodiment, the third antigen is a nucleic acid having the nucleotide sequence shown in FIG. 12 (SEQ. ID. NO. 26), a plasmid comprising the nucleic acid, or a polypeptide coded by the nucleic acid.

In still another embodiment, the vaccine further comprises a fourth antigen.

In one embodiment, the fourth antigen is a polypeptide from Gametocytes of *Eimeria maxima* having a molecular weight from 230 kDa to 270 kDa, a nucleotide sequence encoding the polypeptide, or a plasmid comprising the nucleotide sequence.

In a further embodiment, the antigen comprises a polypetide having the amino acid sequence shown in FIG. 13*a* (SEQ. ID. NO. 29) at its 5' end or the amino acid sequence shown in FIG. 13*b* (SEQ. ID. NO. 31) at its 3' end.

The subject invention also provides a method of immunizing a subject against infection by *Eimeria tenella, Eimeria maxima, Eimeria acervulina, Eimeria necatrix, Eimeria praecox, Eimeria mitis* or *Eimeria brunetti*, or a microorganism expressing an immunologically cross-reactive antigen, comprising the step of administering to the subject the vaccine of the subject invention.

In one embodiment, the subject is a species selected from the group consisting of cattle, sheep, pigs and fish.

In another embodiment, the subject is an avian species.

In a further embodiment, the avian species is selected from the group consisting of chickens, turkeys, geese, ducks, bantams, quail and pigeons.

In an additional embodiment, the avian species is chickens.

In one embodiment, the administering step comprises spraying the vaccine into the nostrils of the subject.

In a further embodiment, the administration comprises intravenous, intramuscular or intraperitoneal injection.

In another embodiment, the administration is performed in ovo.

In a further embodiment, the administration is to the air sac of an egg, thus contacting an embryo with the vaccine.

The subject invention also contains a fertilized egg from an avian species having an air sac which is inoculated with the vaccine of the subject invention, which vaccine is capable of inducing before or immediately after hatching an immune response in the embryo against a virulent form of *Eimeria tenella, Eimeria maxima, Eimeria acervulina, Eimeria necatrix, Eimeria praecox, Eimeria mitis* or *Eimeria brunetti*, or a microorganism expressing an immunologically cross-reactive antigen.

In one embodiment, the avian species is selected from the group consisting of chickens, ducks, turkeys, geese, bantams, quail and pigeons.

In another embodiment, the avian species is chickens.

The subject invention additionally provides an isolated nucleic acid comprising a nucleotide sequence encoding a 82 kDa polypeptide from Gametocytes of *Eimeria maxima*, or encoding a homolog of the polypeptide, or a complement of the nucleic acid.

In one embodiment, the polypeptide has the amino acid sequence shown in FIG. 5 (SEQ. ID. NO. 6).

In another embodiment, the homolog of the polypeptide has at least 50% identity to the polypeptide having the sequence shown as SEQ. ID. NO. 6.

In an additional embodiment, the homolog of the polypeptide has at least 60% identity to the polypeptide having the sequence shown as SEQ. ID. NO. 6.

In a further embodiment, the homolog of the polypeptide has at least 70% identity to the polypeptide having the sequence shown as SEQ. ID. NO. 6.

In another embodiment, the homolog of the polypeptide has at least 75% identity to the polypeptide having the sequence shown as SEQ. ID. NO. 6.

In yet another embodiment, the homolog of the polypeptide has at least 80% identity to the polypeptide having the sequence shown as SEQ. ID. NO. 6.

In an added embodiment, the homolog of the polypeptide has at least 85% identity to the polypeptide having the sequence shown as SEQ. ID. NO. 6.

In one embodiment, the homolog of the polypeptide has at least 90% identity to the polypeptide having the sequence shown as SEQ. ID. NO. 6.

In a further embodiment, the homolog of the polypeptide has at least 93% identity to the polypeptide having the sequence shown as SEQ. ID. NO. 6.

In yet another embodiment, the homolog of the polypeptide has at least 95% identity to the polypeptide having the sequence shown as SEQ. ID. NO. 6.

In one embodiment, the homolog of the polypeptide has at least 97% identity to the polypeptide having the sequence shown as SEQ. ID. NO. 6.

In an additional embodiment, the homolog of the polypeptide has at least 99% identity to the polypeptide having the sequence shown as SEQ. ID. NO. 6.

In an additional embodiment, the nucleotide sequence has greater than 50% identity to the nucleotide sequence starting at nucleotide No. 100 and ending at nucleotide No. 1886 shown in FIG. 5 (SEQ. ID. NO. 4).

In another embodiment, the nucleotide sequence has greater than 60% identity to the nucleotide sequence starting at nucleotide No. 100 and ending at nucleotide No. 1886 shown as SEQ. ID. NO. 4.

In a further embodiment, the nucleotide sequence has at least 70% identity to the nucleotide sequence starting at nucleotide No. 100 and ending at nucleotide No. 1886 shown as SEQ. ID. NO. 4.

In an additional embodiment, the nucleotide sequence has at least 75% identity to the nucleotide sequence starting at nucleotide No. 100 and ending at nucleotide No. 1886 shown as SEQ. ID. NO. 4.

In another embodiment, the nucleotide sequence has at least 80% identity to the nucleotide sequence starting at nucleotide No. 100 and ending at nucleotide No. 1886 shown as SEQ. ID. NO. 4.

In yet another embodiment, the nucleotide sequence has at least 85% identity to the nucleotide sequence starting at nucleotide No. 100 and ending at nucleotide No. 1886 shown as SEQ. ID. NO. 4.

In one embodiment, the nucleotide sequence has at least 90% identity to the nucleotide sequence starting at nucleotide No. 100 and ending at nucleotide No. 1886 shown as SEQ. ID. NO. 4.

In an additional embodiment, the nucleotide sequence has at least 93% identity to the nucleotide sequence starting at nucleotide No. 100 and ending at nucleotide No. 1886 shown as SEQ. ID. NO. 4.

In another embodiment, the nucleotide sequence has at least 95% identity to the nucleotide sequence starting at nucleotide No. 100 and ending at nucleotide No. 1886 shown as SEQ. ID. NO. 4.

In a further embodiment, the nucleotide sequence has at least 97% identity to the nucleotide sequence starting at nucleotide No. 100 and ending at nucleotide No. 1886 shown as SEQ. ID. NO. 4.

In one embodiment, the nucleotide sequence has at least 99% identity to the nucleotide sequence starting at nucleotide No. 100 and ending at nucleotide No. 1886 shown as SEQ. ID. NO. 4.

In a further embodiment, the nucleic acid is a DNA molecule.

In yet another embodiment, the DNA molecule is a cDNA molecule.

In an added embodiment, the nucleic acid has the nucleotide sequence starting at nucleotide No. 100 and ending at nucleotide No. 1886 shown as SEQ. ID. NO. 4.

In another embodiment, the nucleic acid is an RNA molecule.

In one embodiment, the isolated nucleic acid is operatively linked to a promoter of RNA transcription.

The subject invention also includes a vector comprising an isolated nucleic acid comprising a nucleotide sequence encoding a 82 kDa polypeptide from Gametocytes of *Eimeria maxima*, or encoding a homolog of the polypeptide, or a complement of the nucleic acid.

In one embodiment, the vector comprises the nucleic acid having the nucleotide sequence starting at nucleotide No. 100 and ending at nucleotide No. 1886 shown in FIG. 5 (SEQ. ID. NO. 4).

In another embodiment, the vector is a plasmid.

In a further embodiment, the plasmid comprises the nucleic acid having the nucleotide sequence starting at nucleotide No. 100 and ending at nucleotide No. 1886 shown in FIG. 5 (SEQ. ID. NO. 4).

In an additional embodiment, the plasmid comprises an isolated nucleic acid comprising a nucleotide sequence encoding a 82 kDa polypeptide from Gametocytes of *Eimeria maxima*, or encoding a homolog of the polypeptide, or a complement of the nucleic acid.

In yet another embodiment, the plasmid is the plasmid designated 82TRCHisb8 plasmid (Australian Government Analytical Laboratories Accession No. NM01/22398).

The subject invention also encompasses a host cell comprising a vector which comprises an isolated nucleic acid comprising a nucleotide sequence encoding a 82 kDa polypeptide from Gametocytes of *Eimeria maxima*, or encoding a homolog of the polypeptide, or a complement of the nucleic acid.

In one embodiment, the host cell comprises a vector comprising a nucleic acid having the nucleotide sequence starting at nucleotide No. 100 and ending at nucleotide No. 1886 shown in FIG. 5 (SEQ. ID. NO. 4).

In another embodiment, the host cell is selected from the group consisting of a bacterial cell; a plant cell; an insect cell; and a mammalian cell.

The subject invention additionally presents a transformed cell comprising an isolated nucleic acid comprising a nucleotide sequence encoding a 82 kDa polypeptide from Gametocytes of *Eimeria maxima*, or encoding a homolog of the polypeptide, or a complement of the nucleic acid.

In one embodiment, the transformed cell is the transformed cell designated clone 82TRCHisb8 in bacteria (Australian Government Analytical Laboratories Accession No. NM01/22399).

A plasmid encoding the 82 kDa antigen was deposited with the Australian Government Analytical Laboratories, Pymble, Australia, on Jun. 26, 2001, under Accession No. NM01/22398. The bacterial cell transformed with the 82 kDa antigen was deposited with the Australian Government Analytical Laboratories, Pymble, Australia, on Jun. 26, 2001, under Accession No. NM01/22399. Both deposits were made according to the Budapest Treaty on the International Recognition of the Deposit of Microorganisms for the Purposes of Patent Procedure.

In an added embodiment, the transformed cell further comprises a 82 kDa polypeptide from Gametocytes of *Eimeria maxima*, or a homolog of the polypeptide.

The subject invention further contains a method of producing a recombinant 82 kDa polypeptide from Gametocytes of *Eimeria maxima* comprising culturing a transformed cell comprising an isolated nucleic acid comprising a nucleotide sequence encoding a 82 kDa polypeptide from Gametocytes of *Eimeria maxima*, or encoding a homolog of the polypeptide, or a complement of the nucleic acid and isolating the recombinant 82 kDa polypeptide from Gametocytes of *Eimeria maxima*. The recombinant polypeptide produced by this method is also encompassed by the subject invention.

The subject invention also provides a vaccine against *Eimeria tenella, Eimeria maxima, Eimeria acervulina, Eimeria necatrix, Eimeria praecox, Eimeria mitis* or *Eimeria brunetti*, or a microorganism expressing an immunologically cross-reactive antigen, comprising the isolated nucleic acid comprising a nucleotide sequence encoding a 82 kDa polypeptide from Gametocytes of *Eimeria maxima*, or encoding a homolog of the polypeptide, or a complement of the nucleic acid.

In one embodiment of the vaccine, the isolated nucleic acid is a plasmid.

In addition, the subject invention presents a vaccine against *Eimeria tenella, Eimeria maxima, Eimeria acervulina, Eimeria necatrix, Eimeria praecox, Eimeria mitis* or *Eimeria brunetti*, or a microorganism expressing an immunologically cross-reactive antigen, comprising a recombinant 82 kDa polypeptide from Gametocytes of *Eimeria maxima* produced by culturing a transformed cell comprising an isolated nucleic acid comprising a nucleotide sequence encoding a 82 kDa polypeptide from Gametocytes of *Eimeria maxima*, or encoding a homolog of the polypeptide, or a complement of the nucleic acid and isolating the recombinant 82 kDa polypeptide from Gametocytes of *Eimeria maxima*.

In another embodiment, the vaccine is comprised of a mixture of the isolated nucleic acid of the subject invention and the recombinant polypeptide of the subject invention.

In another embodiment, the vaccine is comprised of a mixture of the isolated nucleic acid of the subject invention, the recombinant polypeptide of the subject invention and a plasmid comprising the isolated nucleic acid comprising a nucleotide sequence encoding a 82 kDa polypeptide from Gametocytes of *Eimeria maxima*.

In an added embodiment, the vaccine further comprises a second antigen.

In one embodiment, the second antigen is selected from the group consisting of a nucleic acid coding for an antigen from *Eimeria maxima*, a plasmid comprising such a nucleic acid, and a polypeptide coded by such a nucleic acid.

In another embodiment, the second antigen is selected from the group consisting of a 30 kDa protein from *Eimeria maxima* gametocytes having at the N-terminal end the amino acid sequence shown as SEQ. ID NO. 35, or SEQ. ID NO. 42 or a 14 kDa protein from *Eimeria maxima* gametocytes having at the N-terminal end the amino acid sequence shown as SEQ. ID NO. 37, SEQ. ID NO. 39 or SEQ. ID NO. 41.

The subject invention also provides a method of immunizing a subject against infection by *Eimeria tenella, Eimeria maxima, Eimeria acervulina, Eimeria necatrix, Eimeria praecox, Eimeria mitis* or *Eimeria brunetti*, or a microorganism expressing an immunologically cross-reactive antigen, comprising the step of administering to the subject the vaccine of the subject invention.

In one embodiment, the subject is a species selected from the group consisting of cattle, sheep, pigs and fish.

In another embodiment, the subject is an avian species.

In a further embodiment, the avian species is selected from the group consisting of chickens, turkeys, geese, ducks, bantams, quail and pigeons.

In an additional embodiment, the avian species is chickens.

In a further embodiment, the administration comprises intravenous, intramuscular or intraperitoneal injection.

In one embodiment, the administering step comprises spraying the vaccine into the nostrils of the subject.

In another embodiment, the administration is performed in ovo.

In a further embodiment, the administration is to the air sac of an egg, thus contacting an embryo with the vaccine.

The subject invention also contains a fertilized egg from an avian species having an air sac which is inoculated with the vaccine of the subject invention, which vaccine is capable of inducing before or immediately after hatching an immune response in the embryo against a virulent form of *Eimeria tenella, Eimeria maxima, Eimeria acervulina, Eimeria necatrix, Eimeria praecox, Eimeria mitis* or *Eimeria brunetti*, or a microorganism expressing an immunologically cross-reactive antigen.

In one embodiment, the avian species is selected from the group consisting of chickens, ducks, turkeys, geese, bantams, quail and pigeons.

In another embodiment, the avian species is chickens.

The subject invention also provides a recombinant polypeptide, wherein the amino acid sequence is shown as SEQ. ID NO. 3.

The subject invention also provides a recombinant polypeptide, wherein the amino acid sequence is shown as SEQ. ID NO. 6.

The subject invention also provides a 30 kDa protein from *Eimeria maxima* gametocytes having at the N-terminal end the amino acid sequence shown as SEQ. ID NO. 35

The subject invention also provides a 30 kDa protein from Eimeria maxima gametocytes having at the N-terminal end the amino acid sequence shown as SEQ. ID NO. 42.

The subject invention also provides a 14 kDa protein from *Eimeria maxima* gametocytes having at the N-terminal end the amino acid sequence shown as SEQ. ID NO. 37.

The subject invention also provides a 14 kDa protein from Eimeria maxima gametocytes having at the N-terminal end the amino acid sequence shown as SEQ. ID NO. 39.

The subject invention also provides a 14 kDa protein from *Eimeria maxima* gametocytes having at the N-terminal end the amino acid sequence shown as SEQ. ID NO. 41.

The aforementioned proteins and their corresponding nucleotide sequences can be used in the same manner as described above for the 56 kDa and 82 kDa proteins, including being used to immunize a subject, and to incorporate a plasmid containing a nucleotide sequence encoding the protein into a host cell.

The subject invention also provides a method of conferring upon a newborn subject of an avian species maternal immunity (antibodies) against infection by *Eimeria tenella, Eime-* ria maxima, Eimeria acervulina, Eimeria necatrix, Eimeria praecox, Eimeria mitis or Eimeria brunetti, or a microorganism expressing an immunologically cross-reactive antigen, comprising the step of administering to the mother of the subject at a suitable time prior to the laying of a fertilized egg the vaccine of the subject invention in order to thereby confer protection via maternal immunity against infection by Eimeria tenella, Eimeria maxima, Eimeria acervulina, Eimeria necatrix, Eimeria praecox, Eimeria mitis or Eimeria brunetti, or a microorganism expressing an immunologically cross-reactive antigen, in the newborn subject.

In a further embodiment, the avian species is selected from the group consisting of chickens, turkeys, geese, ducks, bantams, quail and pigeons.

In a further embodiment, the administration comprises intravenous, intramuscular or intraperitoneal injection.

The subject invention also provides a method of reducing the output of Eimeria oocysts in feces from a newborn subject of an avian species which comprises the step of administering to the mother of the subject at a suitable time prior to the laying of a fertilized egg the vaccine of the subject invention in order induce an immune response and transmit maternal antibodies to the newborn so that the output of oocysts from the newborn is reduced.

In a further embodiment, the avian species is selected from the group consisting of chickens, turkeys, geese, ducks, bantams, quail and pigeons.

In a further embodiment, the administration comprises intravenous, intramuscular or intraperitoneal injection.

The subject invention also provides a method of immunizing a subject against infection by Eimeria tenella, Eimeria maxima, Eimeria acervulina, Eimeria necatrix, Eimeria praecox, Eimeria mitis or Eimeria brunetti, or a microorganism expressing an immunologically cross-reactive antigen, comprising the step of administering to the subject a live vaccine comprising a living non-virulent micro-organism or live virus that expresses a 56 kDa or 82 kDa polypeptide from the gametocytes of Eimeria maxima.

In one embodiment, the live virus is the pox virus.

In one embodiment, the subject is a species selected from the group consisting of cattle, sheep, pigs and fish.

In another embodiment, the subject is an avian species.

In a further embodiment, the avian species is selected from the group consisting of chickens, turkeys, geese, ducks, bantams, quail and pigeons.

In a further embodiment, the administration comprises intravenous, intramuscular or intraperitoneal injection.

The subject invention also provides a method of immunizing a subject against infection by Eimeria tenella, Eimeria maxima, Eimeria acervulina, Eimeria necatrix, Eimeria praecox, Eimeria mitis or Eimeria brunetti, or a microorganism expressing an immunologically cross-reactive antigen, comprising the step of feeding to the subject a plant whose cells express a 56 kDa or 82 kDa polypeptide from the gametocytes of Eimeria maxima.

In one embodiment, the plant is wheat.

In another embodiment, the plant is corn.

In one embodiment, the subject is a species selected from the group consisting of cattle, sheep, pigs and fish.

In another embodiment, the subject is an avian species.

In a further embodiment, the avian species is selected from the group consisting of chickens, turkeys, geese, ducks, bantams, quail and pigeons.

The subject invention also provides a method of immunizing a subject against infection by Eimeria tenella, Eimeria maxima, Eimeria acervulina, Eimeria necatrix, Eimeria praecox, Eimeria mitis or Eimeria brunetti, or a microorganism expressing an immunologically cross-reactive antigen, comprising the step of administering to the subject a plasmid comprising an isolated nucleic acid comprising a nucleotide sequence encoding a 56 kDa or 82 kDa polypeptide from the gametocytes of Eimeria maxima, or encoding a homolog of the polypeptide, or a complement of the nucleic acid.

In one embodiment, the subject is a species selected from the group consisting of cattle, sheep, pigs and fish.

In another embodiment, the subject is an avian species.

In a further embodiment, the avian species is selected from the group consisting of chickens, turkeys, geese, ducks, bantams, quail and pigeons.

In a further embodiment, the administration comprises intravenous, intramuscular or intraperitoneal injection.

A homolog of the nucleic acid of the invention is a nucleic acid that codes for a polypeptide which has substantially the same biological activity as the polypeptide encoded by the nucleic acid. The term "homology", as used herein, refers to a degree of complementarity. There may be partial homology or complete homology (i.e., identity). A partially complementary sequence is one that at least partially inhibits an identical sequence from hybridizing to a target nucleic acid; it is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding, the probe will not hybridize to the second non-complementary target sequence.

As known in the art, numerous equivalent conditions may be employed to comprise either low or high stringency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution may be varied to generate conditions of either low or high stringency different from, but equivalent to, the above listed conditions.

It is an object of the present invention to provide nucleotide sequences encoding the 56 and 82 kDa antigens from Gametocytes of Eimeria maxima and the deduced amino acid sequence therefor. Specifically exemplified coding sequences are given in FIGS. 4 and 5, together with the deduced amino acid sequence. All synonymous coding sequences for the exemplified amino acid sequences are within the scope of the present invention.

It is a further object of the present invention to provide functionally equivalent coding and protein sequences, including equivalent sequences from other Eimeria species. Functionally equivalent 56 and 82 kDA antigens from Gametocytes of Eimeria maxima coding sequences are desirably from about 50% to about 80% nucleotide sequence homology (identity) to the specifically identified coding sequence, from about 80% to about 95%, and desirably from about 95% to about 100% identical in coding sequence to the specifically exemplified coding sequence.

Hybridization conditions of particular stringency provide for the identification of homologs of the coding sequence from other species and the identification of variant sequences, where those homologs and/or variant sequences have at least (inclusively) 50 to 85%, 85 to 100% nucleotide sequence identity, 90 to 100%, or 95 to 100% nucleotide sequence identity. Each integer and each subset of each specified range is intended within the context of the present invention.

The coding sequence and methods of the present invention include the homologous coding sequences in species other than *Eimeria maxima*. Methods can be employed to isolate the corresponding coding sequences (for example, from cDNA) from other organisms, including but not limited to other species such as *Eimeria tenella, Eimeria acervulina, Eimeria necatrix, Eimeria praecox, Eimeria mitis* and *Eimeria brunetti* useful in the methods of this invention using the sequences disclosed herein and experimental techniques well known to the art.

Specifically included in this invention are sequences from other species than those exemplified herein, which sequences hybridize to the sequences disclosed under stringent conditions. Stringent conditions refer to conditions understood in the art for a given probe length and nucleotide composition and capable of hybridizing under stringent conditions means annealing to a subject nucleotide sequence, or its complementary strand, under standard conditions (i.e., high temperature and/or low salt content) which tend to disfavor annealing of unrelated sequences.

"Conditions of high stringency" means hybridization and wash conditions of 65°-68° C., 0.1×SSC and 0.1% SDS (indicating about 95-100% nucleotide sequence identity/similarity). Hybridization assays and conditions are further described in Sambrook et al. (1989) Molecular Cloning, Second Edition, Cold Spring Harbor Laboratory, Plainview, N.Y. As used herein, conditions of moderate (medium) stringency are those with hybridization and wash conditions if 50-65° C., 1×SSC and 0.1% SDS (where a positive hybridization result reflects about 80-95% nucleotide sequence identity). Conditions of low stringency are typically those with hybridization and wash conditions of 40-50° C., 6×.SSC and 0.1% SDS (reflecting about 50-80% nucleotide sequence identity).

A homolog of the polypeptide of the invention is a polypeptide which has substantially the same amino acid sequence and biological activity as the polypeptide. Thus, a homolog may differ from the polypeptide of the invention by the addition, deletion, or substitution of one or more non-essential amino acid residues, provided that the resulting polypeptide retains the biological activity of the polypeptide. Persons skilled in the art can readily determine which amino acids residues may be added, deleted, or substituted (including with which amino acids such substitutions may be made) using established and well known procedures, including, for example, conventional methods for the design and manufacture of DNA sequences coding for bacterial expression of polypeptide homologs of the subject polypeptide, the modification of cDNA and genomic sequences by site-directed mutagenesis techniques, the construction of recombinant polypeptides and expression vectors, the bacterial expression of the polypeptides, and the measurement of the biochemical activity of the polypeptides by means of conventional biochemical assays.

Examples of homologs are deletion homologs containing less than all the residues specified in the subject polypeptide, substitution homologs wherein one or more residues specified are replaced by other residues, and addition homologs wherein one or more amino acids residues are added to the polypeptide. All such homologs share the biological activity of the polypeptide of the invention.

"Substantially the same polypeptide" is herein defined as encompassing the deletion, addition or substitution of fewer than four amino acids at the N-terminus of the amino acid sequence of the polypeptide. Furthermore, there may be deletions, additions or substitutions in the sequence which do not eliminate the biological activity of the polypeptide. Such modifications are known to those skilled in the art. For example, substitutions may encompass up to 10 residues in accordance with the homologous or equivalent groups described by e.g. Lehninger, Biochemistry, 2nd ed. Worth Pub., New York. (1975); Creighton, Protein Structure, a Practical Approach, IRL Press at Oxford Univ. Press, Oxford, England (1989); and Dayhoff, Atlas of Protein Sequence and Structure 1972, National Biomedical Research Foundation, Maryland (1972).

The term "biologically active", as used herein, refers to a polypeptide having structural, regulatory, or biochemical functions of a naturally occurring molecule. Likewise, "immunologically active" refers to the capability of the natural, recombinant, or synthetic polypeptide, or any oligopeptide portion thereof, to induce a specific immune response in an animal or cells and to bind with specific antibodies.

"Substantially the same biological activity" refers to biological activity the same as that of the naturally occurring molecule possibly differing slightly in degree or level which would still be known by the skilled artisan to be the same biological activity.

The term "portion", as used herein, in connection with a polypeptide (as in "a portion of a given polypeptide") refers to fragments of that polypeptide. The fragments may range in size from four (4) amino acid residues to the entire amino acid sequence minus one amino acid. The term "portion", as used herein, in connection with a nucleic acid (as in "a portion of a given nucleic acid") refers to fragments of that nucleic acid. The fragments may range in size from twelve (12) nucleotide residues to the entire nucleic acid sequence minus one nucleotide.

A "deletion", as used herein, refers to a change in either amino acid or nucleotide sequence in which one or more amino acid or nucleotide residues, respectively, are absent.

An "insertion" or "addition", as used herein, refers to a change in an amino acid or nucleotide sequence resulting in the addition of one or more amino acid or nucleotide residues, respectively, as compared to the naturally occurring molecule.

A "substitution", as used herein, refers to the replacement of one or more amino acids or nucleotides by different amino acids or nucleotides, respectively.

The present invention provides the recombinant cloning and sequencing of two of the major *Eimeria maxima* gametocyte antigens having molecular weights of 56 and 82 kDa.

The present invention also provides the expression of these recombinant antigens in an *E. coli* expression system using the plasmid pTrcHis.

The subject invention also provides a vaccine against coccidiosis comprising the recombinant 56 kDa antigen. In addition, the present invention provides a vaccine against coccidiosis comprising the recombinant 82 kDa antigen.

The present invention provides the cloning and sequencing of two of the major *Eimeria maxima* gametocyte antigens having molecular weights of 56 and 82 kDa.

The production of gametocytes was scaled-up in order to isolate enough gametocyte antigen to carry out amino acid sequencing (i.e. milligram quantities of the specific antigens) on the 56 and 82 kDa glycoproteins themselves. This scale up production was in itself a very difficult task, and required infecting several thousand chickens in order to provide enough material for carrying out sequence analyses. After achieving this goal, it was possible to produce enough affinity purified gametocyte antigen (APGA) to start isolating the two glycoproteins on a large scale.

The purified gametocyte antigenic glycoproteins were separated by two-dimensional, SDS polyacrylamide gel electrophoresis. After analysis of the two-dimensional gels by staining, the position of the 56 and 82 kDa antigens was determined by transfer to a PVDF membrane filter and immunodetection using antisera to APGA. After identification and removal of the 56 and 82 kDa antigens from the filter, amino acid sequencing of both their N-termini as well as internal protein sequences obtained from tryptic peptides was performed. These peptide sequences were used to predict the DNA sequences, based on which small, specific oligonucleotide probes were synthesized.

The specific oligonucleotide probes were used in RACE PCR (rapid amplification of cDNA ends) to prepare cDNA molecules from the gametocyte RNA that encodes the 56 and 82 kDa antigens. This method allowed for the production of full length cDNA molecules that are specifically amplified from mRNA molecules that contain within them the RNA sequences that encode the desired peptides. This cDNA product was then fully sequenced and the presence of the various peptides sequenced above was confirmed. Surprisingly, we found that the cDNA clones we obtained were not related to those described in Wallach et al., U.S. Pat. No. 5,932,225. Therefore, it appears that in Wallach et al., artifacts occurred when screening the cDNA library with antibodies and the clones thought to encode the 56 and 82 kDa antigens which were isolated did not in fact encode these antigens.

Finally the two new cDNA clones were used as a probe in Southern and northern blotting experiments to identify the specific gene(s) and mRNA molecule(s) that encode for the 56 and 82 kDa antigens. Whereas previously no clear banding patterns could be obtained on blots (U.S. Pat. No. 5,932,225), the number and size of gene fragments and mRNA transcripts that encode for the two antigens were clearly discerned.

The present invention further provides a method for cloning the 56 and 82 kDa antigens into a bacterial expression vector, pTrcHis, containing a poly his tag (to aid in the purification of the recombinant antigens). The two genes are then expressed in *E. coli* by adding a specific inducer molecule (isopropyl-α-D-thiogalactopyranoside), followed by the identification of the recombinant 56 and 82 kDa antigenic proteins by western blotting. The results of these blots showed that the 56 and 82 kDa recombinant antigens had the correct size based on measurements by mass spectrometry, and were recognized by antibodies to the his tag as well as protective antisera raised against the native 56 and 82 kDa gametocyte antigens. These results confirmed the identity of the clones and showed that these recombinant antigens can be used to replace the native antigens in the maternally based vaccine against coccidiosis in chickens.

The present invention further describes the relationship between the 56 kDa gametocyte antigen with a 30 kDa oocyst protein. This oocyst protein was shown, by immunoblotting, to strongly react with antiserum against the 56 and 82 kDa gametocyte antigens. By sequencing the amino terminus of the 30 kDa oocyst protein, we found that there was a precise match with the amino terminus of the 56 kDa antigen. It was therefore concluded that the 56 kDa antigen is processed during the development of oocysts from gametocytes into the 30 kDa protein.

The invention is further illustrated by the following examples which in no way should be construed as being further limiting. One skilled in the art will readily appreciate that the specific methods and results discussed are merely illustrative of the invention as described more fully in the claims which follow thereafter.

EXPERIMENTAL DETAILS

Example 1

Purification of *Eimeria maxima* Gametocytes on a Large Scale

In order to produce very large quantities of gametocytes, 4,000 heavy breed chickens were infected with 10,000 sporulated *E. maxima* oocysts, and were then sacrificed on day six (about 134 hours) post infection. The chicken intestines were removed, washed with PBS and cut open longitudinally. They were then cut into 1 cm long pieces and placed in a SAC buffered solution (170 mM NaCl, 10 mM Tris pH 7, 10 mM glucose, 5 mM $CaCl_2$, 1% powdered milk) containing 0.5 mg/ml hyaluronidase (Type III from Sigma, 700 units/mg). The intestinal pieces were incubated at 37° C. for 20 minutes after which they were placed on top of a gauze filter. The pieces were rinsed with large quantities of SAC buffer and the resulting filtrate was collected. This was then filtered through a 17 micron polymon filter (Swiss Silk Bolting Cloth Mfg. Co. Ltd., Zurich, Switzerland) and the resulting filtrate was then filtered through a 10 micron filter. The gametocytes were collected from the top of the 10 micron filter, examined and counted microscopically, and placed in centrifuge bottles, which were spun at 800×g for 10 minutes. The gametocytes were then washed twice with SAC buffer, and frozen at −70° C.

Example 2

Purification of the 56, 82 and 230 kDa Gametocyte Antigens

The frozen gametocytes were thawed at room temperature and the proteins were extracted as described previously (Wallach 1995). The 56 and 82 kDa gametocyte antigens were isolated from the protein extract by running it over a Sepharose 4B column containing the monoclonal antibody 1E11-11 raised against the 56 kDa antigen. A complex of the gametocyte antigens were allowed to bind to the monoclonal antibody attached to the resin, the non-specific material was washed off using buffer, and the affinity purified gametocyte antigens (APGA) were eluted from the column. The purified APGA was lyophilized. A small sample of APGA was analyzed by SDS-PAGE where the 56 and 82 kDa native antigens were clearly visualized (FIG. 1).

Example 3

Figure 3:
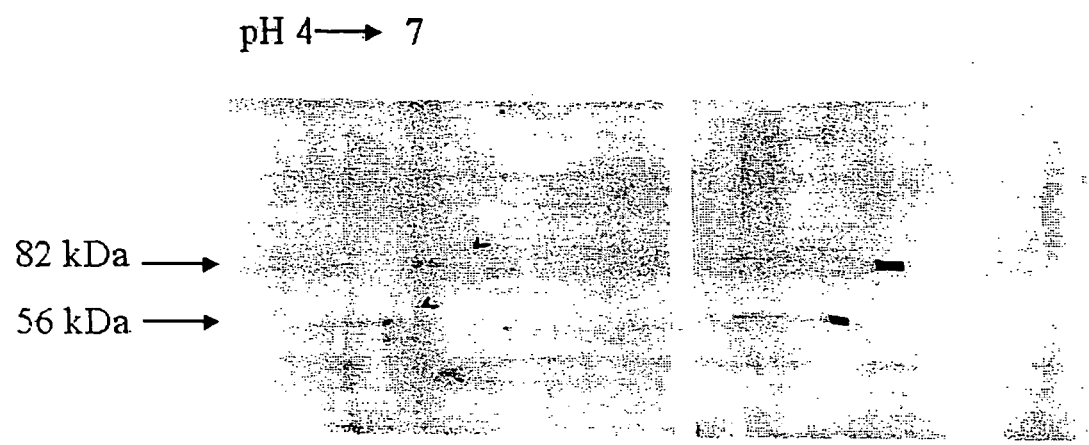
FIG. 3 depicts a Coomassie stained PVDF filter from a two-dimensional SDS PAGE gel and the identification of the spots that were cut out for sequence analysis. Arrows point to the 56 and 82 kDa native antigens.

Two Dimensional Gel Electrophoresis of APGA and Isolation of the Major 56 and 82 kDa Antigens The 56 and 82 kDa gametocyte antigens were isolated from APGA. Lyophilized APGA was prepared as described in Example 2, and was solubilized in water. The proteins were then separated by two-dimensional SDS-PAGE (FIG. 2), and identified by immunoblotting using a polyclonal chicken anti-APGA antibody, which recognizes both the 56 and 82 kDa proteins. Once identified and their location established on two-dimensional SDS-PAGE gels, the proteins were then transferred to a PVDF membrane filter, and stained with Coomassie Blue (FIG. 3). Immunoblotting was carried out at the same time, and the two blots were compared to clearly identify the 56 and 82 kDa proteins. The spots corresponding to the 56 and 82 kDa gametocyte antigens were cut out of the membranes and the amino-terminus of each antigen was sequenced.

Example 4

Amino Acid Sequencing of the Amino-Terminus as Well as Internal Tryptic Peptides from the 56 and 82 kDa Antigens The amino-termini of the 56 and 82 kDa proteins were sequenced:

```
amino-terminus of the 56 kDa protein:
VPSTTPVENQVHPY-EM          (SEQ. ID. NO. 7)

amino-terminus of the 82 kDa protein:
-PTVLDTTTG-QVEDT           (SEQ. ID. NO. 8)
```

In order to determine the protein sequence of internal tryptic fragments of the 56 and 82 kDa proteins, the APGA preparation was first separated by one dimensional SDS-PAGE and stained with Coomassie Blue. The proteins were then excised from gels and digested with trypsin and sequenced.

Several tryptic peptide sequences were obtained from both proteins and the results are summarized in Table 1.

described in Example 1. There was a concern that residual chicken intestinal material was still present in this preparation. Consequently, PCRs carried out using degenerate primers designed to the amino-terminus of the 56 and 82 kDa genes and degenerate primers designed to internal tryptic peptide fragments gave rise to bands in both cDNA samples prepared from purified gametocytes and uninfected chicken cells. In this situation PCR bands, which stained intensely with ethidium bromide on agarose gels, were purified, cloned into pGEMT-Easy (Promega) and sequenced (SUPAMAC sequencing service, Sydney, Australia). In some cases, when rearrangements were observed or the cloned fragment was difficult to sequence, sequence was obtained directly from the PCR product. If the DNA sequence data from the PCR product translated to any of the amino acid sequences of the tryptic peptides, the PCR product was of parasitic origin and sequencing continued.

The full length sequence of the 56 and 82 kDa proteins are shown in FIGS. 4 and 5, respectively. The full length sequence of the 230 kDa protein is presented in FIG. 12.

TABLE 1

Amino acid sequences of tryptic peptides isolated from the 56 and 82 kDa antigens.

| Peptide | 56 kDa Antigen | 82 kDa antigen | SEQ. ID. NO. |
|---|---|---|---|
| A | VQDV(L/I)VDA(L/I)WAS(L/I)R | ATGFSEEEVMR | 9, 10 |
| B | VTEMMDM(L/I)SNR | TGGLFDQACNDAPPSR | 11, 12 |
| C | Q(L/I)Q(L/I)QDQMMR | TGP(L/I)STTGATGATTGPVAA(L/I)R | 13, 14 |
| D | AAEEF(L/I)HR | P(L/I)THVE | 15, 16 |
| E |  | R(L/I)AAVPGTTAGT | 17 |
| F | D(L/I)QEY(L/I)STAFNWA-ENQSTAYTR | (L/I)AEGAEPRPVMPPAAATAAANLR | 18, 19 |
| G | RQTAAWMDRTA(L/I)EQEETT |  | 20 |
| H | MNAAMDSSNE(L/I)MTT |  | 21 |
| I | KFPET(L/I)F |  | 22 |

The amino acid sequences obtained did not show any homology to any other known protein.

Example 5

RACE PCR Cloning and Sequencing of the Genes Encoding the 56 and 82 kDa Antigens The genes for the 56 and 82 kDa proteins were amplified from gametocyte cDNA using SMART RACE PCR technology (Clonetech). RNA was isolated from E. maxima gametocytes and mRNA was purified using Dynal beads (Dynal). SMART ready cDNA was synthesized following the protocols according to the manufacturer's instructions using the reverse transcriptase Powerscript (Clonetech). Amplifications of both the 5' and 3' ends were carried out using the protocols described in the SMART RACE PCR manual, and the DNA polymerase, Advantage Taq (Clonetech), a high fidelity enzyme mixture.

The gametocytes had been isolated from chicken intestines, filtered a number of times and washed thoroughly as Amino acid sequence of the tryptic peptides and N-terminus of the 56 gametocyte antigen matched the deduced amino acid sequence arising from the corresponding cloned DNA.

Nine tryptic peptides were sequenced for the 56 kDa protein (Table 1). All peptides but one, sb56i, could be mapped to the cloned gene corresponding to the 56 kDa protein (FIG. 4). This tryptic fragment may correspond to a contaminating band present in the sample. In detail:

Tryptic peptides sb56a, sb56b, sb56c, sb56d, sb56f and sb56h matched precisely to the deduced amino acid sequence predicted by the cloned DNA.

Tryptic peptide sb56g did not match precisely to the deduced amino acid sequence predicted by the cloned DNA. The sequence of the tryptic fragment was reanalysed, and the new sequence matched more closely with the predicted sequence derived from the cloned DNA.

Tryptic fragment sb56g original sequence:

```
RQ--TAAWMDR-TA[L/I]EQEETT    (SEQ. ID. NO. 23)
```

Reanalysed sb56g sequence:

```
RGVQTAAWMDGVTA I EKEETT    (SEQ. ID. NO. 24)
```

Deduced aa sequence from DNA:

```
RGVQTAAWMNGVTA I EKEETT    (SEQ. ID. NO. 25)
```

A discrepancy still remains in this peptide at amino acid 10, where the protein sequence reveals a D and the DNA sequence predicts a N. This segment of DNA was sequenced 4 times, and each time predicted an N.

Amino acid sequence of the tryptic peptides and N-terminus of the 82 gametocyte antigen match the deduced amino acid sequence arising from the corresponding cloned DNA.

Seven tryptic peptides were sequenced for the 82 kDa protein (Table 1). All peptides but two, sb82d and sb82e could be mapped to the cloned gene corresponding to the 82 kDa protein. This tryptic fragment may correspond to a contaminating band present in the sample. In detail:

Tryptic peptides sb82a, sb82b, sb82c, sb56d and sb82f matched precisely to the deduced amino acid sequence predicted by the cloned DNA.

Tryptic peptides sb82d and sb82e did not match to the deduced amino acid sequence predicted by the cloned DNA.

In addition to the sequence information described above:

1) The predicted size of the ORF encoding the mature form of the 82 kDa protein is 64,275 Da, which corresponded to the true size of the native protein of 62,236 Da, as determined by mass spectrometry.

2) The predicted size of the ORF encoding the mature form of the 56 kDa protein is 51,407 Da which corresponded to the true size of the native protein of 52,450 Da, as determined by mass spectrometry.

Finally, the two protein and DNA sequences did not show any homology to any other known gene or protein.

Example 6

Southern and Northern Blotting Using the 56 and 82 kDa cDNA Cloned Probes.

Figure 6:
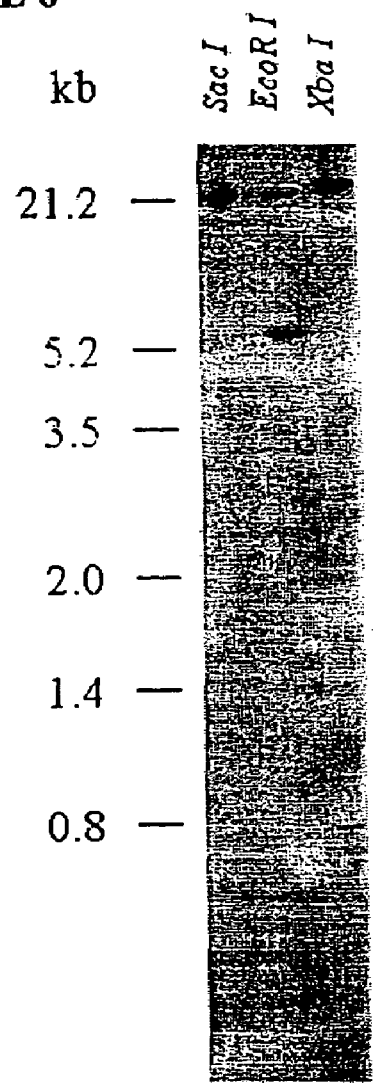
FIG. 6 depicts a Southern blot of gametocyte and control chicken DNA probed with the cDNA clone for the 56 kDa antigen. The restriction enzymes used for digestion of the DNA and the marker band sizes in kilobases are indicated.
Figure 7:
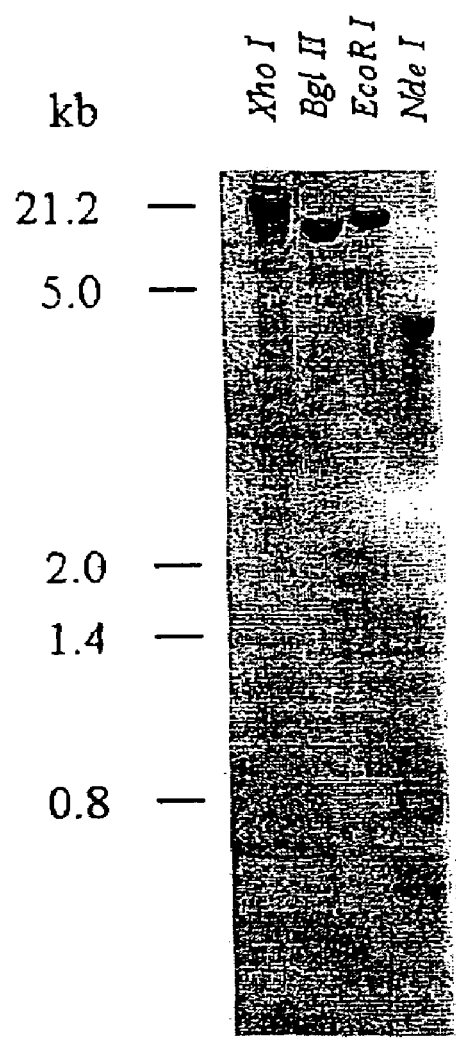
FIG. 7 depicts a Southern blot of gametocyte and control chicken DNA probed with the cDNA clone for the 82 kDa antigen. The restriction enzymes used for digestion of the DNA and the marker band sizes are indicated.

Southern blotting using *E. maxima* and chicken DNA was carried out by first cutting the DNA with a variety of restriction enzymes and separating the resulting DNA fragments on an agarose gel. This is followed by transferring the DNA to nitrocellulose paper, probing with a $P^{32}$ labeled cDNA probe for the 56 (FIG. 6) or 82 (FIG. 7) kDa antigens and performing autoradiography. The results showed that for both the 56 and 82 kDa antigens there appear to be two different, single copy genes, which encodes the two proteins.

Figure 8:
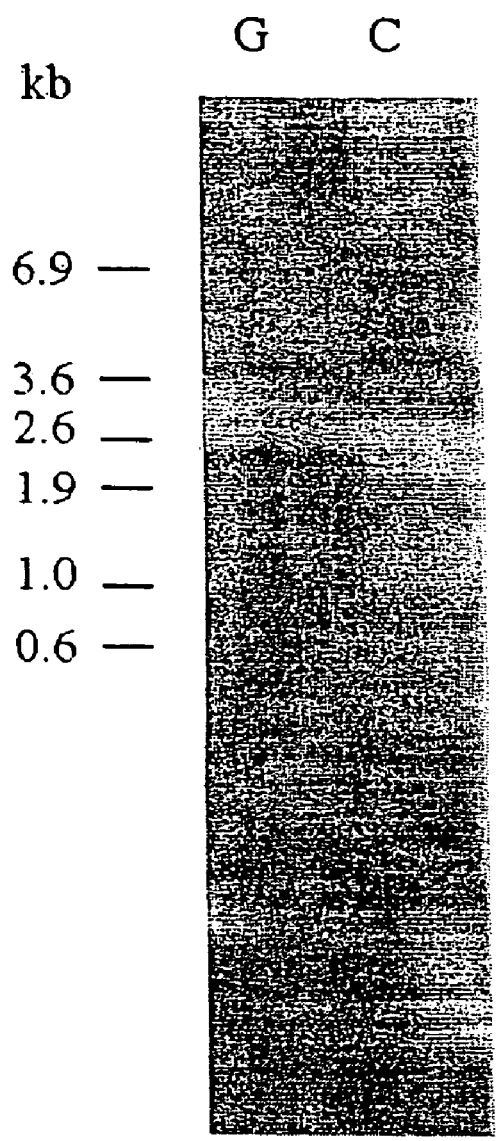
FIG. 8 depicts a northern blot of gametocyte (G) and control (C) chicken total RNA probed with the 82 kDa cDNA clone. The sizes of the marker bands in kilobases are indicated on the left.

Northern blotting using *E. maxima* and chicken RNA was carried out by separating the RNA molecules on an agarose gel, transferring it to a nitrocellulose filter and probing with the $P^{32}$ labelled 56 and 82 cDNA clones. The results showed that the 56 kDa mRNA has a molecular weight of about 1.9 KB and the 82 kDa mRNA had a molecular weight of about 2.4 KB (FIG. 8). These sizes are very similar to those predicted from the DNA sequences.

Example 7

Expression of the Recombinant 56 and 82 kDa Antigens using the pTrcHis Vector in *E. coli* and Their Analysis using Sera Against Native APGA.

The full length gene encoding the 82 kDa protein was amplified from *E. maxima* gametocyte cDNA using gene specific primers carrying terminal restriction sites to facilitate directional cloning into the expression vector pTRCHisb (Invitrogen). The full length gene included the coding region of the amino-terminus of the mature protein and sequence up to, but not including, the stop codon (575 aa). A partial fragment of the gene encoding the 56 kDa protein was amplified from *E. maxima* gametocyte cDNA using gene specific primers carrying terminal restriction sites. This included the amino-terminus of the protein and a further 323 amino acids of sequence, 133 amino acids shorter than the full length mature protein. Both genes were cloned into the commercially available vector pTrcHisb (Invitrogen).

1) Expression of the 56 kDa Gene in pTrcHis B

Transformed bacteria were induced with 1 mM IPTG, and bacterial lysates were analyzed by 1D-SDS PAGE and immunoblotting (FIG. 9). A commercially available anti-His antibody to the His fusion tag of the recombinant protein recognized a band of the predicted size of 40 kDa (this clone lacks the coding region for 133 amino acids) under inducing conditions. Under non-induced conditions there was also a low level of reactivity with this band indicating that there is some degree of leakiness of the gene expression. Recognition of the recombinant 56 kDa protein was then assessed by immunoblotting with the chicken polyclonal anti-APGA antibody. The immunoblot showed that the anti-APGA antibody recognized the native form of the protein by one dimensional SDS-PAGE, as well as the recombinant protein, clearly demonstrating that the cloned gene product indeed codes for the 56 kDa protein.

2) Expression of the 82 kDa Gene in pTrcHis B

Figure 10:
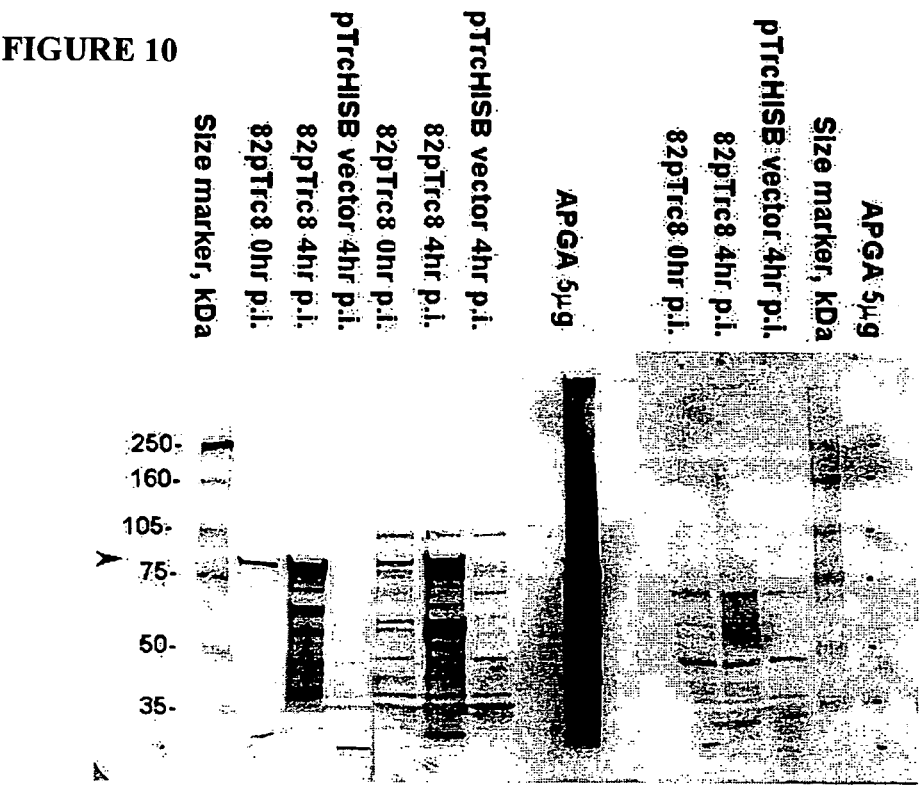
FIG. 10 depicts a Coomassie stained gel and immunoblot of proteins from bacteria containing pTrcHisB-82 kDa cDNA cloned plasmids. The immunoblot shows reactivity of the anti polyhistidine, chicken anti-APGA as well as uninfected chicken (negative control) sera with the 82 kDa recombinant protein under IPTG induced and non-induced conditions at various times after induction. As a negative control, the experiment was also performed using bacteria transformed with the same plasmid without an insert. As a positive control, native APGA is also run. The arrow shows the position of the 82 kDa recombinant protein. The sizes of the protein marker bands are indicated on the left.

Transformed bacteria were induced with 1 mM IPTG, and bacterial lysates were analysed by one dimensional SDS PAGE and immunoblotting (FIG. 10). A commercially available anti-His antibody to the His fusion tag of the recombinant protein recognized a band of the predicted size of 82 kDa under inducing and non-inducing conditions. Recognition of the recombinant 82 kDa protein was then assessed by immunoblotting with the chicken polyclonal anti-APGA antibody. This antibody was produced by immunizing chickens with native APGA isolated from purified gametocytes. The immunoblot showed that the anti-APGA antibody recognized the native form of the protein by 1D SDS-PAGE, as well as the recombinant protein, clearly demonstrating that the cloned gene product indeed codes for the 82 kDa protein.

Based on the above results together with the sequence analyses described in Example 5, we concluded that the two cDNA clones described above are the authentic genes encoding for the 56 and 82 kDa antigens. In addition, the strong reactivity with the antisera raised against the native antigens shows that these recombinant proteins can now be used to replace APGA for the immunization of chickens against coccidiosis.

Example 8

Homology of the 56 kDa Antigen With a 30 kDa Antigen from *E. maxima* Oocysts.

Figure 11:
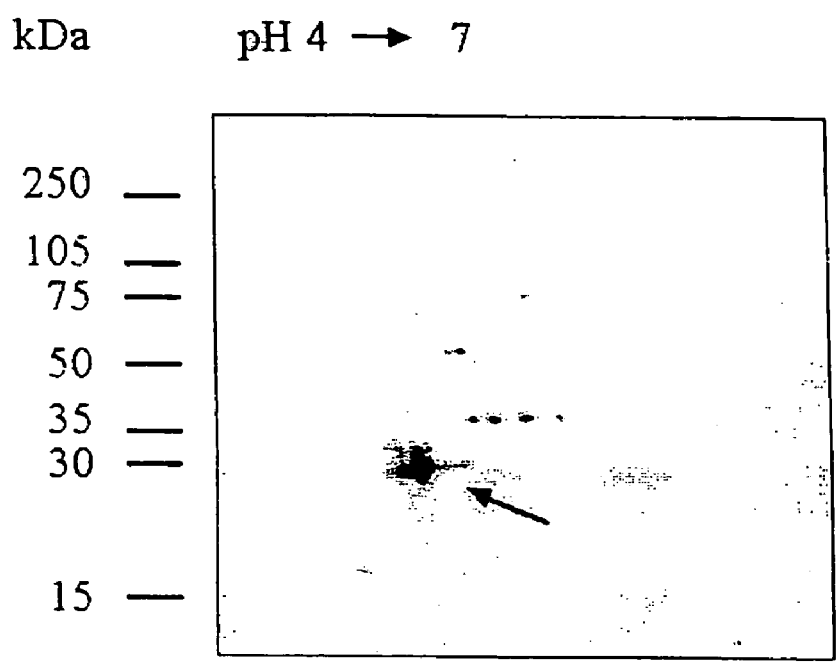
FIG. 11 depicts an immunoblot of a whole lysate of unsporulated *E. maxima* oocysts separated by 2 dimensional SDS PAGE. The gel was blotted onto a membrane filter and probed with an antiserum raised against APGA. The strongly reacting 30 kDa spot is shown with an arrow. This was the spot that was cut out of the gel and used for sequence analysis.

Antibodies to APGA were used to detect homologous proteins on a two-dimensional blot of oocyst antigens. We found that there was very strong reactivity with a protein of 30 kDa (FIG. 11). This spot was cut out of the membrane filter and the N-terminus of the protein was sequenced. The resulting amino acid sequence corresponded precisely to the N-terminal sequence of the gametocyte 56 kDa antigen. Based on this finding we concluded that the gametocyte 56 kDa antigen is processed into the 30 kDa protein of the oocyst stage of development.

Example 9

Expression of gam 56, a 56 kDa Gametocyte Antigen from *Eimeria maxima*
Native protein: Mr 56,000 (size determined by molecular sizing (MS): 52,450 Da)
Source: Parasitic: *Eimeria maxima*
Life cycle stage: macrogametocyte
Gene: 1,754 base pairs sequenced presented over 5 polymerase chain reaction (PCR) fragments, all of which are cloned into pGEMT-Easy, except for the last ~600 bp of the gene, which includes ~400 bp of the coding region.
5'UTR(1-102 bp)
ORF (103-1,533 bp)
3'UTR (1,534-1,731 bp)
polyA tail(1,732-1,754 bp)
pI: 4.8 predicted from sequence (by 2D SDS-PAGE, the protein migrates towards the acidic end of the gel)

Expression Constructs
Expression vectors used: pTRCHisb, pET25b
Expression construct: given p56TRCHisb1
Gene fragment that was cloned into the expression vector: gam 56 was amplified from cDNA using the following primer pairs: SB74/SB75 (172-1137 bp) for directional cloning into the BamHI/EcorI site of TRCHisb. The amplified region contains the sequence encoding the amino terminus of the mature protein, excluding the initiator methionine and leader sequence. It contains a tyrosine-serine rich region and excludes a proline-methionine rich region.
Amino acid composition of cloned gam 56 fragment:
2 cysteines present
amino acid composition of gene fragment cloned into pTRCHisb:

| S(12.7%) | Y(11.5%) | A(8.7%) | T(8.4%) | P(7.2%) |
| R(6.6%) | E(6.0%) | M(5.5%) | L(5.5%) | V(4.6%) |
| Q(4.3%) | N(4.3%) | G(3.8%) | D(3.5%) | W(1.7%) |
| F(1.4%) | K(1.4%) | I(1.4%) | H(0.9%) | C(0.6%) |

Predicted protein size: 41 kDa
Yield: 0.9-1.4 µg/ml (nickel agarose purified protein/ml culture) Difficult to see induced protein in crude bacteria lysate on a Commassie Blue stained gel.

Expression Conditions:
The promoter is leaky, therefore we can get expression in the absence of IPTG.
Used baffled flasks, 37° C., 4 h induction, with 1 mM IPTG, 0.1 mg/ml ampicillin in 0.01 M $Mg^{2+}$SOB(SOB better than LB).
Normally, one predominate band at ~42 kDa is obtained after purification and detection with silver staining. Often some higher molecular weight bands, which may be aggregates, are obtained after purification as well as the main ~42 kDa band. The protein seems to aggregate at −20° C. and 4° C.; after purification we desalt and add stabilisers (3% lactose, 1% monosodium glutamate).

Example 10

Immunization and challenge trial of the recombinant 56 kDa (r56) and 82 kDa (r82) gametocyte antigens, and the 250 kDa (r250) asexual stare antigen in chickens Immunization Animals
Chickens:
84 day old (~12 weeks) Australorp cockerels
kept on medicated (robenidene) food
all chickens were individually tagged and recorded Antigens
Recombinant proteins in the pTRCHisb expression system were grown at 37° C. in 0.1 mg/ml ampicillin in 0.01M $Mg^{2+}$SOB and induced for 4 hours with 1 mM IPTG. Proteins were purified on a Ni-agarose column, concentrated, desalted, and lyophilized with stabilizers (3% lactose, 1% monosodium glutamate). Protein concentrations used for all antigens were measured using the Bradford assay. Affinity Purified Gametocyte Antigen (APGA) preparations provided by M. Wallach was used as a positive control for the trial.

Groups and Doses
9 chickens used per group; 9 groups in total; 81 chickens used in total.
Chickens were immunized with 0.5 ml antigen/Freunds Incomplete Antigen (FIA) cocktail (0.25 ml antigen/ 0.25 ml FIA) per bird, intra-muscularly, on one side only of the chicken, with the following antigens:

| Group 1 | PBS only |
| Group 2 | Adjuvant (FIA)/PBS |
| Group 3 | APGA (2.5 g) |
| Group 4 | r250 protein (1.0 g) |
| Group 5 | r250 protein (10.0 g) |
| Group 6 | r56 protein (0.5 g) |
| Group 7 | r56 protein (5.0 g) |
| Group 8 | r82 protein (0.5 g) |
| Group 9 | r82 protein (5.0 g) |

Immnization Schedule

| Immunization 1: | week 1 |
| Immunization 2: | week 3 |
| Bleed: | week 6 |
| Bleed: | week 8 |
| Bleed/Kill: | week 9 |

Figure 14A:
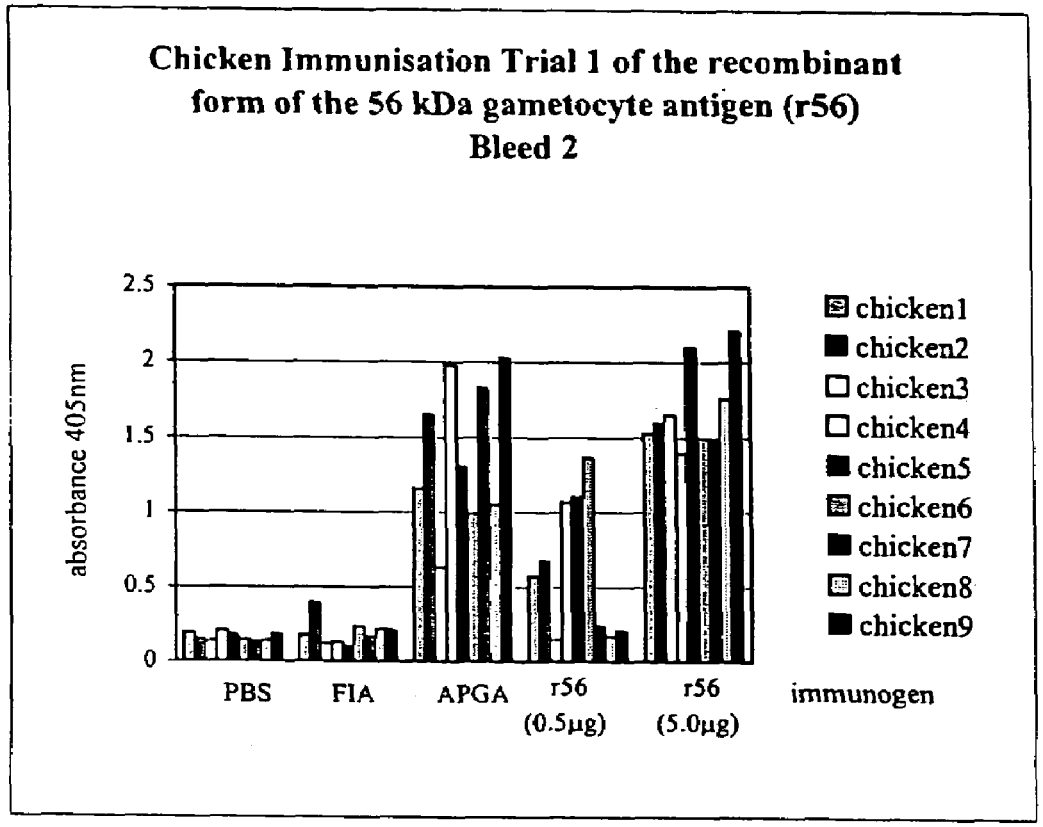
FIGS. 14A & B ELISA results for chicken immunogenicity trial of the recombinant form of the 56 kDa and 82 kDa gametocyte antigen. All serum samples were tested at 1:1000 dilution. A) Coating antigen: APGA to test sera against APGA; r56 purified to test sera taken from chickens immunized with PBS, FIA and the two doses of r56. B) Coating antigen: APGA to test sera against APGA; r82 purified protein to test sera taken from chickens immunized with PBS, FIA and the two doses of r82.
Figure 14B:
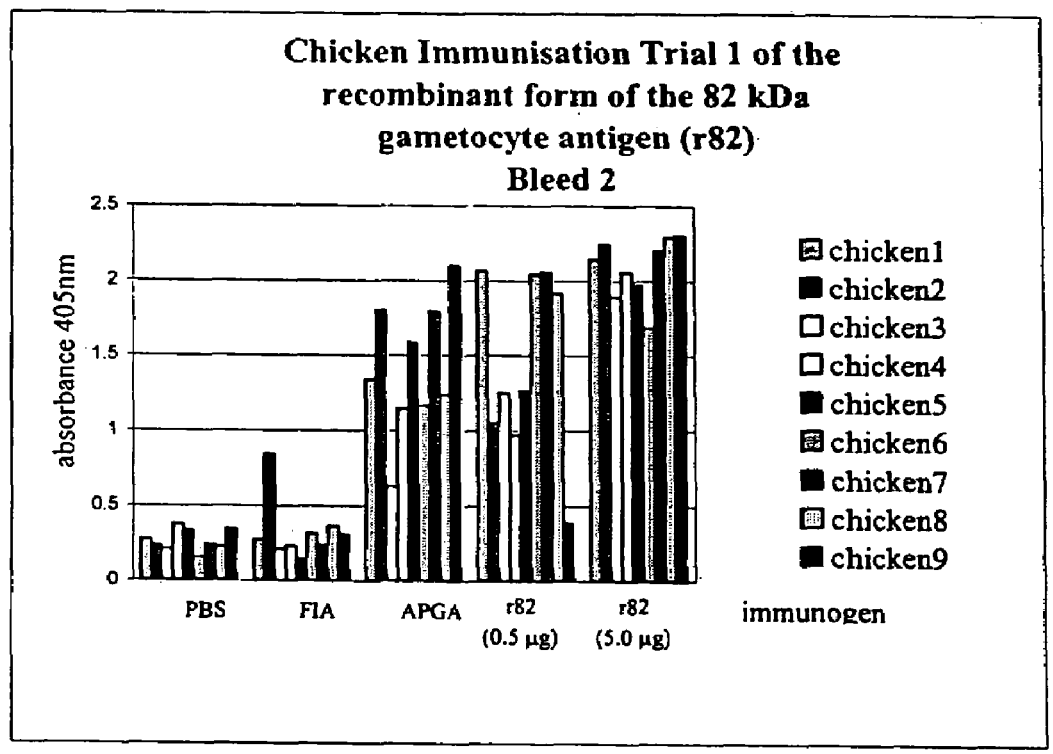

Analyzes
Bleeds were taken (~1.5-2 ml/bird), sera separated and tested by ELISA and immunoblotting Results
Results of the bleeds are shown in FIG. 14.

Challenge

Animals and Parasites
5 chickens (148 days old; ~4.5 months) from each group which had the highest antibody titre based on the ELISA results of bleed 1 were used; in the case of the PBS and FIA controls, chickens with the lowest antibody titres were used

*E. maxima* (strain Houghton);
robenidene was removed from the feed one week prior to challenge Groups The following groups and chickens were taken from the immunization trial described above, and used in the challenge experiments

| Group 1 | PBS only | chicken numbers 2, 3, 4, 6, 8 |
| Group 2 | Adjuvant (FIA)/PBS | chicken numbers 12-16 |
| Group 3 | APGA (2.5 g) | chicken numbers 20, 22, 23, 25, 27 |
| Group 5 | r250 protein (10.0 g) | chicken numbers 37, 39, 41, 44, 45 |
| Group 7 | r56 protein (5.0 g) | chicken numbers 57, 59, 60, 61, 63 |
| Group 9 | r82 protein (5.0 g) | chicken numbers 74, 75, 76, 79, 80 |

Challenge Schedule
Robenidene removed
Challenged with 100 sporulated oocysts per bird Day 6

Oocyst Harvest and Count Schedule
Day 0 post-infection
Day 1 post-infection
Day 2 post-infection
Day 3 post-infection
Day 4 post-infection
Checked oocyst output for contamination of another species
Replaced plastic sheet to start collections.
Day 5 post-infection Feces collected, and oocysts counted
Day 6 post-infection Feces collected, and oocysts counted
Day 7 post-infection Feces collected, and oocysts counted
Day 8 post-infection Feces collected, and oocysts counted
Day 9 post-infection Feces collected, and oocysts counted
Day 10 post-infection Feces collected, and oocysts counted The area was chosen for a number of reasons and are as follows: 1) similar 3' hydrophilic tail regions have been identifiied in a number of apicomplexan microneme proteins and appear unique to this family of proteins; 2) such regions have been identified in other microneme proteins also recognised as immunodominant, primarily *Eimeria tenella* microneme protein 1 (EtMIC1) and surface antigen 5401 (EtMIC4); 3) a similar region was expressed from the *E. tenella* 5401 antigen (EtMIC4) and was found to afford significant protection against challenge with *E. tenella* (Danforth et al, 1988); 4) other regions of the protein consist primarily of the EGF-like and TSP-1-like domains. These domain types are found highly conserved within eukaryotes and therefore the possibility of their inducing auto-immunity must be considered. Furthermore because of the prevalence of such domain types it seems unlikely that they would be responsible for inducing a strong immune response.

PCR primers EP006 (5'-TTGGATCCCGAATTGCAC-CCCA TTCC-3') and EP007 (5'-TTGAATTCTGAAT-GTCGCCGCTGTCG-3') were designed to amplify the selected DNA region from a cDNA clone encoding the 250 kDa protein. The primers incorporated BamHI (EP006) and EcoRI (EP007) restriction sites to facilitate cloning into the selected expression vector. The PCR product subsequently generated using the primers was gel-purified and its identity confirmed by sequencing.

The bacterial expression vector pTrcHisB (Invitrogen) was selected for expression studies. Plasmid vector DNA and gel purified cDNA insert were digested with the restriction enzymes BamHI and EcoRI, and the digested DNA fragments gel purified and ligated. The ligation mixture was transformed into *E. coli* strain DH5-a and following plating and incubation, resulting colonies were selected, cultured and used for plasmid preparation. The identity of the selected recombinants was confirmed by DNA sequencing.

In preparation for expression, plasmid DNA containing the expression construct was transformed into the *E. coli* host expression strain TOP10. Following plating and incubation, a single bacterial colony was selected and used to establish an O/N culture in LB media. A vector only negative control culture was also established. Aliquots of each culture were

TABLE 2

Immunization and Challenge Trial I

| Groups/ | Cumulative oocyst counts (×10$^6$) | | | | | Output (%) | | | | | % inhibition | | | | |
|---|---|---|---|---|---|---|---|---|---|---|---|---|---|---|---|
| Day p.i. | 6 | 7 | 8 | 9 | 10 | 6 | 7 | 8 | 9 | 10 | 6 | 7 | 8 | 9 | 10 |
| 1. PBS only | 6.67 | 17.00 | 26.40 | 27.33 | 27.43 | 100 | 100 | 100 | 100 | 100 | 0 | 0 | 0 | 0 | 0 |
| 2. FIA only | 3.20 | 14.40 | 17.30 | 17.50 | 17.50 | 48 (100) | 85 (100) | 66 (100) | 64 (100) | 64 (100) | 52 (0) | 15 (0) | 34 (0) | 36 (0) | 36 (0) |
| 3. APGA (2.5 µg) | 2.77 | 9.35 | 13.48 | 13.58 | 13.61 | 42 (87) | 55 (65) | 51 (78) | 50 (78) | 50 (78) | 58 (13) | 45 (35) | 49 (22) | 50 (22) | 50 (22) |
| 5. r250 (10 µg) | 0.83 | 8.35 | 13.72 | 14.72 | 14.72 | 12 (26) | 49 (58) | 52 (79) | 54 (84) | 54 (84) | 88 (74) | 51 (42) | 48 (21) | 46 (16) | 46 (16) |
| 7. r56 (5 µg) | 0.33 | 4.53 | 7.20 | 8.16 | 8.53 | 5 (10) | 27 (32) | 27 (42) | 30 (47) | 31 (49) | 95 (90) | 73 (68) | 73 (58) | 70 (53) | 69 (51) |
| 9. r82 (5 µg) | 4.23 | 10.33 | 14.73 | 14.93 | 15.06 | 63 (132) | 61 (72) | 56 (85) | 55 (85) | 55 (86) | 37 (0) | 39 (28) | 44 (15) | 45 (15) | 45 (14) |

Example 11

Expression of a Recombinant Fragment of the 250 kDa Asexual Stage Protein

The region of the 250 kDa protein encoding the predicted transmembrane domain/cytosolic tail and upstream hydrophilic domain was selected for expression studies (FIG. 15).

then transferred to fresh LB media and incubated until the cells reached mid-log phase, at which stage expression was induced with the addition of 1 mM IPTG. Samples from the expression culture and negative control culture were taken at 0, 1, 2, 5 and 24 hrs post induction, and centrifuged to pellet the bacterial cells. All pellets were subsequently resuspended in TE buffer, sonicated and centrifuged to separate the aqueous soluble fraction (supernatant) from the insoluble fraction (pellet). All fractions were analysed under reducing conditions on SDS-PAGE gels and subsequently stained with Coomassie Blue. When compared to the negative control samples, an over-expressed protein was detected in the soluble fractions, migrating at just below the 45 kDa marker. Western analyis of the soluble fractions using an antibody reactive with the 6× Histidine tag of pTrcHis expression products, detected a protein band of the same apparent molecular weight. The predicted size of the expressed protein is approximately 30 kDa, somewhat less than that observed on SDS-PAGE gels. The size difference might be explained by the high frequency of proline residues in the expressed protein, known to cause proteins to migrate with apparently high molecular weight.

In preparation for immunogenicity trials, the expressed protein was purified using Ni-NTA Agarose nickel-charged resin (QIAGEN), with minor modifications to the manufacturer's recommended protocol. Expressed proteins containing the 6× His tag bind to the resin and are displaced by an increased concentration of imidazole in the elution buffer. Briefly, cell pellets were resuspended in Lysis buffer (50 mM $NaH_2PO_4$, 300 mM NaCl, 10 mM imidazole, pH 8.0), containing 1 mg/ml lysozyme. The suspension was sonicated on ice and centrifuged to pellet insoluble material. The supernatant containing the soluble expressed protein was then mixed with Ni-NTA resin and added to a disposable elution column. The slurry was allowed to settle then washed with Wash buffer (50 mM $NaH_2PO_4$, 300 mM NaCl, 20 mM imidazole, pH 8.0), before elution with Elution buffer (50 mM $NaH_2PO_4$, 300 mM NaCl, 250 mM imidazole, pH 8.0). The purity of eluted fractions was analysed by reducing SDS-PAGE and Coomassie Blue staining.

Figure 16:
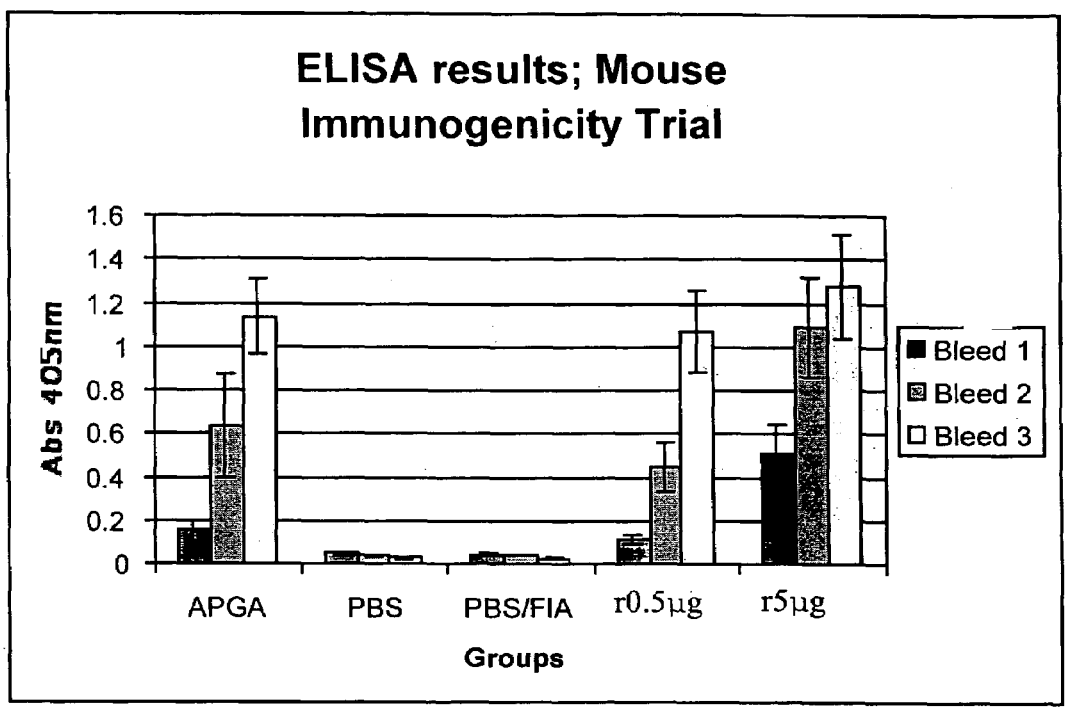
FIG. 16 Mouse immunogenicity trial of the recombinant fragment of the 250 kDa asexual stage protein. The average of each group for the three consecutive bleeds is shown, with standard error bars indicated. All serum samples were tested at 1:1000 dilution. Coating antigen was 100 ng of APGA for sera from the positive control APGA group, or 100 ng of the recombinant protein for the negative control PBS and PBS/FIA groups and the two recombinant protein doses (r0.5 µg and r5 µg)
Figure 17:
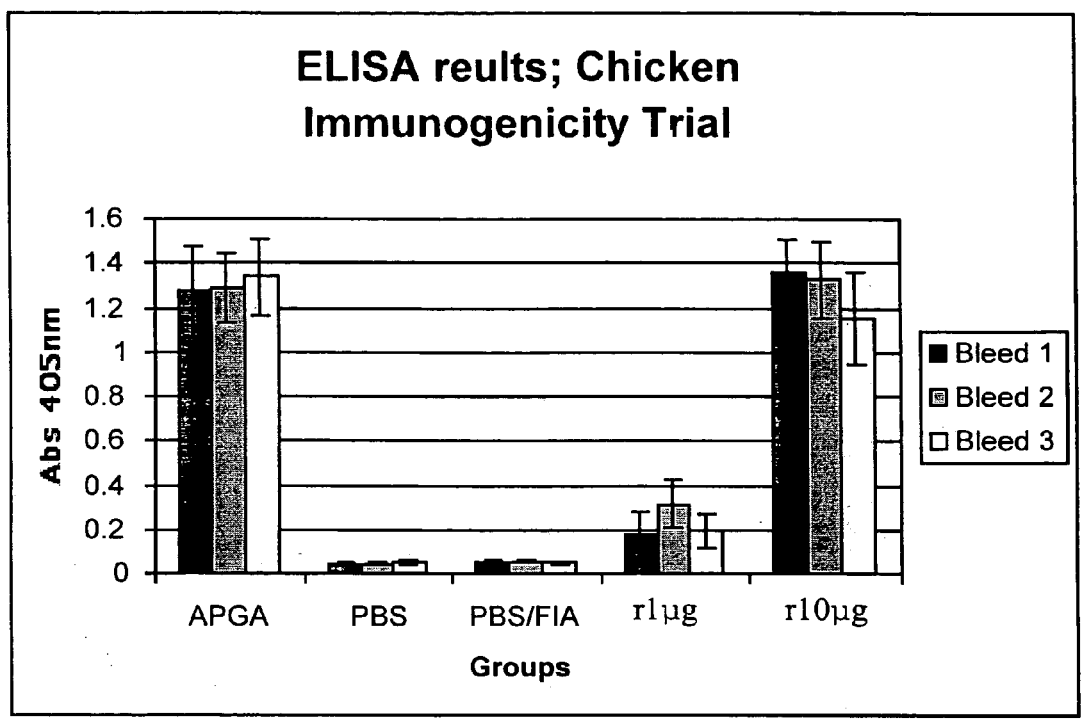
FIG. 17 Chicken immunogenicity trial of the recombinant fragment of the 250 kDa asexual stage protein. The average of each group for the three consecutive bleeds is shown, with standard error bars indicated. All serum samples were tested at 1:1000 dilution. Coating antigen was 100 ng of APGA for sera from the positive control APGA group, or 100 ng of the recombinant protein for the negative control PBS and PBS/FIA groups and the two recombinant protein doses (1 82 g and r10 82 g).

Details for the immunogenicity trials are as for the 56 kDa and 82 kDa trials. For the mouse trial, 0.5 μg and 5 μg doses of the recombinant protein per mouse were used (6 mice/group). For the chicken trial, 1 82 g and 10 82 g doses per bird were used (9 chickens/group). ELISA results for the collected serum samples from the mouse and chicken trials are presented in FIGS. 16 and 17 respectively.

Example 12

The oocyst wall of *Eimeria* is derived from precursor proteins found in the sexual stage of the parasite (macrogametocyte) which undergo processing and di-tyrosine crosslinking to form the hardened, protective barrier of the excreted form of the parasite The genes encoding the 56 kDa and 82 kDa sexual stage, macrogametocyte antigens have been cloned and sequenced. Both genes show an unusual amino acid composition, and in particular, both have tyrosine-rich regions; the 56 kDa protein possesses one tyrosine-rich region and the 82 kDa protein possesses two tyrosine-rich regions. Proteins rich in tyrosine have been previously implicated in oocyst wall formation in *E. acervulina* and *E. tenella*. (Eschenbacher et al.) Thus, the role of the tyrosine rich region in the 56 kDa and 82 kDa sexual stage antigens in oocyst wall formation was explored in *Eimeria maxima*.

Figure 18:
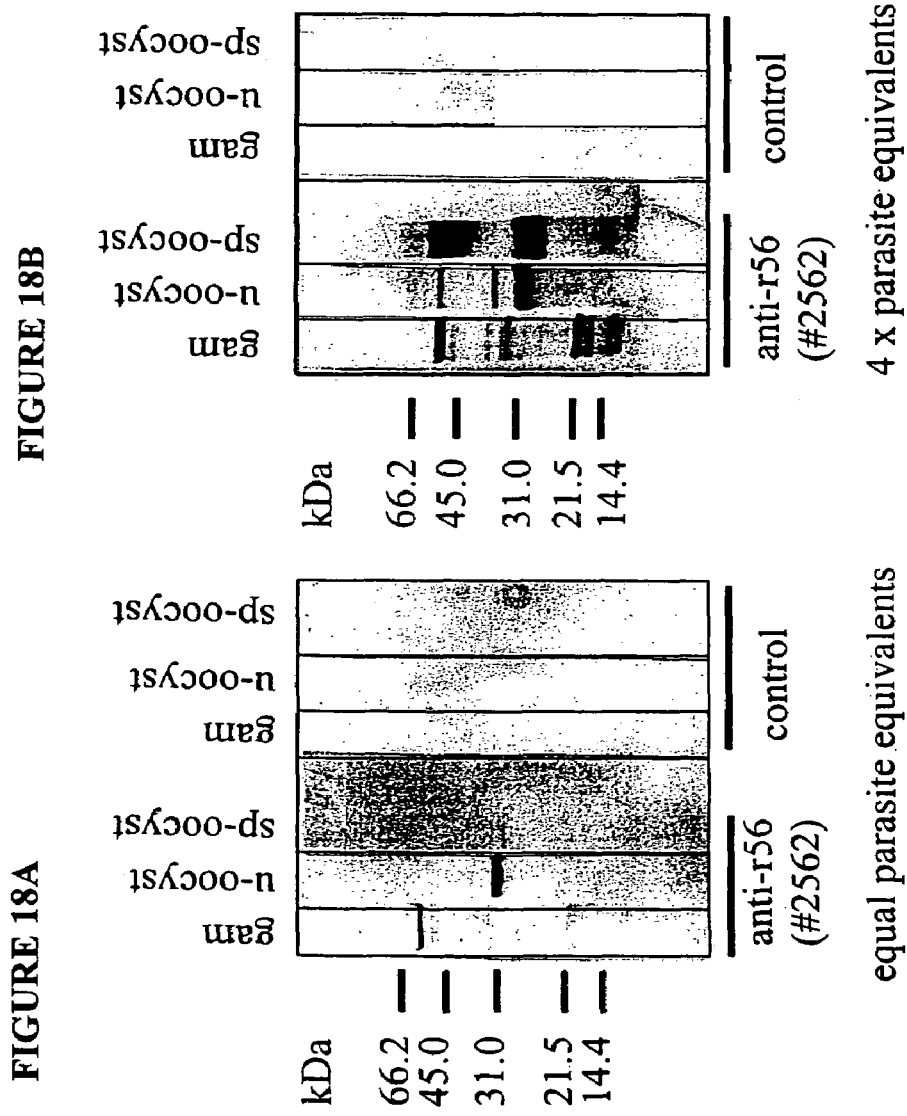
FIG. 18 Anti-r56 recognition of gametocyte and wall antigens in *Eimeria maxima*.

Antibodies to the recombinant form of the 56 kDa protein (anti-r56) and antibodies to the recombinant form of the 82 kDa protein (anti-r82) recognize a ~30 kDa protein in unsporulated and sporulated oocysts, and a ~30 kDa protein in purified wall fragments (see FIGS. 18 and 19). They also recognize their native form counterparts in gametocyte extracts. The ~30 kDa protein recognized in purified oocyst wall fragments by the anti-r82 kDa antibody is not the same as the ~30 kDa protein recognized by the anti-r56; it is slightly smaller. The ~30 kDa protein recognized by the anti-r56 antibody was purified and the N-terminus sequenced. The N-terminus of the ~30 kDa protein corresponds exactly to the N-terminus of the 56 kDa gametocyte antigen (see FIG. 20*a*).

Others have shown by SDS-PAGE and coomassie blue staining that the oocyst wall of *Eimeria* is composed of two predominant proteins of 14 kDa and 30 kDa. Using better SDS-PAGE separation techniques, we have resolved the 14 kDa protein into 3 components of ~10-14 kDa, and named them 14.1, 14.2 and 14.3, where 14.1 represents the protein which has migrated the slowest on SDS-PAGE gels, and 14.3 the fastest (see FIG. 18*c*). We have sequenced the N-terminus of all four proteins and the results are presented in FIG. 20. In summary, the 30 kDa protein is a novel protein which does not show any similarity to any other previously characterized protein as determined through a BLAST protein search (see FIG. 20*c*). The N-terminus of protein 14.3 corresponds to the beginning of the tyrosine rich region in domain 1 of the 82 kDa protein (see FIG. 20*b*), the N-terminus of protein 14.2 corresponds to the beginning of the tyrosine rich region in domain 2 of the 82 kDa protein (see FIG. 20*b*), and the N-terminus of protein 14.1 corresponds to the beginning of the tyrosine rich region in the 56 kDa protein (see FIG. 20*a*).

Together these results show that the oocyst wall of *Eimeria* is derived from precursor proteins found in the wall forming bodies of the sexual stage (macrogametocyte) of the parasite. Through some signaling mechanism, they are proteolytically processed into several shorter proteins of ~30 kDa and ~14 kDa. Contrary to previous findings, our data indicates that the oocyst wall is composed of more than two proteins. Our findings suggest that the oocyst wall is composed of several proteins present at different levels in the parasite, some of which are in high abundance that they are recognized by coomassie blue staining of SDS-PAGE gels, and others that are present at low levels, only detected through the more sensitive technique of immunoblotting. The ~30 kDa protein seen in coomassie blue stained SDS-PAGE gels is not related to the 56 kDa and 82 kDa gametocyte antigens, however, the smaller ~10-14 kDa proteins are. Our most recent finding that di-tyrosine is present at detectable levels in the order of 0.00338 mmol/mol in oocysts, indicates that the small tyrosine rich proteins are probably held in the wall through a mechanism involving di-tyrosine crosslinks. However, we believe that not all the proteins are held in the wall in this way and are currently investigating this.

REFERENCES

Eschenbacher, K. H., Eggli, P., Wallach, M. and Braun, R. (1995) Characterization of a 14 kDa oocytst wall protein of *Eimeria tenella* and *E. Acervulina*, Parasitol., 112:169-176.

Fried, M., Mencher, D., Sar-Shalom, O., and Wallach, M. (1992) Developmental gene expression of a 230-kilodalton macrogamete-specific protein of the avian coccidial parasite, *Eimeria maxima*. Mol. & Biochem. Parasitol., 51:251-262.

Mencher, D., Pugatsch, T. and Wallach, M. (1989) Antigenic proteins of *Eimeria maxima* gametocytes: cell-free translation and detection with recovered chicken serum. Exp. Parasitol. 68:40-48.

Wallach, M., Pillemer, G., Yarus, S., Halabi, A., Pugatsch, T. and Mencher, D. (1990) Passive immunization of chickens against *Eimeria maxima* infection with a monoclonal antibody developed against a gametocyte antigen. Infection & Immunity 58:557-562.

Wallach, M., Smith, N. C., Petracca, M., Miller, C. M. D., Eckert, J. and Braun, R. (1995) *Eimeria maxima* gametocyte antigens: potential use in a subunit maternal vaccine against coccidiosis in chickens. Vaccine, 13:347-354.

Wallach, M. and Vermeulen, A., (1996) Progress Towards a Subunit Vaccine Against Coccidiosis. Misset's World Poultry, Supplement Coccidiosis (2), 22-24.

What is claimed is:

1. An isolated nucleic acid sequence comprising a nucleotide sequence encoding a 56 kDa polypeptide having the amino acid sequence set forth as SEQ. ID. NO. 3 present in gametocytes of *Eimeria maxima,* or the full complement of the nucleic acid.

2. An isolated vector comprising an isolated nucleotide sequence encoding a 56 kDa polypeptide having the amino acid sequence set forth as SEQ. ID. NO. 3 present in gametocytes of *Eimeria maxima,* or the full complement of the nucleic acid.

3. An isolated host cell comprising an isolated vector comprising an isolated nucleotide sequence encoding a 56 kDa polypeptide having the amino acid sequence set forth as SEQ. ID. NO. 3 present in gametocytes of *Eimeria maxima,* or the full complement of the nucleic acid.

4. A method of producing a 56 kDa polypeptide present in gametocytes of *Eimeria maxima* comprising culturing isolated host cells comprising an isolated nucleotide sequence encoding a 56 kDa polypeptide having the amino acid sequence set forth as SEQ. ID. NO. 3 and isolating the 56 kDa polypeptide from the cells so cultured.

5. A vaccine for immunizing a subject against infection by *Eimeria maxima* comprising an isolated nucleic sequence encoding a 56 kDa polypeptide having the amino acid sequence set forth as SEQ. ID. NO. 3 present in gametocytes of *Eimeria maxima* or the full complement of the nucleic acid.

6. A method of immunizing a subject against infection by *Eimeria maxima* comprising administering to the subject the vaccine of claim 5.

7. The isolated nucleic acid of claim 1, wherein the nucleotide sequence is set forth as SEQ ID NO: 1.

8. The isolated nucleic acid of claim 1, wherein the isolated nucleic acid is a plasmid designated 56TRCHisbl plasmid deposited under Australian Government Analytical Laboratories Accession No. NM01/122400.

9. The nucleic acid of claim 1, wherein the nucleic acid is a DNA molecule or an RNA molecule.

10. The nucleic acid of claim 9, which is a cDNA molecule.

11. The nucleic acid of claim 1, further comprising an operatively linked promoter.

12. The vector of claim 2, wherein the vector is a plasmid.

13. The host cell of claim 3, wherein the cell is a bacterial cell, a plant cell, an insect cell, or a mammalian cell.

14. An isolated transformed cell comprising an isolated nucleotide sequence encoding a 56 kDa polypeptide having the amino acid sequence set forth as SEQ. ID. NO. 3 present in gametocytes of *Eimeria maxima* or the full complement of the nucleic acid.

15. The transformed cell of claim 14, wherein the cell is designated clone 56TRCHisbl bacteria deposited under Australian Government Analytical Laboratories Accession No.NM01/22401.

16. The vaccine of claim 5, wherein the subject is an avian species.

17. The vaccine of claim 16, wherein avian species is chickens, ducks, turkeys, geese, bantams, quail, or pigeons.

18. The vaccine of claim 5, wherein the vaccine is designed to be administered by intravenous, intramuscular or intraperitoneal injection; or by spraying said vaccine into the nostrils of the subject.

19. The vaccine of claim 17, wherein the vaccine is designed to be administered in ovo.

20. The vaccine of claim 17, wherein the vaccine is designed to be administered to an air sac of an egg.

* * * * *

SEQUENCE LISTING

<160> NUMBER OF SEQ ID NOS: 42

<210> SEQ ID NO 1
<211> LENGTH: 1754
<212> TYPE: DNA
<213> ORGANISM: Chicken

<400> SEQUENCE: 1

| | | | | | |
|---|---|---|---|---|---|
| agcagaacat | agggagttca | tctgttcctt | cttttcatca | tttattcctc | gtttctcacc | 60 |
| gttttatttt | ttttgtgtaa | ccctctccgc | tgttgagtcc | caatgacccg | cctcggcctc | 120 |
| gctgctgtcg | cgctggctct | cgccgtgggc | ccttccatgg | cagtgcccag | caccactcct | 180 |
| gtggagaatc | aggttcaccc | ttacagcgag | atgagtacct | accaggaggg | gagtgccccg | 240 |
| ggggctccgg | aggacaccac | caccaccact | acgtcgtccc | ctgtttccga | tggagccgag | 300 |
| cagtggcttg | agagctttgt | tcgtgctgtg | cagcgccagc | tgcagcttca | ggaccaaatg | 360 |
| atgcgtcagc | tcatgaggga | cattcaggag | tacctgagca | ctgcgttcaa | ctgggcagag | 420 |
| aaccagtcta | ctgcctacac | ccgtgttacc | gagatgatgg | acatgatctc | caacagaatg | 480 |
| aatgcagcaa | tggacagctc | aaacgaactc | atgaccacta | gcgacaccac | agaccccgag | 540 |
| accctccgcc | gtgcaactcg | caagtacatg | aaggaggttc | gcgttcagga | cgtcctggta | 600 |
| gatgctctct | gggcctctct | ccgcggtgta | cagacagctg | cctggatgaa | tggagtgacc | 660 |
| gctattgaga | aggaggagac | gactcccatg | gctagccgcg | ctgctgagga | gttcctccac | 720 |
| cgcatgtacc | ataacctgag | ggcagcaggt | atgtctgaag | aagatgttgc | caagttcatc | 780 |
| cctagagccg | agtacaaccc | ctccgagcag | tcaagaaata | tgggcagaaa | gggcaggagc | 840 |
| ttctactacg | gcggctatcc | cagctactac | aactccccct | actacagcta | cagcagctac | 900 |
| cccagctact | acaactacag | ctacccgtca | tacagctaca | gcagctaccc | cagctactac | 960 |
| cgctacagca | gctaccccta | ctacaactac | agctatccca | gctactacaa | ctacggcagc | 1020 |
| taccccctact | acagttatag | cagctacccc | agctggtact | ggcgccgtct | ccgctctttg | 1080 |
| gcaacagcaa | cttgcccaga | ctgccctcct | ctcaccactc | ccagcatgat | cccaactccc | 1140 |
| cccccaatga | tgaacatgat | gaacacccca | cccccatgg | caaacatgat | gaccagcatg | 1200 |
| atgatgaaca | ctcccatggt | tcctcctccc | cgcacccctcg | gaactgaagc | catgagcctc | 1260 |
| ggcttggccc | ccatcggtat | caccggcgcc | cccatgacag | gtttcggtgt | tcctcctgag | 1320 |
| ttcggtccct | ttggagccga | aggtatcggc | ctccccaccg | atgccctcgg | cagcaccccc | 1380 |
| gaaatgacac | cattcgaccc | aactacccccc | tacagaactc | tcgcccccat | ggacctcccc | 1440 |
| cccatccccc | ctcctgtctt | ccctgaaacc | cctatgaggc | cacctactcc | cttcggcttc | 1500 |
| ggacctgcac | ctgttcctcc | catgcccttc | taaacgacct | accatccctc | aatccatagc | 1560 |
| tcacatttcg | tagcctcaaa | acagtttttt | gttcatttca | cttccaggac | tcatgctgcg | 1620 |
| acatttgcat | tcgtacctcg | aaaccgtcaa | cctcaaaccc | caaaccattc | tgtgacctcc | 1680 |
| cctcgcaaac | gcggaaggcg | gaacattttt | tctgaagtat | attactacgt | taaaaaaaaa | 1740 |
| aaaaaaaaaa | aaaa | | | | | 1754 |

<210> SEQ ID NO 2
<211> LENGTH: 1754
<212> TYPE: DNA
<213> ORGANISM: Chicken

```
<400> SEQUENCE: 2
tcgtcttgta tccctcaagt agacaaggaa gaaaagtagt aaataaggag caaagagtgg      60
caaaataaaa aaaacacatt gggagaggcg acaactcagg gttactgggc ggagccggag     120
cgacgacagc gcgaccgaga gcggcacccg ggaaggtacc gtcacgggtc gtggtgagga     180
cacctcttag tccaagtggg aatgtcgctc tactcatgga tggtcctccc ctcacggggc     240 cccccgaggcc tcctgtggtg gtggtggtga tgcagcaggg gacaaaggct acctcggctc     300
gtcaccgaac tctcgaaaca agcacgacac gtcgcggtcg acgtcgaagt cctggtttac     360
tacgcagtcg agtactccct gtaagtcctc atggactcgt gacgcaagtt gacccgtctc     420
ttggtcagat gacggatgtg ggcacaatgg ctctactacc tgtactagag gttgtcttac     480
ttacgtcgtt acctgtcgag tttgcttgag tactggtgat cgctgtggtg tctgggctc     540 tgggaggcgg cacgttgagc gttcatgtac ttcctccaag cgcaagtcct gcaggaccat     600
ctacgagaga cccggagaga ggcgccacat gtctgtcgac ggacctactt acctcactgg     660
cgataactct tcctcctctg ctgagggtac cgatcggcgc gacgactcct caaggaggtg     720
gcgtacatgg tattggactc ccgtcgtcca tacagacttc ttctacaacg gttcaagtag     780
ggatctcggc tcatgttggg gaggctcgtc agttctttat acccgtcttt cccgtcctcg     840
aagatgatgc cgccgatagg gtcgatgatg ttgaggggga tgatgtcgat gtcgtcgatg     900
gggtcgatga tgttgatgtc gatgggcagt atgtcgatgt cgtcgatggg gtcgatgatg     960
gcgatgtcgt cgatggggat gatgttgatg tcgataggat cgatgatgtt gatgccgtcg    1020
atggggatga tgtcaatatc gtcgatgggg tcgaccatga ccgcggcaga ggcgagaaac    1080
cgttgtcgtt gaacgggtct gacgggagga gagtggtgag ggtcgtacta gggttgaggg    1140
gggggttact acttgtacta cttgtggggt ggggggtacc gtttgtacta ctggtcgtac    1200
tactacttgt gagggtacca aggaggaggg gcgtgggagc cttgacttcg gtactcggag    1260
ccgaaccggg ggtagccata gtggccgcgg gggtactgtc caaagccaca aggaggactc    1320
aagccaggga aacctcggct tccatagccg gaggggtggc tacggagcc gtcgtggggg    1380 ctttactgtg gtaagctggg ttgatggggg atgtcttgag agcgggggta cctggagggg    1440 gggtagggg gaggacagaa gggactttgg ggatactccg gtggatgagg gaagccgaag    1500
cctggacgtg gacaaggagg gtacgggaag atttgctgga tggtagggag ttaggtatcg    1560
agtgtaaagc atcggagttt tgtcaaaaaa caagtaaagt gaaggtcctg agtacgacgc    1620
tgtaaacgta agcatggagc tttggcagtt ggagtttggg gtttggtaag acactggagg    1680
ggagcgtttg cgccttccgc cttgtaaaaa agacttcata taatgatgca atttttttt    1740 tttttttttt tttt                                                   1754

<210> SEQ ID NO 3
<211> LENGTH: 476
<212> TYPE: PRT
<213> ORGANISM: Chicken

<400> SEQUENCE: 3

Met Thr Arg Leu Gly Leu Ala Ala Val Ala Leu Ala Leu Ala Val Gly
 1               5                  10                  15

Pro Ser Met Ala Val Pro Ser Thr Thr Pro Val Glu Asn Gln Val His
            20                  25                  30

Pro Tyr Ser Glu Met Ser Thr Tyr Gln Glu Gly Ser Ala Pro Gly Ala
        35                  40                  45
```

```
Pro Glu Asp Thr Thr Thr Thr Thr Ser Ser Pro Val Ser Asp Gly
         50                  55                  60

Ala Glu Gln Trp Leu Glu Ser Phe Val Arg Ala Val Gln Arg Gln Leu
 65                  70                  75                  80

Gln Leu Gln Asp Gln Met Met Arg Gln Leu Met Arg Asp Ile Gln Glu
                 85                  90                  95

Tyr Leu Ser Thr Ala Phe Asn Trp Ala Glu Asn Gln Ser Thr Ala Tyr
            100                 105                 110

Thr Arg Val Thr Glu Met Met Asp Met Ile Ser Asn Arg Met Asn Ala
        115                 120                 125

Ala Met Asp Ser Ser Asn Glu Leu Met Thr Thr Ser Asp Thr Thr Asp
130                 135                 140

Pro Glu Thr Leu Arg Arg Ala Thr Arg Lys Tyr Met Lys Glu Val Arg
145                 150                 155                 160

Val Gln Asp Val Leu Val Asp Ala Leu Trp Ala Ser Leu Arg Gly Val
                165                 170                 175

Gln Thr Ala Ala Trp Met Asn Gly Val Thr Ala Ile Glu Lys Glu Glu
            180                 185                 190

Thr Thr Pro Met Ala Ser Arg Ala Ala Glu Glu Phe Leu His Arg Met
        195                 200                 205

Tyr His Asn Leu Arg Ala Ala Gly Met Ser Glu Glu Asp Val Ala Lys
    210                 215                 220

Phe Ile Pro Arg Ala Glu Tyr Asn Pro Ser Glu Gln Ser Arg Asn Met
225                 230                 235                 240

Gly Arg Lys Gly Arg Ser Phe Tyr Tyr Gly Gly Tyr Pro Ser Tyr Tyr
                245                 250                 255

Asn Ser Pro Tyr Tyr Ser Tyr Ser Ser Tyr Pro Ser Tyr Tyr Asn Tyr
            260                 265                 270

Ser Tyr Pro Ser Tyr Ser Tyr Ser Ser Tyr Pro Ser Tyr Tyr Arg Tyr
        275                 280                 285

Ser Ser Tyr Pro Tyr Tyr Asn Tyr Ser Tyr Pro Ser Tyr Tyr Asn Tyr
    290                 295                 300

Gly Ser Tyr Pro Tyr Tyr Ser Tyr Ser Ser Tyr Pro Ser Trp Tyr Trp
305                 310                 315                 320

Arg Arg Leu Arg Ser Leu Ala Thr Ala Thr Cys Pro Asp Cys Pro Pro
                325                 330                 335

Leu Thr Thr Pro Ser Met Ile Pro Thr Pro Pro Met Met Asn Met
            340                 345                 350

Met Asn Thr Pro Pro Met Ala Asn Met Met Thr Ser Met Met Met
        355                 360                 365

Asn Thr Pro Met Val Pro Pro Arg Thr Leu Gly Thr Glu Ala Met
    370                 375                 380

Ser Leu Gly Leu Ala Pro Ile Gly Ile Thr Gly Ala Pro Met Thr Gly
385                 390                 395                 400

Phe Gly Val Pro Pro Glu Phe Gly Pro Phe Gly Ala Glu Gly Ile Gly
                405                 410                 415

Leu Pro Thr Asp Ala Leu Gly Ser Thr Pro Glu Met Thr Pro Phe Asp
            420                 425                 430

Pro Thr Pro Tyr Arg Thr Leu Ala Pro Met Asp Leu Pro Pro Ile
        435                 440                 445
```

```
Pro Pro Pro Val Phe Pro Glu Thr Pro Met Arg Pro Pro Thr Pro Phe
    450                 455                 460
Gly Phe Gly Pro Ala Pro Val Pro Pro Met Pro Phe
465                 470                 475

<210> SEQ ID NO 4
<211> LENGTH: 2145
<212> TYPE: DNA
<213> ORGANISM: Chicken

<400> SEQUENCE: 4
atacaaatcc ttttatctg gttccaacac gctcactcaa ccaccacctg gacacaccct      60
ccccatacat acaggagcag cagcaacacc agcatcaaga tgacgcgtgc ggcagcgctt     120
gccggggttt tggccctggc tgcagcaggc agcagccttg ctctacctac tgtattggac     180
acaacgactg gcacccaagt ggagtggact gagacccctt agacacaac agaggtaact      240 atggggggaga tgggcagcac caccagcggc acgactccaa ccagcactgg tgtgcgaatg    300
atggaggctg aaactacaac cccatcaacc cctgaggctc cccagcagca gcagcagatg     360
cctcagcctc aacctcagcc acagcaaaca actcccgttc ctgaggccgt attagaggca     420
attatgcaag aaatgcaaaa tattttccgt tcttctcttg taccaggttg ggatactgtc     480
ggtacagcag cagatgctgt acgtcagatt gtaacccgtg taagagaacg tcttacagga     540
ccattaatga tgacagagat ggatactggt cttggtagaa caggaccttt atcaaccaca     600
ggtgcaacag gagcaacaac aggtcctgtt gctgcattac gcggtgtaac aaatgatttc     660
cttagggaaa taatgattca agaagcagta cttgagacat tatgggcagt tgtacgtgat     720
gcacaagaaa gaccatggct agttaatgaa caggaagtat tgcatgcagt aacagcagat     780
gctgtacaag gtttccttgg tcgcatgcat gatcgtcttc gtgcaacagg tttctctgag     840
gaagaagtca tgagacttct acctaggtca cgtaatggtg ttgtacccg tacagggggc      900 ctctttgatc aatgtaacga tgcccctccc tctcgtcttc ttggtaagag gatgtatagt     960
actggatatt atggttatgg atatccttct tattatagct atggatatag ttatccagct    1020
tattcacatt atcctgtttc ttatccttac tatgggtata gctggggccc ctcatactac    1080
tatggcagcg gatactatgg taaacatgga tataagtacg gacattatta caggagactt    1140
gctgagcagg aaccaagacc tgttatgcct cctgcagcag caactgccgc agcaaaccta    1200
agagcagcag cagcagcagc agcagaagta ccaccaccac caccaccagc agcagtacca    1260
ccaccaccac cagcagcagc agcaggtacc ccagctatga tgcctcctcc tatgatgggt    1320
gttgaagaac ctgttccttt ccgctccctc tatcctagct atagctggag ttatccagca    1380
tatactcgcg tgtctccctc ttattcttat tatacaccct cttatagttc ttcttactat    1440
tatccccgtt ataattatgc ctataactat cccttatatt cagactatag ctggtatgat    1500
tatagctacc cccttgccta cagcagctat agtagctacc ccctttccta tagtagctat    1560 agctacccccc ttagctatac ctaccctagt gcctttttata aagactaga ggtccctgat    1620 ctaacaacaa ctactactac tcatcatgag cagcagcagc agcagcagca agaaagtaca    1680
actactgctg tacctacaga aaccattact actccctcta ctcgtaatac acacagcagc    1740
agcctaagaa gagtaggaga aagatatgag cctattaccc ctacacaaag aactttttat    1800
aataatacag aaggtactaa caaccctgtc tatacacccg aaaatcttac agaagatgaa    1860
ccacaaactg tatgggaaac atacaactaa accctaaacc ctaaacccta aaccctcaac    1920
cctaacattt ctcattttttt tatagagaaa ttttagggaa cactaacctg cctgccttgc    1980
```

```
catcgtttat atatatccat ttgtttatta ataaacaatt tttatttacc tctagtcgtc      2040
tttttattaa cagcgcttat tcgcgttgtt tatacaaact actactattt ttacccaata      2100
atacttgtac aggcattttt taaaaaaaaa aaaaaaaaa aaaaa                       2145

<210> SEQ ID NO 5
<211> LENGTH: 2145
<212> TYPE: DNA
<213> ORGANISM: Chicken

<400> SEQUENCE: 5
tatgtttagg aaaaatagac caaggttgtg cgagtgagtt ggtggtggac ctgtgtggga        60
ggggtatgta tgtcctcgtc gtcgttgtgg tcgtagttct actgcgcacg ccgtcgcgaa       120 cggcccaaa accgggaccg acgtcgtccg tcgtcggaac gagatggatg acataacctg       180
tgttgctgac cgtgggttca cctcacctga ctctggggga atctgtgttg tctccattga      240 tacccctct acccgtcgtg gtggtcgccg tgctgaggtt ggtcgtgacc acacgcttac       300
tacctccgac tttgatgttg gggtagttgg ggactccgag gggtcgtcgt cgtcgtctac      360
ggagtcggag ttggagtcgg tgtcgtttgt tgagggcaag gactccggca taatctccgt      420
taatacgttc tttacgtttt ataaaaggca agaagagaac atggtccaac cctatgacag      480
ccatgtcgtc gtctacgaca tgcagtctaa cattgggcac attctcttgc agaatgtcct      540
ggtaattact actgtctcta cctatgacca gaaccatctt gtcctggaaa tagttggtgt      600
ccacgttgtc ctcgttgttg tccaggacaa cgacgtaatg cgccacattg tttactaaag      660
gaatcccttt attactaagt tcttcgtcat gaactctgta atacccgtca acatgcacta      720
cgtgttcttt ctggtaccga tcaattactt gtccttcata acgtacgtca ttgtcgtcta      780
cgacatgttc caaaggaacc agcgtacgta ctagcagaag cacgttgtcc aaagagactc      840
cttcttcagt actctgaaga tggatccagt gcattaccac caacatgggc atgtcccccg      900
gagaaactag ttacattgct acggggaggg agagcagaag aaccattctc ctacatatca      960
tgacctataa taccaatacc tataggaaga ataatatcga tacctatatc aataggtcga     1020
ataagtgtaa taggacaaag aataggaatg atacccatat cgaccccggg gagtatgatg     1080
ataccgtcgc ctatgatacc atttgtacct atattcatgc ctgtaataat gtcctctgaa     1140
cgactcgtcc ttggttctgg acaatacgga ggacgtcgtc gttgacggcg tcgtttggat     1200
tctcgtcgtc gtcgtcgtcg tcgtcttcat ggtggtggtg gtggtggtcg tcgtcatggt     1260
ggtggtggtg gtcgtcgtcg tcgtccatgg ggtcgatact acgaggaggg atactaccca     1320
caacttcttg gacaaggaaa ggcgagggag ataggatcga tatcgaccte aataggtcgt     1380 atatgagcgc acagagggag aataagaata atatgtggga gaatatcaag aagaatgata     1440 atagggggcaa tattaatacg gatattgata gggaatataa gtctgatatc gaccatacta     1500
atatcgatgg gggaacggat gtcgtcgata tcatcgatgg gggaaggat atcatcgata     1560 tcgatggggg aatcgatatg gatgggatca cggaaaatat cttctgatct ccagggacta     1620
gattgttgtt gatgatgatg agtagtactc gtcgtcgtcg tcgtcgtcgt tctttcatgt     1680
tgatgacgac atggatgtct ttggtaatga tgagggagat gagcattatg tgtgtcgtcg     1740
tcggattctt ctcatcctct ttctatactc ggataatggg gatgtgtttc ttgaaaaata     1800
ttattatgtc ttccatgatt gttgggacag atatgtgggc ttttagaatg tcttctactt     1860
ggtgtttgac atacccttg tatgttgatt tgggatttgg gatttgggat ttgggagttg     1920
ggattgtaaa gagtaaaaaa atatctcttt aaaatcccett gtgattggac ggacggaacg     1980
```

```
gtagcaaata tatataggta aacaaataat tatttgttaa aaataaatgg agatcagcag    2040
aaaaataatt gtcgcgaata agcgcaacaa atatgtttga tgatgataaa aatgggttat    2100
tatgaacatg tccgtaaaaa atttttttt ttttttttt ttttt                      2145
```

<210> SEQ ID NO 6
<211> LENGTH: 596
<212> TYPE: PRT
<213> ORGANISM: Chicken

<400> SEQUENCE: 6

```
Met Thr Arg Ala Ala Leu Ala Gly Val Leu Ala Leu Ala Ala
1               5                   10                  15

Gly Ser Ser Leu Ala Leu Pro Thr Val Leu Asp Thr Thr Gly Thr
            20                  25                  30

Gln Val Glu Trp Thr Glu Thr Pro Leu Asp Thr Thr Glu Val Thr Met
        35                  40                  45

Gly Glu Met Gly Ser Thr Ser Gly Thr Thr Pro Thr Ser Thr Gly
    50                  55                  60

Val Arg Met Met Glu Ala Glu Thr Thr Thr Pro Ser Thr Pro Glu Ala
65                  70                  75                  80

Pro Gln Gln Gln Gln Met Pro Gln Pro Gln Pro Gln Gln
                85                  90                  95

Thr Thr Pro Val Pro Glu Ala Val Leu Glu Ala Ile Met Gln Glu Met
                100                 105                 110

Gln Asn Ile Phe Arg Ser Ser Leu Val Pro Gly Trp Asp Thr Val Gly
            115                 120                 125

Thr Ala Ala Asp Ala Val Arg Gln Ile Val Thr Arg Val Arg Glu Arg
130                 135                 140

Leu Thr Gly Pro Leu Met Met Thr Glu Met Asp Thr Gly Leu Gly Arg
145                 150                 155                 160

Thr Gly Pro Leu Ser Thr Thr Gly Ala Thr Gly Ala Thr Thr Gly Pro
                165                 170                 175

Val Ala Ala Leu Arg Gly Val Thr Asn Asp Phe Leu Arg Glu Ile Met
            180                 185                 190

Ile Gln Glu Ala Val Leu Glu Thr Leu Trp Ala Val Arg Asp Ala
        195                 200                 205

Gln Glu Arg Pro Trp Leu Val Asn Glu Gln Glu Val Leu His Ala Val
    210                 215                 220

Thr Ala Asp Ala Val Gln Gly Phe Leu Gly Arg Met His Asp Arg Leu
225                 230                 235                 240

Arg Ala Thr Gly Phe Ser Glu Glu Val Met Arg Leu Leu Pro Arg
                245                 250                 255

Ser Arg Asn Gly Gly Cys Thr Arg Thr Gly Gly Leu Phe Asp Gln Cys
            260                 265                 270

Asn Asp Ala Pro Pro Ser Arg Leu Leu Gly Lys Arg Met Tyr Ser Thr
        275                 280                 285

Gly Tyr Tyr Gly Tyr Gly Tyr Pro Ser Tyr Tyr Ser Tyr Gly Tyr Ser
    290                 295                 300

Tyr Pro Ala Tyr Ser His Tyr Pro Val Ser Tyr Pro Tyr Gly Tyr
305                 310                 315                 320

Ser Trp Gly Pro Ser Tyr Tyr Gly Ser Gly Tyr Tyr Gly Lys His
                325                 330                 335

Gly Tyr Lys Tyr Gly His Tyr Tyr Arg Arg Leu Ala Glu Gln Glu Pro
            340                 345                 350
```

```
Arg Pro Val Met Pro Pro Ala Ala Ala Thr Ala Ala Ala Asn Leu Arg
        355                 360                 365

Ala Ala Ala Ala Ala Ala Glu Val Pro Pro Pro Pro Pro Pro Pro Ala
    370                 375                 380

Ala Val Pro Pro Pro Pro Ala Ala Ala Gly Thr Pro Ala Met
385                 390                 395                 400

Met Pro Pro Pro Met Met Gly Val Glu Pro Val Pro Phe Arg Ser
                405                 410                 415

Leu Tyr Pro Ser Tyr Ser Trp Ser Tyr Pro Ala Tyr Thr Arg Val Ser
            420                 425                 430

Pro Ser Tyr Ser Tyr Tyr Thr Pro Ser Tyr Ser Ser Tyr Tyr
        435                 440                 445

Pro Arg Tyr Asn Tyr Ala Tyr Asn Tyr Pro Leu Tyr Ser Asp Tyr Ser
        450                 455                 460

Trp Tyr Asp Tyr Ser Tyr Pro Leu Ala Tyr Ser Ser Tyr Ser Ser Tyr
465                 470                 475                 480

Pro Leu Ser Tyr Ser Ser Tyr Ser Tyr Pro Leu Ser Tyr Thr Tyr Pro
            485                 490                 495

Ser Ala Phe Tyr Arg Arg Leu Glu Val Pro Asp Leu Thr Thr Thr Thr
            500                 505                 510

Thr Thr His His Glu Gln Gln Gln Gln Gln Gln Glu Ser Thr Thr
        515                 520                 525

Thr Ala Val Pro Thr Glu Thr Ile Thr Thr Pro Ser Thr Arg Asn Thr
        530                 535                 540

His Ser Ser Ser Leu Arg Arg Val Gly Glu Arg Tyr Glu Pro Ile Thr
545                 550                 555                 560

Pro Thr Gln Arg Thr Phe Tyr Asn Asn Thr Glu Gly Thr Asn Asn Pro
                565                 570                 575

Val Tyr Thr Pro Glu Asn Leu Thr Glu Asp Glu Pro Gln Thr Val Trp
            580                 585                 590

Glu Thr Tyr Asn
        595

<210> SEQ ID NO 7
<211> LENGTH: 16
<212> TYPE: PRT
<213> ORGANISM: Chicken

<400> SEQUENCE: 7

Val Pro Ser Thr Thr Pro Val Glu Asn Gln Val His Pro Tyr Glu Met
1               5                   10                  15

<210> SEQ ID NO 8
<211> LENGTH: 14
<212> TYPE: PRT
<213> ORGANISM: Chicken

<400> SEQUENCE: 8

Pro Thr Val Leu Asp Thr Thr Thr Gly Gln Val Glu Asp Thr
1               5                   10

<210> SEQ ID NO 9
<211> LENGTH: 14
<212> TYPE: PRT
<213> ORGANISM: Chicken
<220> FEATURE:
<221> NAME/KEY: MISC_FEATURE
<222> LOCATION: (5)..(5)
<223> OTHER INFORMATION: Where X= L/I
```

```
<220> FEATURE:
<221> NAME/KEY: MISC_FEATURE
<222> LOCATION: (9)..(9)
<223> OTHER INFORMATION: Where X= L/I
<220> FEATURE:
<221> NAME/KEY: MISC_FEATURE
<222> LOCATION: (13)..(13)
<223> OTHER INFORMATION: Where X= L/I

<400> SEQUENCE: 9

Val Gln Asp Val Xaa Val Asp Ala Xaa Trp Ala Ser Xaa Arg
1               5                   10

<210> SEQ ID NO 10
<211> LENGTH: 11
<212> TYPE: PRT
<213> ORGANISM: Chicken

<400> SEQUENCE: 10

Ala Thr Gly Phe Ser Glu Glu Glu Val Met Arg
1               5                   10

<210> SEQ ID NO 11
<211> LENGTH: 11
<212> TYPE: PRT
<213> ORGANISM: Chicken
<220> FEATURE:
<221> NAME/KEY: MISC_FEATURE
<222> LOCATION: (8)..(8)
<223> OTHER INFORMATION: Where X= L/I

<400> SEQUENCE: 11

Val Thr Glu Met Met Asp Met Xaa Ser Asn Arg
1               5                   10

<210> SEQ ID NO 12
<211> LENGTH: 16
<212> TYPE: PRT
<213> ORGANISM: Chicken

<400> SEQUENCE: 12

Thr Gly Gly Leu Phe Asp Gln Ala Cys Asn Asp Ala Pro Pro Ser Arg
1               5                   10                  15

<210> SEQ ID NO 13
<211> LENGTH: 10
<212> TYPE: PRT
<213> ORGANISM: Chicken
<220> FEATURE:
<221> NAME/KEY: MISC_FEATURE
<222> LOCATION: (2)..(2)
<223> OTHER INFORMATION: Where X= L/I
<220> FEATURE:
<221> NAME/KEY: MISC_FEATURE
<222> LOCATION: (4)..(4)
<223> OTHER INFORMATION: Where X= L/I

<400> SEQUENCE: 13

Gln Xaa Gln Xaa Gln Asp Gln Met Met Arg
1               5                   10

<210> SEQ ID NO 14
<211> LENGTH: 21
<212> TYPE: PRT
<213> ORGANISM: Chicken
<220> FEATURE:
<221> NAME/KEY: MISC_FEATURE
<222> LOCATION: (4)..(4)
<223> OTHER INFORMATION: Where X= L/I
```

```
<220> FEATURE:
<221> NAME/KEY: MISC_FEATURE
<222> LOCATION: (20)..(20)
<223> OTHER INFORMATION: Where X= L/I

<400> SEQUENCE: 14

Thr Gly Pro Xaa Ser Thr Thr Gly Ala Thr Gly Ala Thr Thr Gly Pro
1               5                   10                  15

Val Ala Ala Xaa Arg
            20

<210> SEQ ID NO 15
<211> LENGTH: 8
<212> TYPE: PRT
<213> ORGANISM: Chicken
<220> FEATURE:
<221> NAME/KEY: MISC_FEATURE
<222> LOCATION: (6)..(6)
<223> OTHER INFORMATION: Where X= L/I

<400> SEQUENCE: 15

Ala Ala Glu Glu Phe Xaa His Arg
1               5

<210> SEQ ID NO 16
<211> LENGTH: 6
<212> TYPE: PRT
<213> ORGANISM: Chicken
<220> FEATURE:
<221> NAME/KEY: MISC_FEATURE
<222> LOCATION: (2)..(2)
<223> OTHER INFORMATION: Where X= L/I

<400> SEQUENCE: 16

Pro Xaa Thr His Val Glu
1               5

<210> SEQ ID NO 17
<211> LENGTH: 12
<212> TYPE: PRT
<213> ORGANISM: Chicken
<220> FEATURE:
<221> NAME/KEY: MISC_FEATURE
<222> LOCATION: (2)..(2)
<223> OTHER INFORMATION: Where X= L/I

<400> SEQUENCE: 17

Arg Xaa Ala Ala Val Pro Gly Thr Thr Ala Gly Thr
1               5                   10

<210> SEQ ID NO 18
<211> LENGTH: 22
<212> TYPE: PRT
<213> ORGANISM: Chicken
<220> FEATURE:
<221> NAME/KEY: MISC_FEATURE
<222> LOCATION: (2)..(2)
<223> OTHER INFORMATION: Where X= L/I
<220> FEATURE:
<221> NAME/KEY: MISC_FEATURE
<222> LOCATION: (6)..(6)
<223> OTHER INFORMATION: Where X= L/I

<400> SEQUENCE: 18

Asp Xaa Gln Glu Tyr Xaa Ser Thr Ala Phe Asn Trp Ala Glu Asn Gln
1               5                   10                  15

Ser Thr Ala Tyr Thr Arg
            20
```

```
<210> SEQ ID NO 19
<211> LENGTH: 23
<212> TYPE: PRT
<213> ORGANISM: Chicken
<220> FEATURE:
<221> NAME/KEY: MISC_FEATURE
<222> LOCATION: (1)..(1)
<223> OTHER INFORMATION: Where X= L/I

<400> SEQUENCE: 19

Xaa Ala Glu Gly Ala Glu Pro Arg Pro Val Met Pro Pro Ala Ala Ala
1               5                   10                  15

Thr Ala Ala Ala Asn Leu Arg
            20

<210> SEQ ID NO 20
<211> LENGTH: 18
<212> TYPE: PRT
<213> ORGANISM: Chicken
<220> FEATURE:
<221> NAME/KEY: MISC_FEATURE
<222> LOCATION: (12)..(12)
<223> OTHER INFORMATION: Where X= L/I

<400> SEQUENCE: 20

Arg Gln Thr Ala Ala Trp Met Asp Arg Thr Ala Xaa Glu Gln Glu Glu
1               5                   10                  15

Thr Thr

<210> SEQ ID NO 21
<211> LENGTH: 14
<212> TYPE: PRT
<213> ORGANISM: Chicken
<220> FEATURE:
<221> NAME/KEY: MISC_FEATURE
<222> LOCATION: (11)..(11)
<223> OTHER INFORMATION: Where X= L/I

<400> SEQUENCE: 21

Met Asn Ala Ala Met Asp Ser Ser Asn Glu Xaa Met Thr Thr
1               5                   10

<210> SEQ ID NO 22
<211> LENGTH: 7
<212> TYPE: PRT
<213> ORGANISM: Chicken
<220> FEATURE:
<221> NAME/KEY: MISC_FEATURE
<222> LOCATION: (6)..(6)
<223> OTHER INFORMATION: Where X= L/I

<400> SEQUENCE: 22

Lys Phe Pro Glu Thr Xaa Phe
1               5

<210> SEQ ID NO 23
<211> LENGTH: 18
<212> TYPE: PRT
<213> ORGANISM: Chicken
<220> FEATURE:
<221> NAME/KEY: MISC_FEATURE
<222> LOCATION: (12)..(12)
<223> OTHER INFORMATION: Where X= L/I
```

```
<400> SEQUENCE: 23

Arg Gln Thr Ala Ala Trp Met Asp Arg Thr Ala Xaa Glu Gln Glu Glu
1               5                  10                  15

Thr Thr

<210> SEQ ID NO 24
<211> LENGTH: 21
<212> TYPE: PRT
<213> ORGANISM: Chicken

<400> SEQUENCE: 24

Arg Gly Val Gln Thr Ala Ala Trp Met Asp Gly Val Thr Ala Ile Glu
1               5                  10                  15

Lys Glu Glu Thr Thr
            20

<210> SEQ ID NO 25
<211> LENGTH: 21
<212> TYPE: PRT
<213> ORGANISM: Chicken

<400> SEQUENCE: 25

Arg Gly Val Gln Thr Ala Ala Trp Met Asn Gly Val Thr Ala Ile Glu
1               5                  10                  15

Lys Glu Glu Thr Thr
            20

<210> SEQ ID NO 26
<211> LENGTH: 7077
<212> TYPE: DNA
<213> ORGANISM: Chicken

<400> SEQUENCE: 26
atgctgcatc gcaacccgcg gtgggcgctt tgtgcagccc tcgctgcact ctatggcgga     60
acaggaatcg ccagcgccga agttaacaat gaattgagca gtgcgaatc tgggtggaca    120 ccctggacta cctgcaaccc gcaaactggt ctgcgggaga ggcacaatgc acagtgcgag    180
acatgggtgg aggttgagga atgccagaag ctgacaggat gtggcaactg gactccttgg    240
tctcccggcg atatgtcgtg tgtggtggga cagtttcaaa cccgcaacag ggagggctgc    300
ccagaggtgc aggaagtgag ggcatgcagg cctgtacttc tagaatgcaa cgatcaatgg    360
accccctgga caatgtgcga caccaaccgc gtccaggaaa gatacaactc aaagtgcgga    420
cccgtcgaag tccgcgagtg caacatggac gacgcagaga tcgagaaatg cggcgagttc    480
gtggaatggg atccccctat gaatggagac tgcgtacgcg ggggtaccca cacgcgttac    540
cgtcaaaact gcccagaccg caaagaggtg cgggtgtgcg gagcctttga ttgcagtagc    600
tgctctgtaa acgccacttg cgatcccatt ggtgcatcct gcgaatgcaa gcctggtttc    660
cgcggcaatg ggaagacctg cgaggccttc aaccctgcg aagatacccc tgcaccttgc    720
gacagcaacg ccatctgcac cccagacgca atgacgccaa atgccagtgc aaggcaggct    780
gggacgcaga ttccggagca ggcagcagca agaagcttg cgttgaggtc gacgagtgcg    840
catccaacac ccaccagtgc ccggcacact ccacatgcat caacaccaag ggctcttata    900
agtgcgactg caaccaggga taccgtcaag ggagaggacg gacagtgtca tgacgtcgat    960
gaatgcacca acgagagca cacctgcccc gctcactcca cttgtttgaa tacagctggc   1020
agctacgagt gccgctgcga cactgggtac agcggaaatg caactgcaga cagcccttgc   1080
```

```
aagaacattg acgaatgcgc caaccccaac gcctgctcgg ccaacgctat ctgcacagac    1140
accgacggct ccttcacctg cagctgcccc gaagggtaca gcggccaggg aacccatgac    1200
tctccctgct ccaagatcga cttctgcgca taccccctcac tcaatacatg cggagcccac   1260
tccacttgca acaccctcac atctttcaag tgcatctgcg atgcgggata tgaaggcgcc    1320
ggcactcgcg agagcccgtg cgtggacgtg aacgagtgct cgaacgagaa gcccacaaac    1380
aactgcaaca gaaacgcaaa ctgcaccaac accgagggat cctacacttg cgaatgcaag    1440
cccggtttct ctggcgacgg catgggtccc aacgggtgta ccgacatcga cgagtgcgcg    1500
gcggagcagt ccccctgcga ccctcacgcc tcctgcagca acactgaggg ctcgtatgta    1560
tgcacctgca acaccggcta cgagccagct tcaaccgacg ggcatgcatg caaagatatc    1620
gacgagtgcg ccaccggtgc agctgggtgc cacgtgtcag cacagtgtct gaacacggac    1680
ggcagctacg agtgcaagtg tcttgagggc ttcgtcggcg acggaaagac ctgcaacgac    1740
gtcgatgagt gcgctgcggc gacatctcct tgcggtgaca cactcactg ccagaacaca     1800 attggcagct acgagtgcga gtgcaaggct ggctatggca acatgcaaga caacgcatgc    1860
agcgacattg acgagtgcaa ggatgcgaac accaagatcc ctgacaactg tctttgcgtg    1920
aacaatgatg gcagctactc ccttgaggcg aaggctggat acgaattggt gaacggcgag    1980
tgcatcaaga tcgacttctg cgcccgcggc gcatgcaact cgctggcctc ctgcaaggag    2040
aatgaagaag gcacagcggc gatctgcacc tgcctgccag gctacagcgg cgacggcact    2100
gctgaaggcc actgcaacga cattgacgag tgtgcaggtc agaatgactg tgctcctgcc    2160
gagcagggag gcatctgcga gaacactgtc ggctcgtaca cctgcaagtg caaagagggg    2220
tacaggcaag atggaaactc atgcactgag atcgacgagt gcgctgaggg aacccacaac    2280 tgccacccctt ccgccacctg cagcaacacc cccggaagct tcacctgcca atgcaacagt   2340
ggattcactg gcagcggtgt ggagtgcgaa gacattgacg agtgctcaac tgaggcagat    2400
gattgtggtg caaacaccat ctgcagcaac accattggtg ctttcgagtg caactgccgt    2460
gaaggctatg aacgcgcaga cgcaaagacg tgcgtcgaca tcgacgaatg cgcgacaggc    2520
acacacactt gctcgaacca cgccacctgc accaataccg atgggtcatt cacatgccag    2580
tgcaaccccg gcttcgaagg tgacggccac aagtgcgagg acatcgactt ctgcggtgct    2640
ggacagcacg actgcaatgt gcatgccgag tgctctgaga gcgaggacaa caccactttc    2700
aagtgcacct gtataacagg gtacgctgga gacggccatg gcgaggcagg ctgccaagac    2760
attgatgagt gcgcagaaga aaacatctgc ggaagcaacg ctgtctgcac aaacaccgca    2820
ggaagctacc aatgcgcatg ccgtgagggc ttcgttgcat cagctgaaca gcagcagcag    2880 ggaacccag cactggtttg cgtggacgtc gacgagtgca gcgacgcttc gaagaacaca     2940
tgtgccaagc cagccgacgg aggcatttgc acaaacactg aaggcagcta cgaatgcgct    3000
tgcaagccag gctaccaagg tgacggccac agctgcgcag acatcaacga atgcactgca    3060
cagggcacct gcggcgaaca cacaacttgc aagaacacac ccggatcctt ccagtgcgac    3120
tgcgttgagg gattcgagcg cgctgatgaa cgcacctgcc gtgacatcaa cgagtgcgag    3180
acaggagcag tcgtgctgcc accgaactcc acctgcgtca acactgaagg cagctacgac    3240
ttcgactgcg ttgctgggta ccgccgcact gatggagctt gtgtgaagat cgacttctgc    3300
aaggagaagg gatgcaacgc aaacgccaca tgccgcgaaa acgatgccgg caccgaggcc    3360
atctgcactt gcaaggaagg ctatgaaggc agcgagaag gcgaagatgg ttgccagaac     3420
atcaatgagt gcgagagagg cgaaccctgc aaggacttcg gcgaaggcgg tgtttgcgtc    3480
```

```
gacacaccag gatcattcac ttgcgagtgc gctgctggat tcattcaacg ccgctccgtt    3540
tgccaagatg ttgacgaatg tctcgacgga aagctgaaca cctgcgctgc caccggaggc    3600
gtctgctcca acaccgtcgg ttccttcacc tgctcgtgcg ccagcggctt cgaaggcgat    3660
ggccacacct gcaatgatgt cgacgaatgc gcaacagcac agcacacctg tgacccgaat    3720
gccacttgcg tcaacaccga aggcagcttc gagtgccgct gcaatgccgg attcgagggc    3780
gacggacaca cctgcgcaga catcgacgaa tgcgcagacc cagccaaaaa cacatgcgat    3840
acacacaagg gtgtatgcca aaacaccaca gggtcctaca cctgcggctg caagaccgga    3900
ttcagtcttg cagctgacgg aagcacatgc gaaaacgtcg acgagtgcgc ggcgggaact    3960
gcaaactgca acgagcgaag cttctgtaag gacacagagg gttcctacca atgcgagtgc    4020
aagaacggct acaaggctgc aggagaggac tgtgtggacg ttgacgagtg cgaggctggc    4080
gtgcatggat gcagcgagca cgcaatctgc acaaatacag acggcagcta ctcctgcgaa    4140
tgcatggagg ataccaggg agacggcaag gcttgcgaga agacagtcgg cgtctgcgac    4200
tccgctccct gcggtgccca cgccacctgc gagcctgcag gggacaacta cacttgcaca    4260
tgccacccag gctacgagat gcgcgaagga gcctgcgttg acatcgatga gtgcacagca    4320
ggcagcctca actgcgaccc tcatgccatt tgcacaaaca ccgacggctc cttcacttgc    4380
gtctgtggca gcggctatac cggccttggc acatcctgcg aagacatcga cgagtgcgcg    4440
ggtaacgcag caggctgcga catccacgcc gtctgcacga acactcccgg atcgttcaag    4500
tgcgagtgca agagcggctt cgaaggcgat ggcacgcaat gcacggagaa ggtgttgctc    4560
cccggacaga ttcactgcga agcctggact gcatggacag agtgtaccga cggcgccaaa    4620
accagcacac gcagctgcct tgcactgccg cttaagaagg agatgcgcgc ctgccctgca    4680
gctgacttct cccagtgcgg agagttcact gaatggactg cctgccctgg aaccaacaat    4740
aacctgtctc ataggcgcac tgaaagattc ggagaacccg gatgcgaaga tgcagaggaa    4800
gtccgcgaat gcccagatga agagaccgag cagaaatgcg gcgcctgggg tgagtggacc    4860
gcctgcggcg acccatcccc tggcctgaga actcgcgcac gcgagaactg ccccgatgtg    4920
gtagagttcg agcgttgcac tatgcccagt gagcctgagg ctggcgaagt gactgagcct    4980
cacacagaag gaggagccgg agttggtggc gaagtgactg agcctgacac ggaagaagga    5040
gccggagttg gtggtgaagt gcagcccggt acagaagaag gagcaggagt tggtggtgaa    5100
gtgcagcccg gtacagaaga aggagccgga gttggtggtg aagtgcagcc cggtacagaa    5160
gaaggagccg gagttggtgg tgaagtgcag cccggtacaa agaaggagc cggcattggt    5220
ggcgaagtga ctgagcctga caccgaagga ggagccggag ttagtggcga accgaccgaa    5280
gaagagggca ccgaaagcac cggtccatgc aaagagttcg accctggac ggcctgcaag    5340
gaggacgaga acggagtcgg catccaacgc cgtatgtgcg ccggcagaga agacatcatc    5400
gaatccagaa tttgcactgt cacgcgatgac tgcggagaat ggaccccctg gtcaacttgc    5460
actaacggca gccaggccag aaacaaacgc ttctgcacca acgttaggga agtccgtctc    5520
tgcggagctg acattccagt tacagacgga tgcacgtgga gcgagtggac ttcttgcagt    5580
ctagtcaatg aggagggcgg ctacttccgc acgcgcacat cctctgactg caacatgaat    5640
gaagtgcagg cctgctctcc cagcagcagc acaaccgcag acagcgaaac agaaggcacc    5700
tgctctgcat ggaacccctg gacggagtgc tcgaacggcc accagacacg caagtgtgcc    5760
acaatggaag cagaagaatc gcgcacttgc ggagagactc cagagaactg cggagaattc    5820
ggccccttcg aacccgcaaa ctgcacggcc ggccaaatgg tcaccaggac gcgcacctgc    5880
```

-continued

| | |
|---|---|
| ggagaaaccg agcagaagga aaccaaactg tgcgacgtca gctccaccga agaaggaaaa | 5940 |
| caatgcggtc agtggggccc atggagcgaa tgcaacatcc acctgggctc agaggacaat | 6000 |
| gtgcgtgttc gtgaggacac cgcttgcggc gtgacggagt acgaggagtg cagcaagccg | 6060 |
| gcgaacaacg cctttgtctg cacaccttgg agtgaatgct cggacaagaa ggagcggaga | 6120 |
| acgtgcacca tccgcaaaaa cggtcttgtt cagacacgtc aagaattcag aacatgcagt | 6180 |
| gtagacatcg ccacaacttg cggcgatttc ggcgcatggt ctgaatgcaa cgctgagggc | 6240 |
| ttgcatcagc gcagtctcga gaaatgcccc gacgtcatcg aggtcgcaac ttgcggcagt | 6300 |
| gaggattgcc cgccattcgg cgagtggact gaatgcggcg ttccagagga gggcatgcgt | 6360 |
| tctcgccaac gcattgactg cgttgaatct gcagcctgcc agtgcacaga agtggagagc | 6420 |
| tgcttcgaca ccgaattgca ccccattcca gcccccggta cggaaacagg cgaaggagag | 6480 |
| ggagagaccg agacaggcga aggcgaaact ggtgaagcag gtggcgagga aggcgagcaa | 6540 |
| acaggagaag gcgaagtgca gcccccagaa gaagagcttc ctggggagag tgtaactgag | 6600 |
| cctgaggaga agcctgagga ggagctacct gaggaggagg ttactgagcc tgaggagaag | 6660 |
| cctgaggagg gtgtgactca gcctgaggag acacctgagc agcctgttga gggtaccgaa | 6720 |
| gaagagggca agcaggagtc tgaggctgcc cccgaaactc ctgccgtcca gccaaaacca | 6780 |
| gaggagggtc acgaacgccc agaacccgaa gaggaggagg agaagaagga agaaggcggc | 6840 |
| ggcttcccaa cagctgcagt ggcaggaggt gttggtggtg tgttgctcat agctgctgta | 6900 |
| ggtggtggtg ttgcagcctt cactagcggc ggaggtggcg ctggcgcaca ggaggcagaa | 6960 |
| caggtcgagt tcgaaggaga agataccgga gcagcaactg ccgagacacc tgaagccgat | 7020 |
| acagttatcg acatcacaga cgaagacgac tactgggccg acagcggcga cattcag | 7077 |

<210> SEQ ID NO 27
<211> LENGTH: 6567
<212> TYPE: DNA
<213> ORGANISM: Chicken

<400> SEQUENCE: 27

| | |
|---|---|
| atgggttttt tcgtcttcac aggcggtgat ttcggcgact ggagcccccc tctcgctggt | 60 |
| gactgcgtgc ctggcactac tcacacacgc cagagggcaa attgcccaaa ccacaaggag | 120 |
| gtgcgggttt gcggcgcctt cgattgtagc cagtgctcag tcaacgctac ctgcgacccc | 180 |
| ctcggagcca cttgtcagtg caaaccgggt tccgaggcg atgggactca gtgcgaggca | 240 |
| ttcaaccctt gcgaagggga cggctcctgt gtgatgcga acgcgacctg cacggctgat | 300 |
| ggaaatgacg ccaaatgcca ctgcaacaag ggctggaacg cagacagcaa ggcaggtgcc | 360 |
| agcggtcacg catgcgtgga ggaggacgaa tgcgccaaca cacgcacga atgtccgcag | 420 |
| cactcaactt gcgtcaacac tgagggctcc tatgaatgca actgcttacc gggttatcag | 480 |
| aaggatcagg atgggaaatg ccaggacata acgagtgcg ctggggaaca tggttgtccc | 540 |
| gcacactcga cttgcgtgaa cacggcaggc agcttcgagt gcaagtgcga cgccggtttc | 600 |
| agtggcagtg ctacttctga gagtccttgc tcgaatatag acgagtgcca agacccggat | 660 |
| gcctgctcag ccaacgcaat ctgcgcagac actgagggct ctttcacttg cagctgccct | 720 |
| gagggttaca cgcgtgggg atcacacgac tctccttgct cgaagataga ttactgcgcc | 780 |
| gacccccacac tgaacaccctg cggggcccac tcgacttgtg tgaacacact aacgacgttc | 840 |
| aagtgcgttt gcgatgccgg ttatgacggc gcgggaacgc acgagagccc ttgtgtggat | 900 |
| atcgacgagt gctccaagga gaaaccatcc aatgactgca accgaaacgc cgtttgcaca | 960 |

```
aatactgagg gatcgtacac ctgcgcatgc aaggaaggct tctctggcga gggtttcgga   1020
gctgcagggt gtgcagatgt cgatgagtgc gcgaattcgc cctgcgacgc ccacgcctct   1080
tgtgccaaca ccgagggttc ctacgtttgc acttgcaacc ctggctatga accagcctca   1140
agcgacggac atgcatgcaa ggacgttgac gagtgtgcag cgggcacggc ggaatgccac   1200
gtctccgcac agtgtgtgaa cgtggatggc agctatgaat gccactgctt ggaaggtttc   1260
attggcgacg gaaaggtgtg cagtgacgtt gacgagtgtg cggctgaggc ttcgccctgt   1320
ggcgcaaaca cgcattgcct gaacaccatc ggcagctacg agtgcgagtg caaggacgga   1380 tatgccaca tggagggcaa cgcgtgcagc gacatcgatg agtgctcaga ggcgtctaca   1440
gagatcccag agaactgcaa ctgtgtcaac accgagggga gcttctccct tgaggcaaag   1500
cctgggtacg agctcgtcga cggcaagtgc gtcaagatcg acttctgcgc ccgtggtgca   1560
tgcaactcgc tggcgcactg caaggagaat cccgagggca ccgcggcgat ctgcacttgc   1620
atagctggct attcaggtga cggcacagct cagggccact gcgatgacat cgatgagtgc   1680
ttggcggaga atgactgcac ccctgccgat caaggaggga tttgcgagaa cactgtcggc   1740
tcttacacct gcaaatgcgc agctgggtac cagcaagacg gcaactcatg cactgacatt   1800
gacgagtgcg ccaacggcac tcacaactgc catgcctccg cgacatgcac gaacacgcaa   1860
ggctcctttg agtgcgcctg caacgcaggc ttcagcggca acggggttga atgcaacgac   1920
gtcgacgagt gctcgactga cgctgacgat tgcggagaga acacactgtg caacaacaca   1980
gttggcagct tcgagtgcac atgcatggct ggcttcgagg ccgcggacgc gaagacctgc   2040
aaagacatcg acgaatgtgc aagcgggacc cacacttgct ccacccacgc gacatgcacc   2100
aacactgctg ggtcgttcac atgtgagtgc aacccaggct ttgacggtga cggccacaag   2160
tgcgaggacg tggacttctg cggccagggg ctgcacgact gcaacgtgca tgcagagtgc   2220
tcggaaagcg acgacaacac caccttcaag tgcacctgcg gcattgggta cagcggggaa   2280
ggccacgggg agaatggttg ccaagacatt gatgagtgcg cccaagatgc catctgtggg   2340
gagaacacag tgtgtaccaa cacaccaggt agctttgaat gtcgtgtgt ggaagggttc   2400 gtggctgtgg gagcgaagct caagggagca acttcattga cctgcataga catcgatgaa   2460
tgcaacgacg cctcgaaaaa cacttgcgcc acgtcagctg acggaggctc ttgcaagaac   2520
accgcaggca gctatgagtg ctcgtgtttg cctgggttcc agggcgacgg ccacagctgc   2580
acagatattg atgagtgcgc cacccaaggc gtatgcgggg aacatgcgac ctgcgaaaac   2640
actgcgggtt cgtacaattg cacctgcgag gcgggttaca ctcagcaaga tggggccgtc   2700
ggctgcattg atattgatga gtgtgcagcc tccacagcag tgttacccgc caacgccact   2760
tgcgtgaaca ctgaaggcag ctatacattc gaatgcgtgc ccggctaccg ccatacggag   2820
aatggctgta ccaagattga tttctgcagc gaaaagggat gcaatgcgaa tgccagctgc   2880
aaggagaacg atgcgggcac cgaagccatc tgcacctgcc acagcgggta cgagggcaat   2940
ggcgaaggag aagaagggtg caaaaacatt gacgagtgct ccgtgggaga gccatgcaaa   3000
gacttcggcg agggcggcgt ctgtgtcgat tctccgggat ccttcagctg ctcttgcgcc   3060 accggttttta tcaagaggcg atctacttgc caggacatag atgagtgcct cgacggaaag   3120
atgaacactt gcgcccccgt cggggtatc tgcacgaaca ccgtcggctc cttcacctgc   3180
tcttgcgctg ctggcttcac gggtgacggc cttacttgcg aggacatcga cgaatgtgct   3240
acggcggcac acacgtgcga ccccaacgcc acctgtgtca acactgtcgg cagcttcgaa   3300 tgccggatgca aggagggatt ctctggtgac ggccacacat gcaccgatat cgacgaatgc   3360
```

```
gctgaccota  accttaacaa  atgcgacaca  cacaagggca  tctgccagaa  cggcactgga   3420
tcctacactt  gcggatgcag  gcctggatac  agtctggcgg  cggacggctt  cacttgcgac   3480
aatgtcgatg  agtgcgctgc  ggggacggcc  acttgcggag  agcgcagctt  ctgcgtggac   3540
acgcaagggt  catacaagtg  cgagtgcaag  aacggctacc  gccagtctgg  ggaggactgc   3600
gtggacgttg  acgagtgcga  ggctgatgtg  cacacatgca  gcgagcacgc  tacgtgcacg   3660
aacactgagg  ggagccacac  ctgcacctgc  aatgaagggt  accagggaga  cggaaagaag   3720
tgcgagaaga  cagtgggccc  ttgcgacaac  tcgccatgcg  gcaacaacgc  catgtgtgaa   3780
gctactgccg  atagctacaa  ctgcacttgc  aaagctggct  acgagatgaa  ggacggggcc   3840
tgtgtcgaca  tcgatgagtg  ccagtcgggc  acccacaact  gcgacccgca  tgctgactgc   3900
agcaacaccg  atggatcctt  cacgtgcacg  tgcggttctg  gctacactgg  tgtgggtacc   3960
ctttgcgagg  atgtggacga  gtgcgcgggc  aaccatgcgg  gctgtgacat  caacgctgtt   4020
tgcactaacg  tccctggctc  gttcacttgc  gagtgcaaga  gtggcttcga  aggcgatggg   4080
cacgagtgta  cggagaaagt  gctgctccct  ggccagattc  actgcgattc  gtggactgca   4140
tggaccgaat  gtacagctga  aactaagcag  agcacccgca  agtgcgtggc  tcttcctctc   4200
aaggtcgagg  tgaagctttg  ccccgatgct  gacatttcag  cctgcggtga  actcggcgag   4260
tggtcatcat  gcccaggagt  tgacaacaac  ctgtcgcacc  gcagagcaga  gaagttcggg   4320
gagccgggct  gtgagcacgc  tgaggaggtc  agggagtgcc  cagatgaaga  agttgaggag   4380
cgctgtggtg  cctttggcga  gtggactgca  tgccggcgatc  cttctgaggg  cttgaggacc   4440
aggacgcgcc  agaactgccc  agaagaggca  gaattcgagc  actgcacaat  gccctctgca   4500
ccatccgttc  ccgagggcgg  cagcagctgc  acagagttcg  gggcctggag  tgaatgcgtg   4560
gctgacgctc  atgggatcaa  gatgcagcac  agaacgtgcg  tacacaatga  agctgtgcag   4620
gaacacagaa  tctgcaccgt  ggaagatcca  caacagtgcg  gggagtggtc  gcagtggtca   4680
gagtgcaaga  atggcaagca  gtacagaggc  gccgccggat  gcgcgtctgt  gtacgaagtc   4740
agagcctgca  gcgcgctag   cgatgcgaaa  gaatgctctt  ttggtgcgtg  gagcggctgc   4800
gtggtggagt  ttggcggtca  cacttacaaa  gtgcgaaact  caatcgactg  cgagctcagt   4860
gagctgcagg  cttgcaagcc  gagcgccgcc  accgagggcg  agggcaagtg  cgctgcttgg   4920
agccctgga   cgatctgcag  ggacggcatg  cagactcgcg  actgcaaaag  cctgggtgtt   4980
caggagtccc  gcccatgctc  agctgaagga  gagaccgatt  cttgcggagc  ctttggaccc   5040
ttcgagccgg  cagcttgcaa  ggctggcgag  atggtcacga  ggacgcggga  gtgcaacggt   5100
gctcagcaga  aggaaaccag  actgtgcaat  cctgagggca  atgacaactg  caacaactgg   5160
ggtgcttgga  cagagtgctc  gctaattgtg  gcggctctg   ccctgcggtc  tcgcgaggag   5220
tccacttgcg  gctatgtgga  gttagaggag  tgcagtggca  gcagcagcag  cggcgaccag   5280
accgtccact  gcggcagctg  gtcggagtgc  tccatgaaga  aaacgagcg   cacctgtgat   5340
gtcctctctg  acggatccca  caccagcgtt  actgaagtgc  tcacctgcga  cgacgtgctg   5400
cctgactctt  gcggtgaatt  tggcgagtgg  tccaatgta   gcgctgacgg  cttgcactcg   5460
aggtccctgt  caggctgccc  agacgtaact  gaagtgatga  cttgcggcag  cgaaaactgc   5520
ccggctttcg  gcgagtggag  cgagtgcggc  agccagagg   acggcctacg  gtcgcgtcag   5580
cgaacgaact  gcgaagaggg  atccggctgc  atttgctccg  agacagaagc  ctgtgttaac   5640
actgagctcc  accccatccc  attgccagtt  cctggcggcg  gcgagggcag  cgagaacggc   5700
gagggtggcc  aaaccggaga  ggagggaacg  gagggaggcg  caggcggtgc  tggaggatcc   5760
```

```
ggtggtgctg aggagctgcc cggagaagag ggtggcgcag gtgccggcgg agaaggaggc    5820
tctggcggta atgctgagga gctgcccgga aaggggggtg ctggcgaagc tggaggctct    5880
ggcggtagtg ctgaggagct gcccggaaaa gagggcggcg caggtgccgg cggaggagga    5940
ggctctggcg gtagtgctga ggagctgcct ggagaagagg gcggcgcagg tgccggcgga    6000
gaaggaggct ctggcggcaa tgctgaggag ctgcccggag aagagggcgg cgcaggtgct    6060
ggaggagccg aaggcgagac agggaaacct ggcggcgaag agggtggcgc aggcggcgct    6120
ggtgagggtg ctggcggtga aggtggtgag gtccagcctg agagggagag aggggcgagt    6180
gaaggaggcg agcaagtgcc ggaaaccccct gagacacccg aaccggaaac acctgaagct    6240
gagagacctg aagagcaacc ctcgacggaa actccagcag aggagcccac cgaaggcggt    6300
gcagaagaag aggagaagga ggagggcagc ggcttcccca cggcagctgt tgccggaggt    6360
gtaggtggtg tactactgct ggcagcagtg ggtggtggcg ttgccgcgta ctccggtggt    6420
ggtgagggtg gcggtgccga ggaggctgag caagttgagt ttgaaggtga agagtcgggt    6480
ggtgcgtctg ccgaaacacc tgaggctgat actgtgattg acatcactga cgaagacgac    6540
tactgggcag acagtggtga catccag                                         6567

<210> SEQ ID NO 28
<211> LENGTH: 293
<212> TYPE: DNA
<213> ORGANISM: Chicken

<400> SEQUENCE: 28
gtggtgattg aatctgctcc agccaagatg gctcaccctc ctgtggtgat tgagtctgct     60
ccggtcgagg tggtccatcc tcctatggtg attgaatctg ctccacccaa gatggctcaa    120
cctccgatgg tgattgagtc tgctccaccc aagatggctc aaccaccttat ggtgattgag    180 tcggctcccg tcgaggtggt ccatcctcct atggtgatgg aagccgctcc accgtgaag    240 ggaagatacc tcgctgctga ggatgaggtg gaagagcagt ttgaatcgaa cag           293

<210> SEQ ID NO 29
<211> LENGTH: 97
<212> TYPE: PRT
<213> ORGANISM: Chicken

<400> SEQUENCE: 29

Val Val Ile Glu Ser Ala Pro Ala Lys Met Ala His Pro Pro Val Val
 1               5                  10                  15

Ile Glu Ser Ala Pro Val Glu Val Val His Pro Pro Met Val Ile Glu
            20                  25                  30

Ser Ala Pro Pro Lys Met Ala Gln Pro Pro Met Val Ile Glu Ser Ala
        35                  40                  45

Pro Pro Lys Met Ala Gln Pro Pro Met Val Ile Glu Ser Ala Pro Val
    50                  55                  60

Glu Val Val His Pro Pro Met Val Met Glu Ala Ala Pro Thr Val Lys
65                  70                  75                  80

Gly Arg Tyr Leu Ala Ala Glu Asp Glu Val Glu Glu Gln Phe Glu Ser
                85                  90                  95

Asn

<210> SEQ ID NO 30
<211> LENGTH: 196
<212> TYPE: DNA
<213> ORGANISM: Chicken
```

-continued

```
<400> SEQUENCE: 30
cctgcaggtt gtactaagag cgctttatga ctatcgggag ctcaaatgcg gctcagcatg     60
ccggaacgtg gcatttttgg tacacggagg tatcacctcg agcgaatggg cgggggtctt    120
tccgcaaaca agcgttccac caaaacctaa ggtggaaaac tgttcagttg catttaatta    180
cgcttttgta aatacc                                                    196

<210> SEQ ID NO 31
<211> LENGTH: 65
<212> TYPE: PRT
<213> ORGANISM: Chicken

<400> SEQUENCE: 31

Leu Gln Val Val Leu Arg Ala Leu Tyr Asp Tyr Arg Glu Leu Lys Cys
1               5                   10                  15

Gly Ser Ala Cys Arg Asn Val Gly Ile Leu Val His Gly Gly Ile Thr
            20                  25                  30

Ser Ser Glu Trp Ala Gly Val Phe Pro Gln Thr Ser Val Pro Pro Lys
        35                  40                  45

Pro Lys Val Glu Asn Cys Ser Val Ala Phe Asn Tyr Ala Phe Val Asn
    50                  55                  60

Thr
65

<210> SEQ ID NO 32
<211> LENGTH: 646
<212> TYPE: DNA
<213> ORGANISM: Chicken

<400> SEQUENCE: 32
cgaattgcac cccattccag cccccggtac ggaaacaggc gaaggagagg gagagaccga     60
gacaggcgaa ggcgaaactg gtgaagcagg tggcgaggaa ggcgagcaaa caggagaagg    120
cgaagtgcag cccccagaag aagagcttcc tggggagagt gtaactgagc ctgaggagaa    180
gcctgaggag gagctacctg aggaggaggt tactgagcct gaggagaagc ctgaggaggg    240
tgtgactcag cctgaggaga cacctgagca gcctgttgag ggtaccgaag aagagggcaa    300
gcaggagtct gaggctgccc ccgaaactcc tgccgtccag ccaaaaccag gagagggtca    360
cgaacgccca gaacccgaag aggaggagga gaagaaggaa gaaggcggcg gcttcccaac    420
agctgcagtg gcaggaggtg ttggtggtgt gttgctcata gctgctgtag gtggtggtgt    480
tgcagccttc actagcggcg gaggtggcgc tggcgcacag gaggcagaac aggtcgagtt    540
cgaaggagaa gataccggag cagcaactgc cgagacacct gaagccgata cagttatcga    600
catcacagac gaagacgact actgggccga cagcggcgac attcag              646

<210> SEQ ID NO 33
<211> LENGTH: 215
<212> TYPE: PRT
<213> ORGANISM: Chicken

<400> SEQUENCE: 33

Glu Leu His Pro Ile Pro Ala Pro Gly Thr Glu Thr Gly Glu Gly Glu
1               5                   10                  15

Gly Glu Thr Glu Thr Gly Glu Gly Thr Gly Glu Ala Gly Gly Glu
            20                  25                  30

Glu Gly Glu Gln Thr Gly Glu Gly Glu Val Gln Pro Pro Glu Glu Glu
        35                  40                  45
```

```
Leu Pro Gly Glu Ser Val Thr Glu Pro Glu Glu Lys Pro Glu Glu Glu
    50                  55                  60

Leu Pro Glu Glu Glu Val Thr Glu Pro Glu Glu Lys Pro Glu Glu Gly
65                  70                  75                  80

Val Thr Gln Pro Glu Glu Thr Pro Glu Gln Pro Val Glu Gly Thr Glu
                85                  90                  95

Glu Glu Gly Lys Gln Glu Ser Glu Ala Ala Pro Glu Thr Pro Ala Val
            100                 105                 110

Gln Pro Lys Pro Glu Glu Gly His Glu Arg Pro Glu Pro Glu Glu Glu
        115                 120                 125

Glu Glu Lys Lys Glu Glu Gly Gly Phe Pro Thr Ala Ala Val Ala
    130                 135                 140

Gly Gly Val Gly Gly Val Leu Leu Ile Ala Ala Val Gly Gly Val
145                 150                 155                 160

Ala Ala Phe Thr Ser Gly Gly Gly Ala Gly Ala Gln Glu Ala Glu
                165                 170                 175

Gln Val Glu Phe Glu Gly Glu Asp Thr Gly Ala Ala Thr Ala Glu Thr
                180                 185                 190

Pro Glu Ala Asp Thr Val Ile Asp Ile Thr Asp Glu Asp Asp Tyr Trp
            195                 200                 205

Ala Asp Ser Gly Asp Ile Gln
    210                 215

<210> SEQ ID NO 34
<211> LENGTH: 16
<212> TYPE: PRT
<213> ORGANISM: Chicken

<400> SEQUENCE: 34

Val Pro Ser Thr Thr Pro Val Glu Asn Gln His Val His Pro Tyr Ser
1               5                   10                  15

<210> SEQ ID NO 35
<211> LENGTH: 15
<212> TYPE: PRT
<213> ORGANISM: Chicken

<400> SEQUENCE: 35

Val Pro Ser Thr Thr Pro Val Glu Asn Gln His His Pro Tyr Ser
1               5                   10                  15

<210> SEQ ID NO 36
<211> LENGTH: 15
<212> TYPE: PRT
<213> ORGANISM: Chicken

<400> SEQUENCE: 36

Met Gly Arg Lys Gly Arg Ser Phe Tyr Tyr Gly Gly Tyr Pro Ser
1               5                   10                  15

<210> SEQ ID NO 37
<211> LENGTH: 16
<212> TYPE: PRT
<213> ORGANISM: Chicken

<400> SEQUENCE: 37

Tyr Gly Arg Lys Gly Arg Ser Phe Tyr Tyr Gly Gly Tyr Pro Ser Gly
1               5                   10                  15
```

-continued

```
<210> SEQ ID NO 38
<211> LENGTH: 14
<212> TYPE: PRT
<213> ORGANISM: Chicken

<400> SEQUENCE: 38

Tyr Pro Ser Tyr Ser Trp Ser Tyr Pro Ala Tyr Thr Arg Val
1               5                   10

<210> SEQ ID NO 39
<211> LENGTH: 13
<212> TYPE: PRT
<213> ORGANISM: Chicken

<400> SEQUENCE: 39

Tyr Pro Ser Tyr Ser Ser Tyr Pro Ala Tyr Thr Arg Val
1               5                   10

<210> SEQ ID NO 40
<211> LENGTH: 15
<212> TYPE: PRT
<213> ORGANISM: Chicken

<400> SEQUENCE: 40

Gly Lys Arg Met Tyr Ser Thr Gly Tyr Tyr Gly Tyr Gly Tyr Pro
1               5                   10                  15

<210> SEQ ID NO 41
<211> LENGTH: 10
<212> TYPE: PRT
<213> ORGANISM: Chicken

<400> SEQUENCE: 41

Lys Arg Met Tyr Ser Thr Gly Tyr Gly Pro
1               5                   10

<210> SEQ ID NO 42
<211> LENGTH: 12
<212> TYPE: PRT
<213> ORGANISM: Chicken

<400> SEQUENCE: 42

Ser Phe Ser Pro Val Ala Pro Gln Glu Leu Phe Leu
1               5                   10
```